United States Patent
Guo et al.

(10) Patent No.: US 12,188,155 B2
(45) Date of Patent: Jan. 7, 2025

(54) SPINNERETS, BREAKER PLATES AND DIE BODIES HAVING CONTOURED SURFACES WITH NO FLAT SURFACES BETWEEN ADJACENT HOLES

(71) Applicant: Ethicon, Inc., Somerville, NJ (US)

(72) Inventors: Jianxin Guo, Livingston, NJ (US);
Gaoyuan Chen, Hillsborough, NJ (US);
Jianguo Zhou, Bethlehem, PA (US);
John Collier, Franklin Lakes, NJ (US);
Joseph Richard Vliet, Jr., Califon, NJ (US); Glenn R. Cook, Clinton, NJ (US)

(73) Assignee: Ethicon, Inc., Raritan, NJ (US)

( * ) Notice: Subject to any disclaimer, the term of this patent is extended or adjusted under 35 U.S.C. 154(b) by 34 days.

(21) Appl. No.: 17/217,155

(22) Filed: Mar. 30, 2021

(65) Prior Publication Data

US 2021/0332499 A1     Oct. 28, 2021

Related U.S. Application Data

(60) Provisional application No. 63/016,045, filed on Apr. 27, 2020.

(51) Int. Cl.
*D01D 4/02*        (2006.01)
*B29C 48/05*       (2019.01)
*B29C 48/345*      (2019.01)

(52) U.S. Cl.
CPC .............. *D01D 4/02* (2013.01); *B29C 48/05* (2019.02); *B29C 48/345* (2019.02)

(58) Field of Classification Search
CPC .................................. D01D 4/06; B29C 48/05
See application file for complete search history.

(56) References Cited

U.S. PATENT DOCUMENTS 3,259,938 A * 7/1966 Martin ..................... D01D 4/00
                                                425/464
3,615,995 A * 10/1971 Buntin ................. A24D 3/0237
                                                156/167
(Continued)

FOREIGN PATENT DOCUMENTS

CN      101089253      12/2007
CN      202925165       5/2013
(Continued)

OTHER PUBLICATIONS

International Search Report issued in corresponding International Application No. PCT/IB2021/053220, mailed on Jul. 5, 2021, 5 pages.

*Primary Examiner* — Seyed Masoud Malekzadeh

(57) ABSTRACT

A spinneret for extruding fibers includes a plate having a proximal surface and a distal surface. The spinneret includes a plurality of holes formed in the plate that extend between the proximal surface and the distal surface of the plate. The holes are spaced from one another, and each hole has a distal end that extends along a central axis. The spinneret has a plurality of contoured entrance zones formed in the proximal surface of the plate, whereby each contoured entrance zone is associated with one of the holes. Each contoured entrance zone extends distally from the proximal surface of the plate to a proximal end of the hole associated therewith. Each contoured entrance zone has substantially no planar or flat surfaces normal to the direction of the central axis of the distal end of the hole associated therewith.

17 Claims, 53 Drawing Sheets

(56) References Cited

U.S. PATENT DOCUMENTS

| | | | | |
|---|---|---|---|---|
| 3,684,415 | A * | 8/1972 | Buntin | D01D 4/025 |
| | | | | 65/525 |
| 3,762,850 | A * | 10/1973 | Werner | D01D 4/06 |
| | | | | 425/382.2 |
| 3,913,421 | A * | 10/1975 | Hawkins | B23P 15/16 |
| | | | | 29/523 |
| 3,938,925 | A * | 2/1976 | Lees | B29C 48/693 |
| | | | | 425/464 |
| 4,072,457 | A | 2/1978 | Cooksey et al. | |
| 4,785,996 | A * | 11/1988 | Ziecker | B05B 7/0861 |
| | | | | 425/7 |
| 5,165,940 | A * | 11/1992 | Windley | D01D 4/025 |
| | | | | 264/211.14 |
| 5,259,753 | A * | 11/1993 | Kobsa | D01D 4/02 |
| | | | | 425/464 |
| 5,330,348 | A * | 7/1994 | Aneja | D01D 5/24 |
| | | | | 425/464 |
| 5,650,067 | A | 7/1997 | Wilken-Trenkamp | |
| 10,301,746 | B2 * | 5/2019 | Diaz de Leon Izquierdo | D01D 5/088 |
| 11,060,207 | B2 * | 7/2021 | Diaz de Leon Izquierdo | D01D 4/02 |
| 11,136,696 | B2 * | 10/2021 | Chen | B29C 48/802 |
| 11,306,413 | B2 * | 4/2022 | Taylor | B29C 48/92 |
| 11,885,042 | B2 * | 1/2024 | Taylor | B29C 48/345 |
| 2002/0107326 | A1 | 8/2002 | Hendess | |
| 2002/0153635 | A1 | 10/2002 | Belli et al. | |
| 2003/0041463 | A1 * | 3/2003 | Proulx | D02G 3/44 |
| | | | | 30/276 |
| 2003/0236554 | A1 * | 12/2003 | Chen | B29C 48/875 |
| | | | | 606/228 |
| 2005/0035052 | A1 * | 2/2005 | Kelly | B29C 48/694 |
| | | | | 210/446 |
| 2013/0066369 | A1 * | 3/2013 | Collier | A61B 17/06166 |
| | | | | 606/228 |
| 2014/0103556 | A1 * | 4/2014 | Diaz de Leon Izquierdo | D01D 5/088 |
| | | | | 425/72.2 |
| 2017/0306527 | A1 * | 10/2017 | Taylor | B29C 48/05 |
| 2019/0292684 | A1 * | 9/2019 | Diaz de Leon Izquierdo | D01D 4/025 |
| 2020/0149194 | A1 * | 5/2020 | Chen | B29C 48/05 |
| 2021/0332499 | A1 * | 10/2021 | Guo | B29C 48/05 |
| 2022/0073849 | A1 * | 3/2022 | Jeon | C12M 21/08 |
| 2022/0205138 | A1 * | 6/2022 | Taylor | B29C 48/19 |

FOREIGN PATENT DOCUMENTS

| | | | | |
|---|---|---|---|---|
| CN | 203569249 | | 4/2014 | |
| CN | 204311166 | | 5/2015 | |
| CN | 206438358 | | 8/2017 | |
| FR | 1463403 | | 12/1996 | |
| GB | 1126653 | | 9/1968 | |
| JP | 1-168907 | | 7/1989 | |
| JP | 2004-225199 | | 8/2004 | |
| KR | 19990030797 A | * | 5/1999 | |
| WO | 99/51798 | | 10/1999 | |
| WO | WO-9951798 A1 | * | 10/1999 | D01D 4/00 |
| WO | 2016170493 | | 10/2016 | |

* cited by examiner

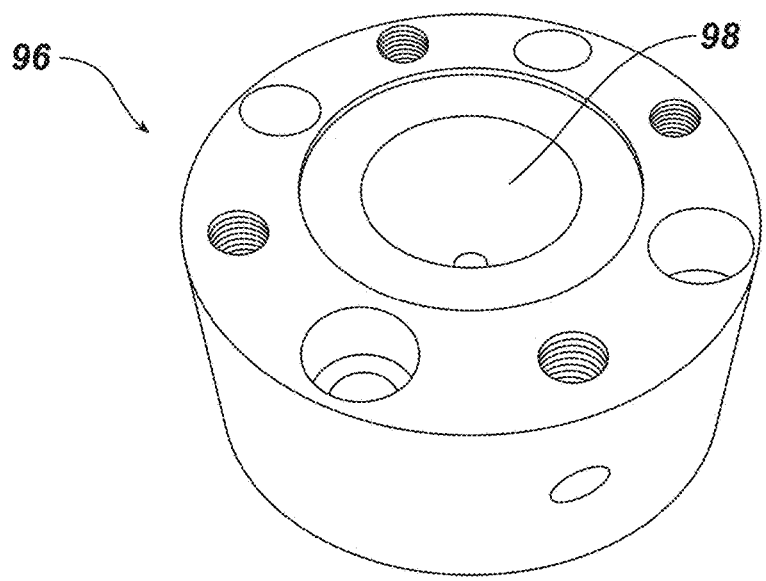
FIG. 25A _PRIOR ART_
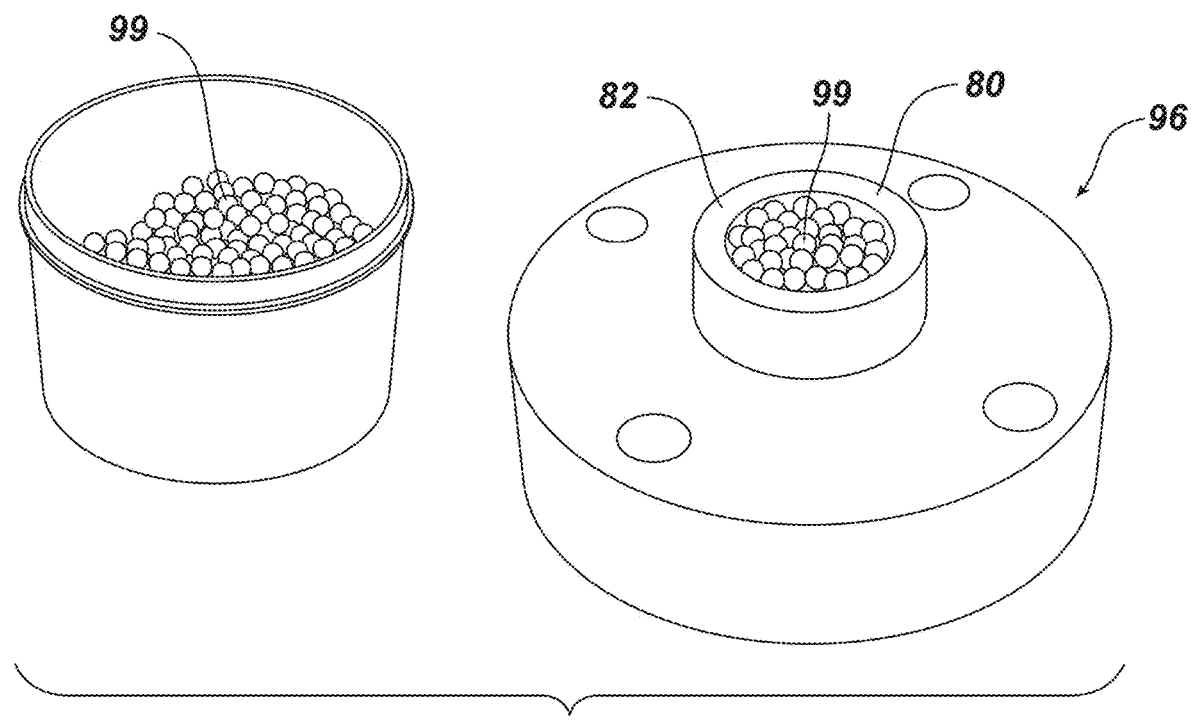
FIG. 25B _PRIOR ART_

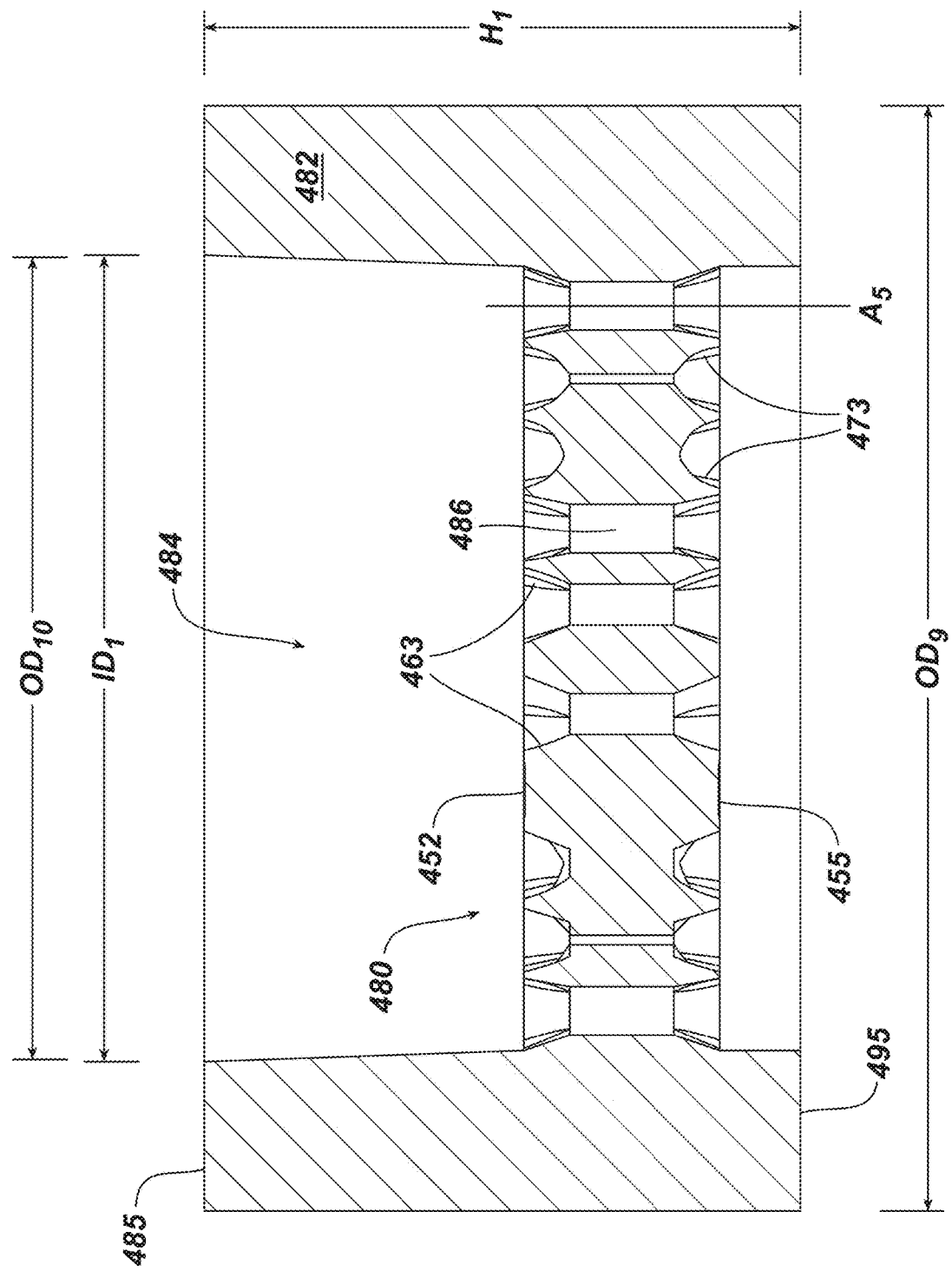

SPINNERETS, BREAKER PLATES AND DIE BODIES HAVING CONTOURED SURFACES WITH NO FLAT SURFACES BETWEEN ADJACENT HOLES

CROSS-REFERENCE TO RELATED APPLICATIONS

The present patent application claims benefit of U.S. Provisional Application No. 63/016,045, filed on Apr. 27, 2020, the disclosure of which is hereby incorporated by reference herein.

BACKGROUND OF THE INVENTION

Field of the Invention

The present patent application is generally related to systems, devices and methods used to make sutures, and is more specifically related to spinnerets, breaker plates and die bodies used for extruding suture fibers.

Description of the Related Art

FIGS. 1 and 2 show a prior art spinneret 50 having a flat top surface 52, a flat bottom surface 54, and a plurality of holes 56 that extend from the flat top surface 52 to the flat bottom surface 54. A polymer melt or solution is forced through the holes 56 for forming fibers that are used to make sutures. The spinneret 50 has a flat, planar surface 58 (shaded blue in FIG. 1), which is located between the holes 56. As the polymer melt or solution is extruded through the spinneret 50, the flow velocity of the polymer melt slows down and/or stagnates over the polymer wetted surfaces 58 (i.e., planar surfaces that are normal to the direction of the central axes of the distal ends of the respective holes 56).

FIG. 2 illustrates the flow velocity (in mm/sec) profile of the polymer melt as it flows through the holes 56 and across the flat, polymer wetted surfaces 58 of the spinneret 50. The polymer melt flows through the holes 56 at a flow velocity that is close to a preferred, maximum flow velocity. The flow velocity of the polymer melt over the flat, polymer wetted surfaces 58 of the spinneret 50 includes a "dead area" where the flow velocity is slower and is typically less than 5% of the above-noted maximum flow velocity. In some instances the "dead area" on a spinneret is estimated to be as high as 91% of the total color shaded area (including the entrance zones of the holes) in FIG. 2 (i.e., the purple shaded area of the flat, top surface 52 of the spinneret). The space above the shaded area (i.e., the polymer wetted surfaces) can be filled up by a polymer melt under extrusion pressure. The above-described situation is problematic because the polymer melt tends to stagnate in the "dead area" of the polymer wetted surfaces 58, which will result in significant degradation of the polymer at high extrusion temperatures.

FIGS. 3 and 4 show a second prior art spinneret 50' having a flat top surface 52', a flat bottom surface 54', and a plurality of holes 56' extending from the flat top surface 52' to the flat bottom surface 54'. The holes 56' are configured in a circular pattern that extends around the base of a cone 60' that projects above the flat top surface 52' of the spinneret 50'. FIG. 4 shows the "dead areas" 58' of the flat top surface 52' where the flow velocity of the polymer melt is less than 5% of the preferred, maximum flow velocity. The "dead areas" are located between the adjacent holes 56'. The "dead areas" 58' shown in FIGS. 3 and 4 comprise a lower percentage of the "dead area" found in the first prior art spinneret 50 shown in FIGS. 1 and 2, however, the "dead areas" 58' still amount to about 43% of the total color shaded area (including holes 56") in FIG. 4 of the flat top surface of the spinneret 50'. Thus, the polymer melt that is extruded through the holes 56' of the spinneret 50' slows down and becomes stagnate in the "dead areas" 58', whereupon significant degradation of the polymer melt occurs at high extrusion temperatures.

There have been some efforts directed to designing spinnerets that seek to improve the flow velocity of the polymer solution through the holes of the spinneret. For example, Chinese patent document CN 202925165 seeks to modify the shape of trenches formed on a proximal surface of a spinneret to improve the spinning potential energy of a spinning solution and the flowability of the spinning solution for preventing the spinning solution from being degraded and carbonized.

FIG. 5 is a cross-sectional view of the spinneret 50" disclosed in CN 202925165. The spinneret 50" has a flat top surface 52", a flat bottom surface 54" and a plurality of holes 56" that extend from the top surface 52" to the bottom surface 54". The spinneret 50" includes an inner groove 60" and an outer groove 62" that are formed in the top surface 52" of the spinneret. A set of inner holes 56A" is located within the inner groove 60" and a set of outer holes 56B" is located within the outer groove 62". Within each groove, the respective holes 56A" and 56B" are spaced from one another so that flat surfaces or dead zones 58" are located between the adjacent holes 56A", 56B". As a polymer solution flows through the spinneret 50", the velocity of the polymer material within the dead zones 58" is significantly less than a preferred maximum velocity of the polymer solution, whereupon the polymer solution becomes stagnate in the dead zones 58" resulting in significant degradation of the polymer material at high extrusion temperatures.

In spite of the above advances, existing spinnerets remain deficient because they have flat spots or dead areas between adjacent holes that cause polymer degradation, and non-uniform fiber structure formation, which contributes to severe fluctuations in fiber strength and/or fiber tenacity.

Thus, there remains a need for improved spinnerets that minimize or eliminate the flat spots or dead areas between adjacent holes, that maximize the flow velocity of polymer melts as they flow through the spinnerets, that minimize polymer degradation and/or fiber tenacity variations within and/or between fiber spools, and that significantly increase the average tenacity and/or strength of the extruded fibers.

SUMMARY OF THE INVENTION

In one embodiment, a spinneret used for forming multi-filaments from polymers preferably includes a plate having a top or proximal surface, a bottom or distal surface, and adjacent holes that extend from the proximal surface toward the distal surface of the plate.

In one embodiment, the plate of the spinneret preferably has an outer diameter of about 30-110 mm.

In one embodiment, each hole that is formed in the plate desirably has a proximal end and a distal end.

In one embodiment, the number of holes that are formed in the plate may be between four and 80 holes.

In one embodiment, the four to 80 holes may be positioned within one to three concentric rings having outer diameters in the range of 10-90 mm.

In one embodiment, the distance between any two adjacent holes may be in the range of about 3-20 mm.

In one embodiment, the holes are spaced from one another with no flat surfaces between adjacent holes.

In one embodiment, a contoured entrance zone preferably surrounds the proximal end of each hole that is formed in the plate. In one embodiment, the contoured entrance zone preferably includes contoured surfaces that extend from the proximal surface of the plate (e.g., the polymer wetted surface of the plate) to the proximal end of each hole.

In one embodiment, the contoured entrance zone surrounding the proximal end of each hole directly borders the contoured entrance zone surrounding each adjacent hole so that substantially no flat or planar surfaces normal to the direction of the central axis of distal ends of the holes (e.g., a central axis extending along the length of a capillary hole) remain between adjacent holes on the proximal surface (e.g., the polymer wetted surfaces) of the plate. The contoured surfaces of the contoured entrance zones that surround the proximal ends of the holes may include sloping surfaces, and curved surfaces including concave curved surfaces and convexly curved surfaces.

In one embodiment, the plate may include a centrally located conical projection that extends above the flat, proximal surface of the plate, and the adjacent holes located at the base of the conical projection. In one embodiment, the holes may be arrayed in an annular or ring-shaped configuration around the base of the cone. In one embodiment, a ring (e.g., a slot) having an annular shape may be formed in the proximal surface of the plate and the holes may be located within the ring.

In one embodiment, a spinneret plate may have an inner ring that contains a first set of inner holes, and an outer ring that contains a second set of outer holes. In one embodiment, the outer ring may surround the inner ring. In one embodiment, the inner and outer rings may be concentric and may surround the base of a conical projection that projects above the proximal face of the spinneret.

In one embodiment, a spinneret may have a plate with two or more rings (e.g., three rings) formed in the top or proximal face of the plate. In one embodiment, holes are formed in each of the two or more rings. In one embodiment, contoured entrance zones are formed in the rings at the proximal ends of each hole so that within the polymer wetted area of the spinneret, and between adjacent holes, there are substantially no flat or planar surfaces normal to the direction of the central axes of distal ends of the respective holes (e.g., the central axes of capillary holes). In one embodiment, the central axes at the distal ends of the respective holes are preferably longitudinal axes that extend through capillaries that extend to the bottom or distal surface of the plate of the spinneret.

In one embodiment, the contoured entrance zones are proximal to proximal ends of each hole so that there are substantially no flat or planar surfaces normal to the direction of the central axes of distal ends of the respective holes (e.g., the central axes of capillary holes).

In one embodiment, the base of the conical projection preferably has an outer diameter of at least 20 mm and a height of about 20-40 mm.

In one embodiment, a spinneret preferably includes a plate having 4-80 holes with a center cone projecting above a proximal surface of the plate. In one embodiment, the spinneret preferably includes contoured entrance zones formed in the proximal surface (e.g., the polymer wetted surfaces) of the plate, whereby each contoured entrance zone is associated with the proximal end of one of the holes that are formed in the plate. In one embodiment, the contoured entrance zones are located within the wetted area of the spinneret plate so that there are no flat surfaces between adjacent holes that are normal to the direction of central axes of distal ends of the holes.

In one embodiment, a polymer extrusion die assembly is configured for the extrusion of multi-filaments and/or suture fibers. In one embodiment, the polymer extrusion die assembly preferably includes a die body having a cone-shaped hollow center, and the spinneret disclosed herein having 4-80 holes having a proximal polymer wetted surface having no flat surfaces normal to the direction of central axes of distal ends of the holes. In one embodiment, when the spinneret is assembled with the die body, a conical projection of the spinneret is disposed within the cone-shaped hollow center of the die body.

In one embodiment, a breaker plate used for extruding multifilaments from polymers preferably includes a cylindrical hollow space for holding filtering elements (e.g., filtering screens) and/or mixing elements (e.g., stainless steel balls), and a perforated plate having contoured entrance and exit zones for flow holes on both the proximal and distal surfaces of the plate with substantially no flat surfaces normal to the central axes of the respective flow holes. In one embodiment, the breaker plate preferably includes ridges that extend between the contoured entrance zones that lie in the same plane as the proximal surface of the plate for contacting and supporting the filtering element to minimize the risk of deforming, collapsing and/or damaging the filtering element under high pressure during an extrusion process. Incorporating the breaker plate disclosed herein into a polymer melt extrusion die will preferably minimize polymer degradation, improve fiber uniformity and significantly increase the fiber strength of extruded polymer filaments.

In one embodiment, a breaker plate for extruding fibers preferably includes a plate having a proximal surface and a distal surface, and a plurality of holes formed in the plate that extend between the proximal surface and the distal surface of the plate, whereby the holes are spaced from one another and each hole extends along a central axis.

In one embodiment, the breaker plate includes a plurality of contoured entrance zones formed in the proximal surface of the plate, whereby each contoured entrance zone is associated with one of the holes. In one embodiment, each contoured entrance zone preferably extends distally from the proximal surface of the plate to a proximal end of the hole associated therewith. In one embodiment, each contoured entrance zone desirably has substantially no planar or flat surfaces normal to the central axis of the hole associated therewith.

In one embodiment, the breaker plate may include a plurality of contoured exit zones formed in the distal surface of the plate, whereby each contoured exit zone is associated with one of the holes. In one embodiment, each contoured exit zone desirably extends distally from a distal end of the hole associated therewith to the distal surface of the plate, whereby the contoured exit zone has substantially no planar or flat surfaces normal to the central axis of the hole associated therewith.

In one embodiment, each hole that is formed in the plate has the proximal end that is closer to the proximal surface of the plate and the distal end that is closer to the distal surface of the plate.

In one embodiment, each contoured entrance zone preferably surrounds the proximal end of the hole that is associated therewith, and the contoured entrance zone desirably includes contoured surfaces that extend from the proximal surface of the plate to the proximal end of the hole.

In one embodiment, the contoured entrance zone surrounding each hole directly borders the contoured entrance zone surrounding each adjacent hole to define a wetted area of the proximal surface of the plate having no planar or flat surfaces normal to the central axes of the respective holes.

In one embodiment, the contoured entrance zones may include contoured surfaces selected from the group consisting of sloping surfaces, curved surfaces, concave curved surfaces, and convexly curved surfaces.

In one embodiment, each contoured exit zone preferably surrounds the distal end of the hole that is associated therewith, and the contoured exit zone desirably includes contoured surfaces that extend from the distal surface of the plate to the distal end of the hole.

In one embodiment, the contoured exit zone surrounding each hole directly borders the contoured exit zone surrounding each adjacent hole to define a wetted area of the distal surface of the plate having no planar or flat surfaces normal to the central axes of the respective holes.

In one embodiment, the contoured exit zones preferably include contoured surfaces selected from the group consisting of sloping surfaces, curved surfaces, concave curved surfaces, and convexly curved surfaces.

In one embodiment, about 3-60 holes are formed in the breaker plate.

In one embodiment, the breaker plate may include a tubular wall that is directly connected with the proximal surface of the plate. In one embodiment, the tubular wall preferably defines a cylindrical hollow space adapted to receive polymer mixing and/or filtering elements such as sand, stainless steel balls, sintered mesh screens to homogenize a polymer melt and/or filter impurities from the polymer melt.

In one embodiment, the breaker plate may be installed anywhere in a melt flow path from a polymer source such as an extruder or a metering pump block outlet to the inlet of a fiber extrusion die body or die assembly.

In one embodiment, a die body used for the extrusion of multifilaments from polymers has a plurality of flow distribution channels in the upper portion of the die body, and a hollow cone in the lower portion of the die body, which forms a thin layer of flow passage when assembled with a matching spinneret/cone die for extrusion.

In one embodiment, the die body has less free volume (hence less residence time) and faster heat transfer than is attained when using conventional die bodies having an inverted cone-shaped hollow space for polymer inlet flow. In one embodiment, the entrance zones of the flow channels are contoured so that there are substantially no flat surfaces normal to the polymer flow on either inlet or outlet side of the flow channels.

In one embodiment, the ridges of the contoured entrance zones are preferably all in the same plane, whereby the ridges may directly contact and support a filtering element (e.g., a mesh filtering screen) for filtration without using a separate breaker plate. In one embodiment, an adapter tube may be attached or fabricated as a single unit at the proximal end of the die body to form a tubular hollow space that is adapted to retain one or more filtering elements and/or mixing elements.

In one embodiment, a die body for extruding fibers preferably includes an inlet opening at a proximal end of the die body having a plurality of contoured entrance zones having substantially no flat surfaces normal to a central axis of the die body, a cone-shaped hollow space on a distal side of the die body, and a plurality of flow channels for polymer flow through the contoured entrance zones to an outlet region in an upper portion of the die body or near the peak area of the cone-shaped hollow space.

In one embodiment, the die body may have about 3-60 flow channels.

In one embodiment, the flow channels may extend along respective axes that are parallel to the central axis of the die body.

In one embodiment, the flow channels are preferably tilted at an angle of about 15-50 degrees with respect to the central axis of the die body so that all of the outlets of the flow channels are above or near the apex area of the cone-shaped hollow space of the die body.

In one embodiment, the contoured entrance zones desirably include contoured surfaces selected from the group consisting of sloping surfaces, curved surfaces, concave curved surfaces, and convexly curved surfaces.

In one embodiment, a polymer extrusion die assembly for extruding suture fibers may include a cone die having a cone-shaped center, and a die body having an upper portion including a plurality of flow distribution channels, a lower portion including a cone-shaped hollow center, and contoured entrance zones in communication with proximal ends of the flow distribution channels. In one embodiment, the contoured entrance zones have substantially no flat surfaces that are normal to a central axis of the die body. In one embodiment, a tubular adapter may be attached to an inlet opening of the die body.

In one embodiment, the tubular adapter is attachable to a proximal end of the die body.

In one embodiment, the tubular adapter may be integrally formed with the die body.

In one embodiment, the tubular adapter may include a filter-holder breaker plate that is attachable to a proximal end of a die body.

These and other preferred embodiments of the present patent application will be described in more detail below.

BRIEF DESCRIPTION OF THE DRAWINGS

FIG. 25A is a perspective view of a proximal end of a prior art die body.

FIG. 25B shows the breaker plate of FIG. 24 assembled with the proximal end of the die body of FIG. 25A.

FIG. 27E is another cross-sectional view of the breaker plate shown in FIGS. 27A-27D.

DETAILED DESCRIPTION OF PREFERRED EMBODIMENTS

Figure 1:
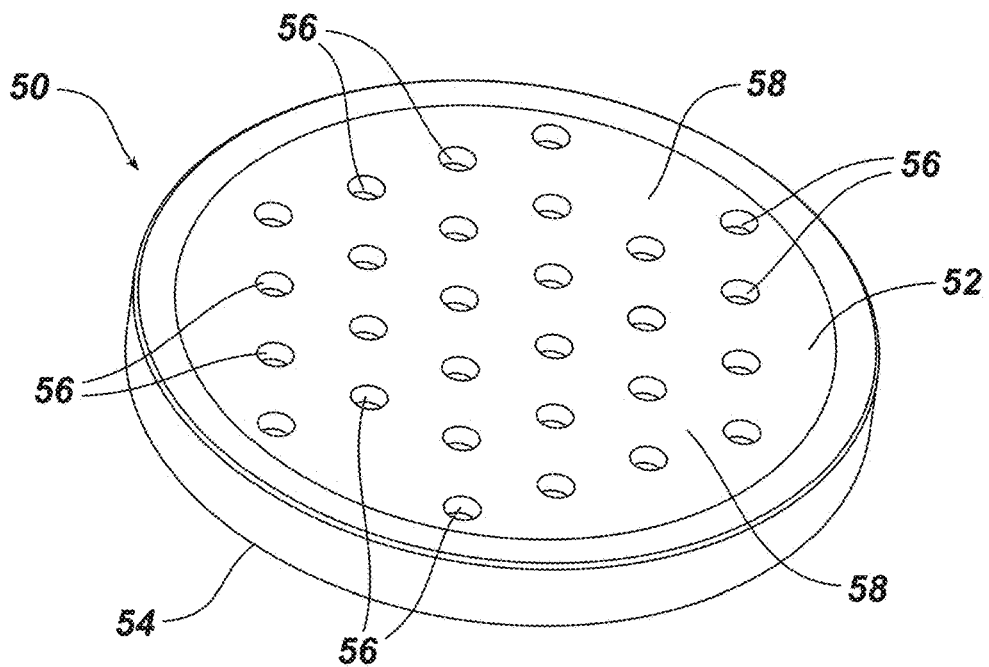
FIG. 1 is a perspective view of a prior art spinneret having holes for extruding flowable polymer.

Referring to FIGS. 6A-6B and 7A-7B, in one embodiment, a polymer extrusion die assembly 100 preferably includes a die body 102 (which may also be referred to as a "die block"), a die retainer ring 104, and a spinneret 106 that is disposed between the die body 102 and the die retainer ring 104. The polymer extrusion die assembly 100 preferably has a proximal opening 108 that is adapted to receive a material such as a polymer melt and a distal opening 110 that is configured for dispensing filaments or fibers from a lower end of the polymer extrusion die assembly. The extruded fibers may be used for making sutures.

Referring to FIGS. 8A-8D, in one embodiment, the die body 102 preferably has a leading or proximal end 112 with a flat top surface 114 and a trailing or distal end 116 with a flat bottom surface 118. The proximal end 112 of the die body 102 desirably includes the proximal opening 108 for directing a polymer melt into the proximal end of the polymer extrusion die assembly 100 (FIG. 6A).

Figure 8A:
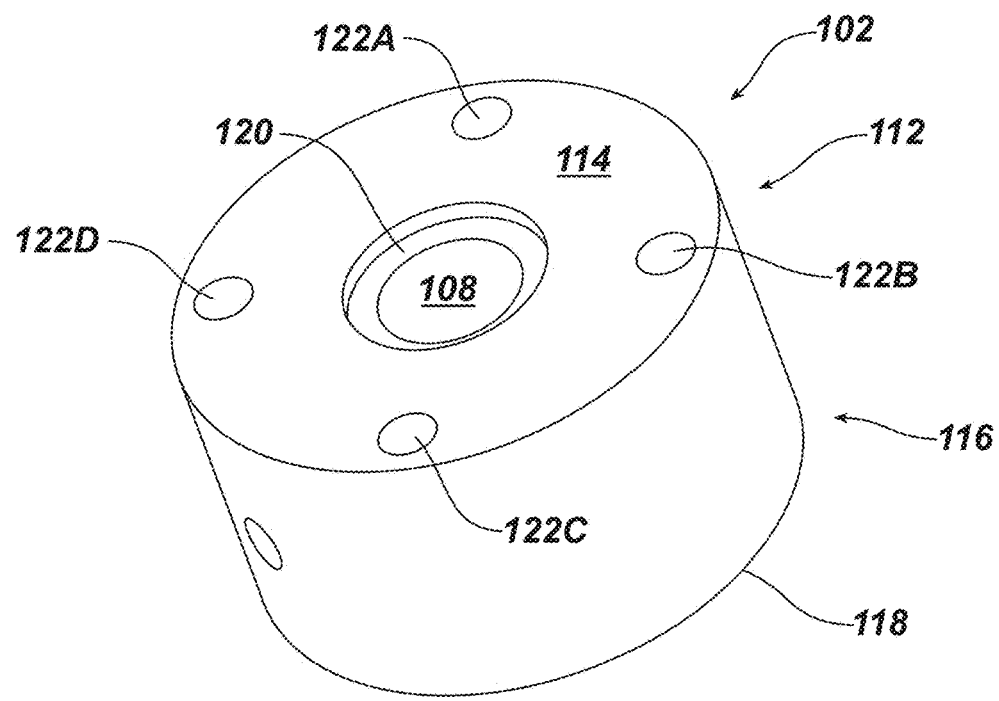
FIG. 8A is a perspective view of a proximal end of the die body shown in FIGS. 7A and 7B.
Figure 8B:
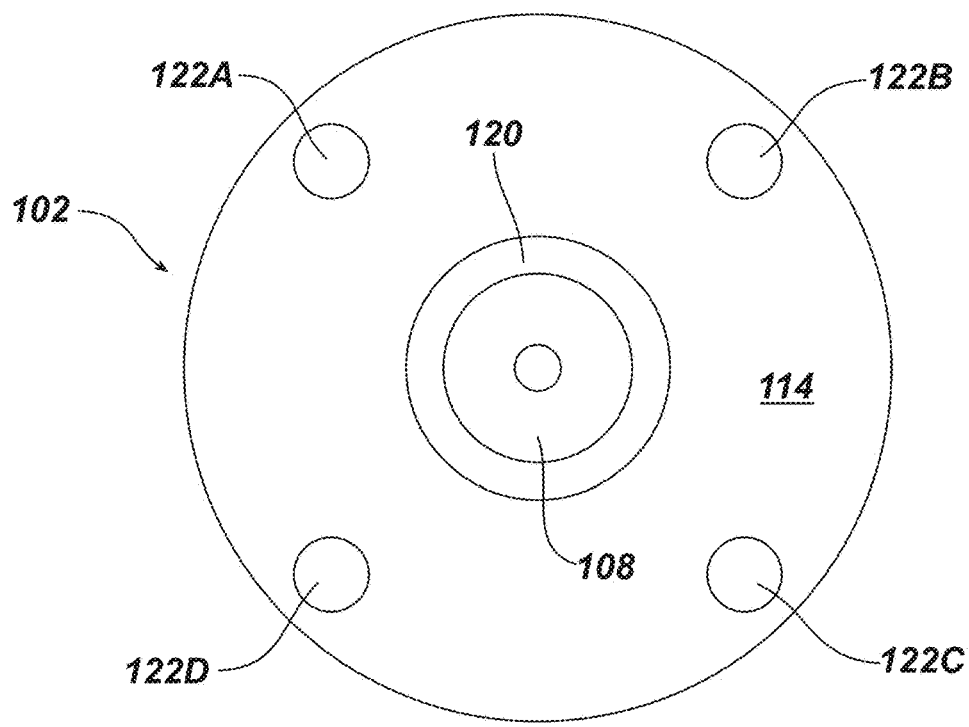
FIG. 8B is a proximal end view of the die body shown in FIG. 8A.

Referring to FIGS. 8A and 8B, in one embodiment, the die body 102 of the polymer extrusion die assembly 100 (FIGS. 6A-6B) preferably includes a top groove 120 having an annular shape that is formed in the top surface 114 of the die body and that surrounds the proximal opening 108 of the polymer extrusion die assembly. In one embodiment, the die body 102 desirably includes spaced alignment openings 122A-122D that are formed in the top surface 114 of the die body 102 for aligning the die body 102 with opposing tooling of a die assembly.

Figure 7A:
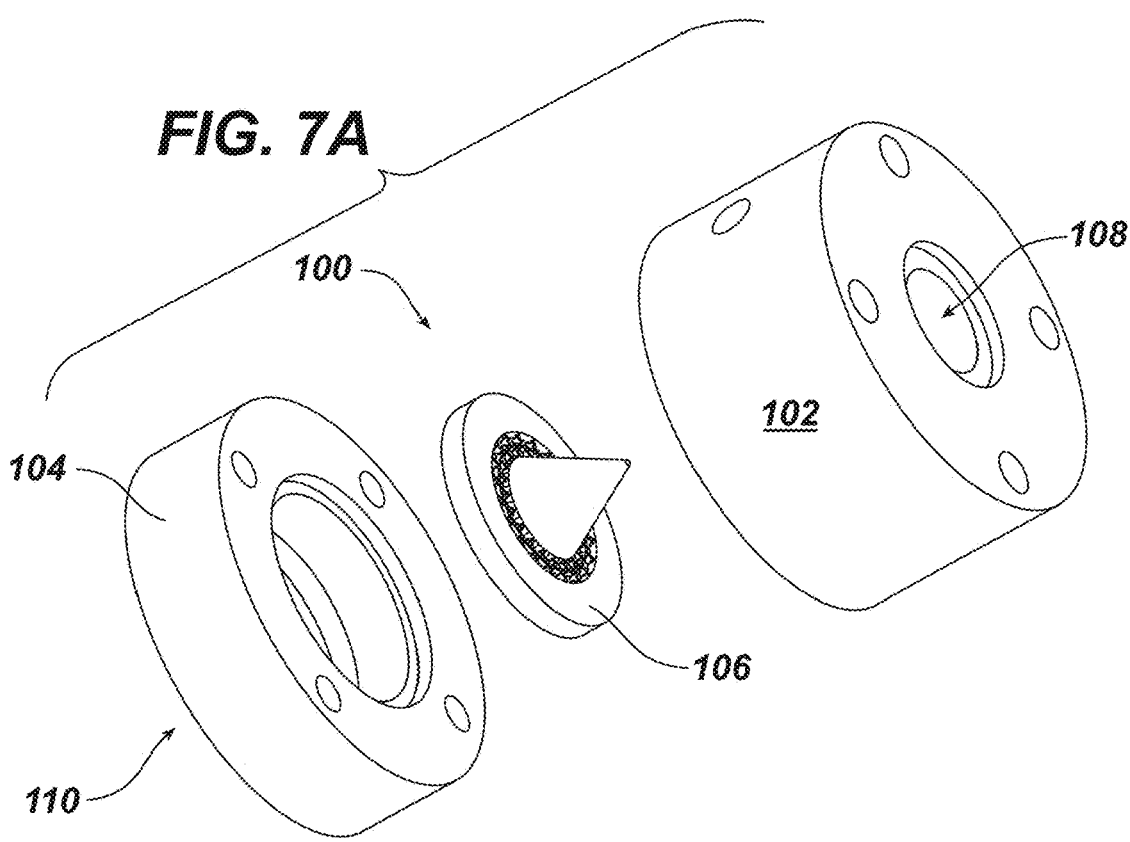
FIG. 7A is an exploded view of the polymer extrusion die assembly shown in FIGS. 6A and 6B, including the die body, the die retainer ring, and the spinneret.
Figure 7B:
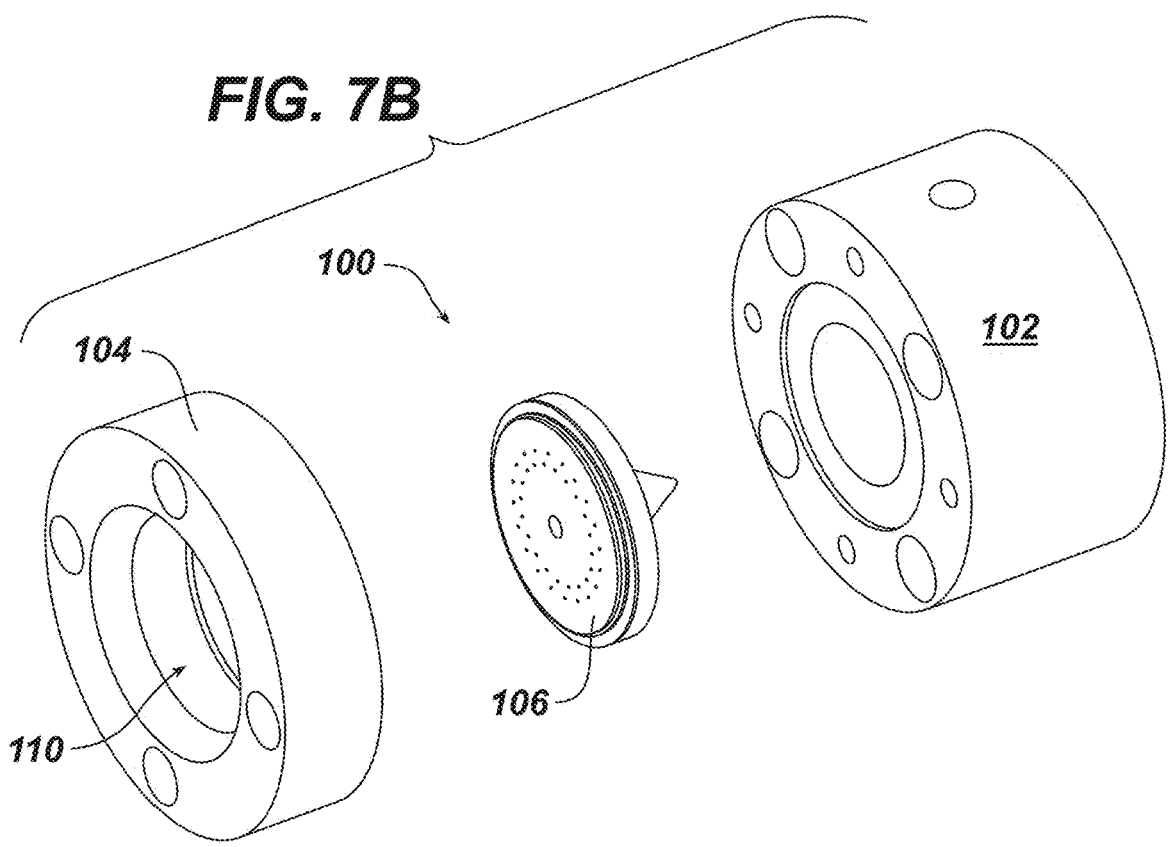
FIG. 7B is another exploded view of the polymer extrusion die assembly shown in FIGS. 6A-6B and 7A.
Figure 8C:
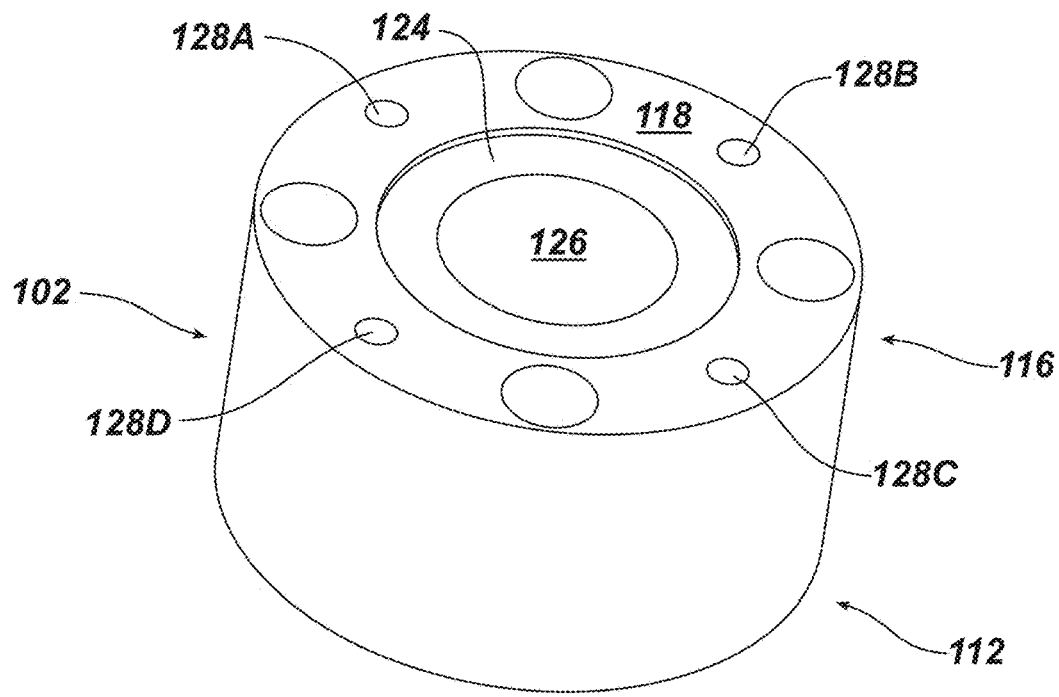
FIG. 8C is a perspective view of a distal end of the die body shown in FIGS. 8A and 8B.
Figure 8D:
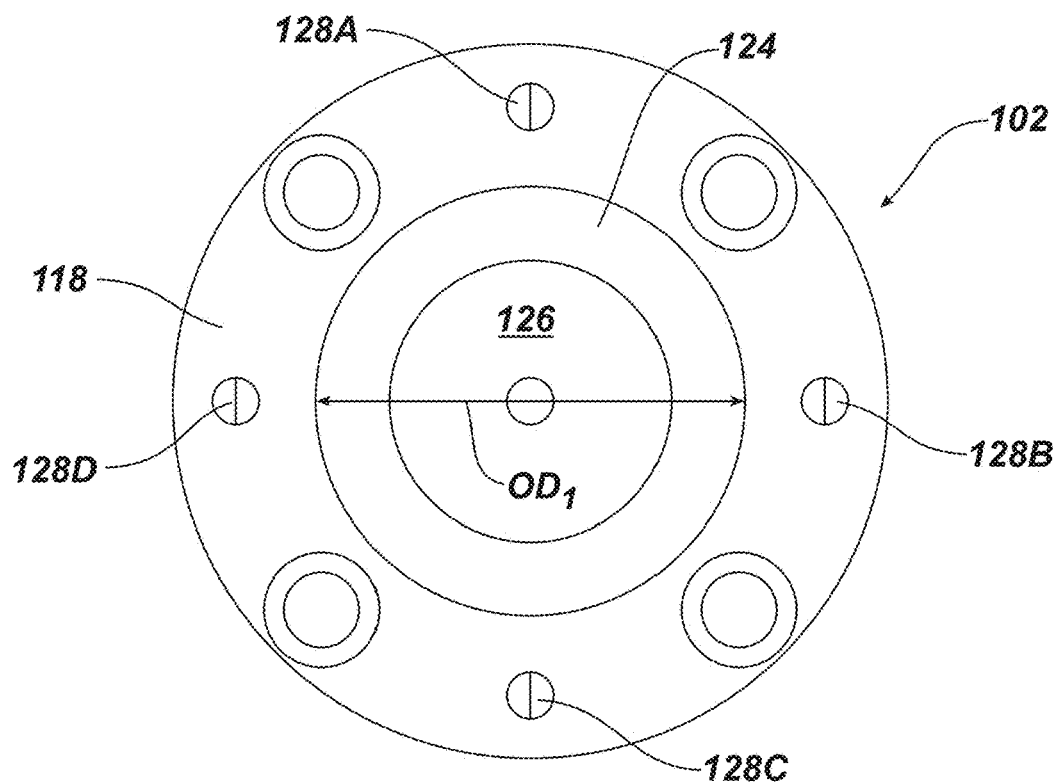
FIG. 8D is a distal end view of the die body shown in FIGS. 8A-8C.

Referring to FIGS. 8C and 8D, in one embodiment, the lower, trailing and/or distal end 116 of the die body 102 desirably includes the flat bottom surface 118, and a bottom groove 124 having an annular shape that is formed in the flat bottom surface 118 and that surrounds a polymer melt outlet opening 126. As will be described in more detail herein, the bottom annular groove 124 is sized and configured to seat a plate of the spinneret 106 (FIGS. 7A and 7B).

Figure 6A:
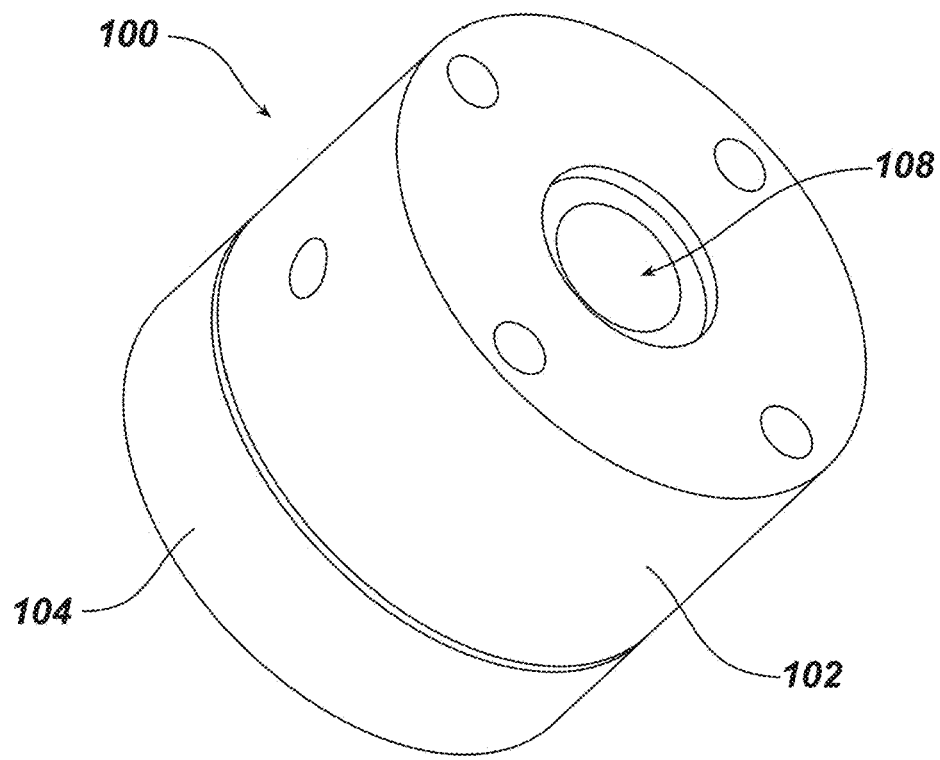
FIG. 6A is a perspective view of a proximal end of a polymer extrusion die assembly including a die body, a die retainer ring, and a spinneret, in accordance with one embodiment of the present patent application.
Figure 6B:
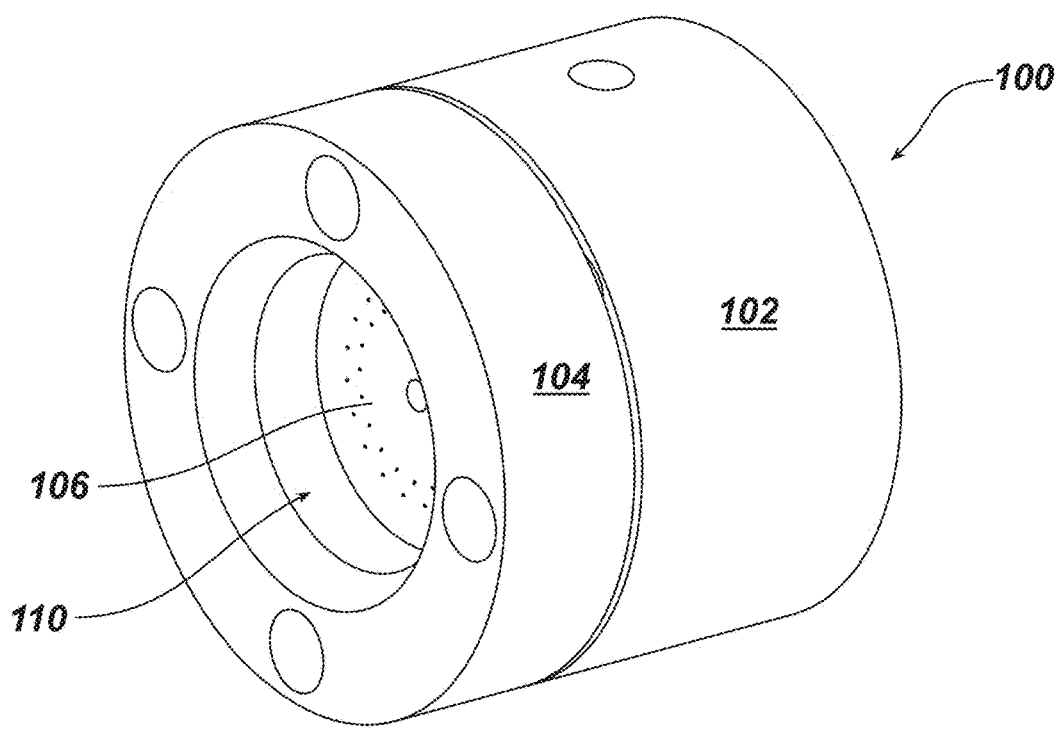
FIG. 6B is a perspective view of a distal end of the polymer extrusion die assembly shown in FIG. 6A including the die body, the die retainer ring, and the spinneret.

In one embodiment, the die body 102 preferably includes bolt holes 128A-128D that are formed in the flat bottom surface 118 of the die body 102, which are adapted to receive alignment bolts for aligning the die body 102 with the die retainer ring 104 (FIG. 6A).

Referring to FIG. 8D, in one embodiment, the bottom annular groove 124 of the die body 102 defines an outer diameter $OD_1$ that substantially matches an outer diameter of a plate of the spinneret 106 (FIG. 7A) that is assembled with the die body 102, as will be described in more detail herein. In one embodiment, the outer diameter $OD_1$ of the bottom annular groove 124 is preferably about 45-65 millimeters, more preferably about 50-60 millimeters, and even more preferably about 55-60 millimeters.

Figure 9A:
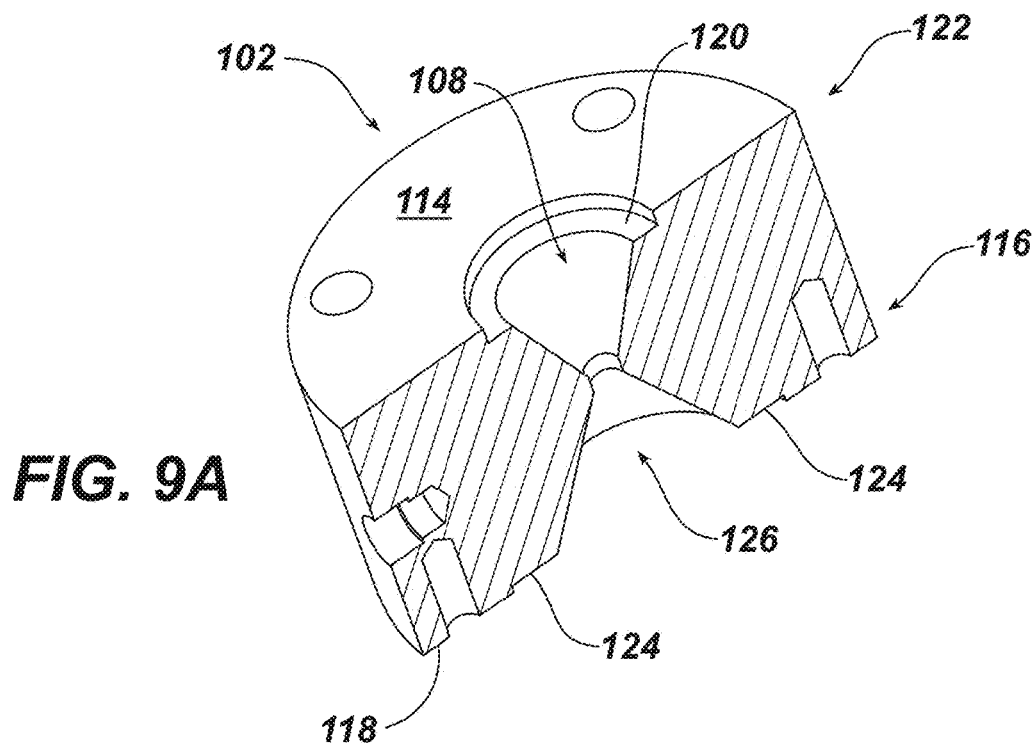
FIG. 9A is a cross-sectional view of the die body shown in FIGS. 8A-8D.
Figure 9B:
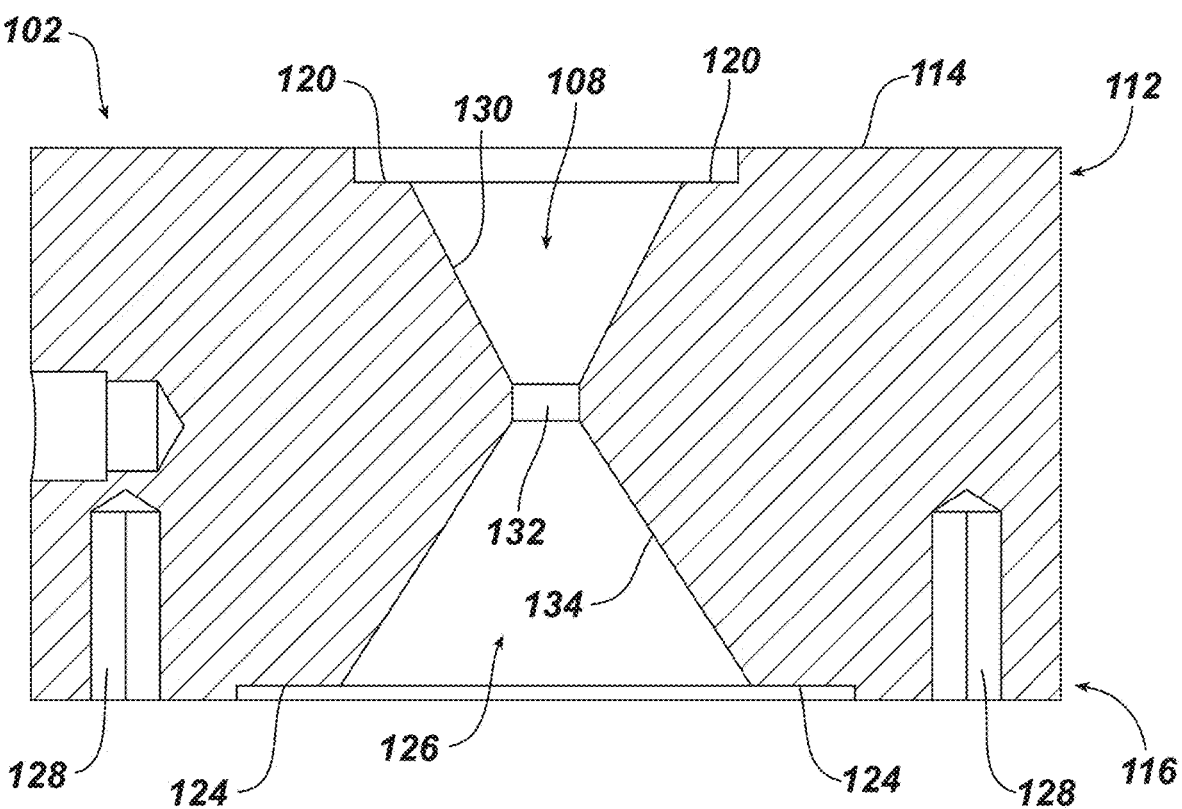
FIG. 9B is another cross-sectional view of the die body shown in FIGS. 8A-8D.
Figure 10A:
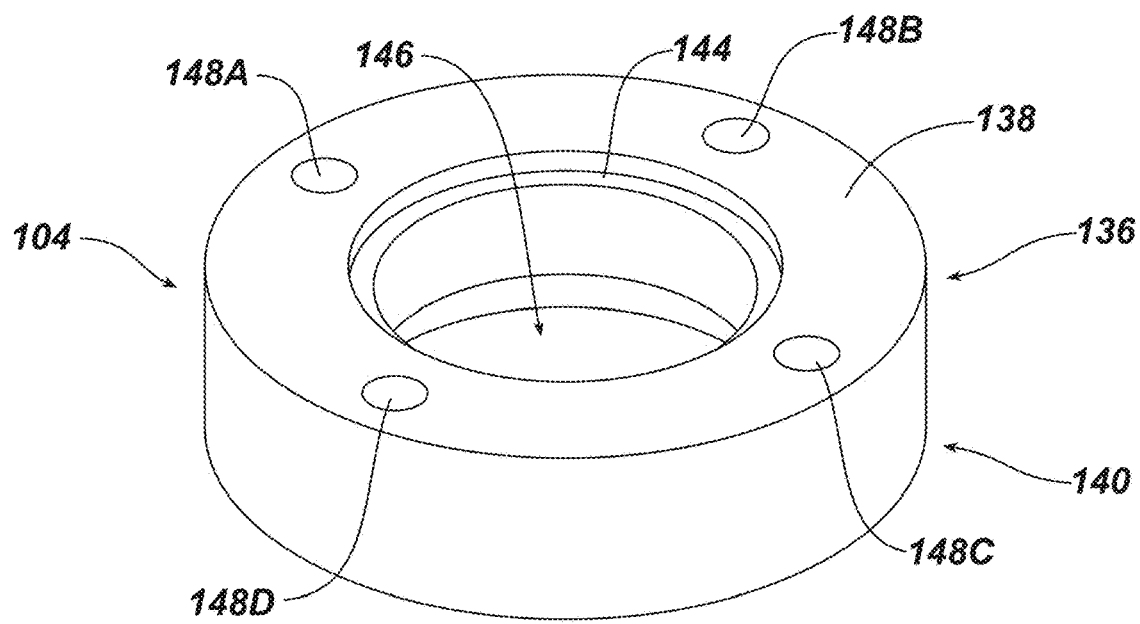
FIG. 10A is a perspective view of a proximal end of the die retainer ring shown in FIGS. 7A and 7B.
Figure 10B:
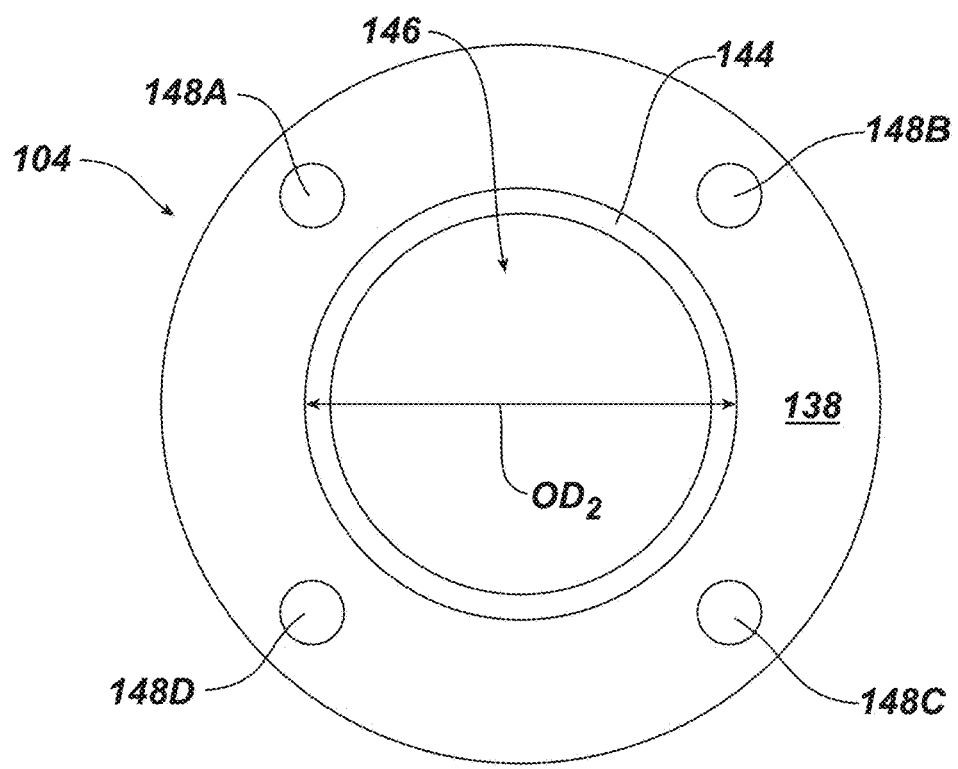
FIG. 10B is a proximal end view of the die retainer ring shown in FIG. 10A.
Figure 10C:
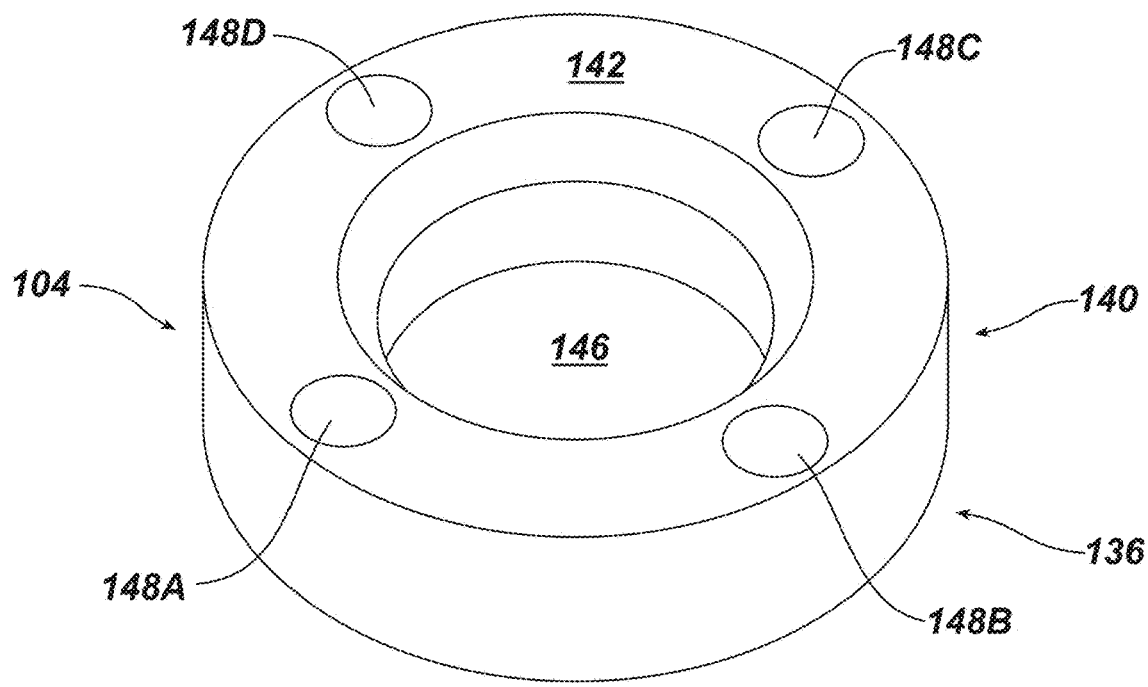
FIG. 10C is a perspective view of a distal end of the die retainer ring shown in FIGS. 10A and 10B.
Figure 10D:
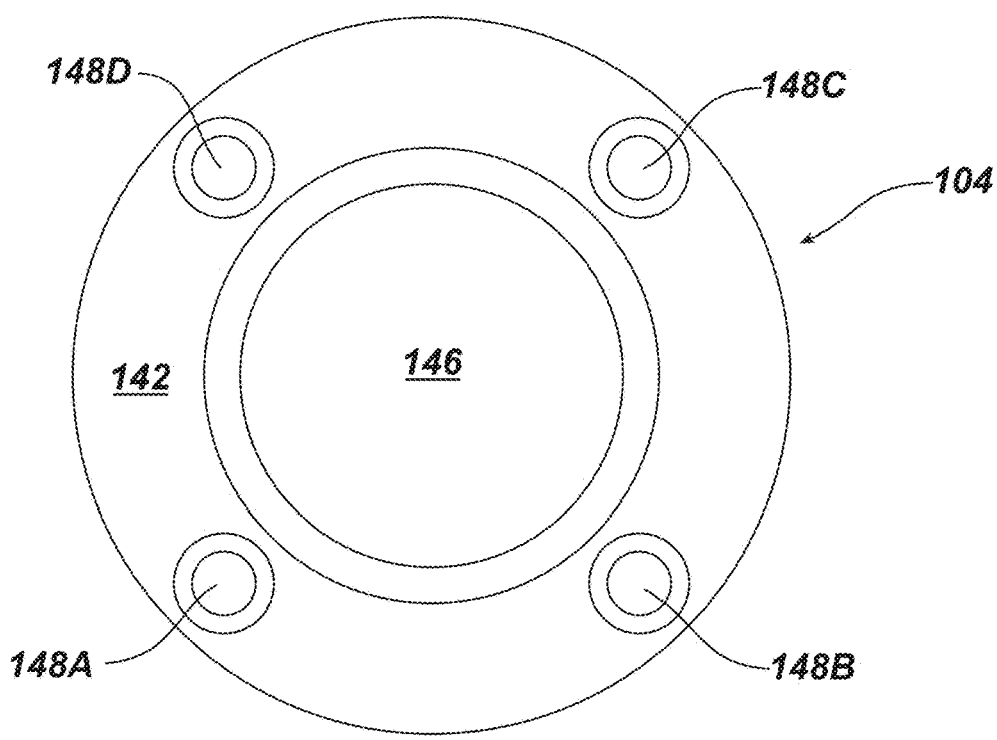
FIG. 10D is a distal end view of the die retainer ring shown in FIGS. 10A-10C.

Referring to FIGS. 9A and 9B, in one embodiment, the die body 102 preferably includes the proximal end 112 having the top flat surface 114 and the distal end 116 having the flat bottom surface 118. The die body 102 includes the top annular groove 120 that is formed in the flat top surface 114 and that surrounds the proximal opening 108 that is located at the upper end of the polymer extrusion die assembly 100 (FIG. 6A).

In one embodiment, the die body 102 desirably includes the bottom annular groove 124 that is formed in the flat bottom surface 118 of the die body 102 and that surrounds the polymer melt outlet opening 126 located at the distal end 116 of the die body 102. In one embodiment, the proximal opening 108 located at the upper end 112 of the die body 102 includes sloping side walls 130 that converge toward one another for defining an inverted cone that directs a polymer melt into a restricted flow area 132 of a polymer melt flow path. In one embodiment, the side walls 130 of the proximal opening 108 converge toward one another until they reach the restricted flow area 132 of the polymer melt flow path. In one embodiment, the polymer melt outlet opening 126 at the distal or lower end 116 of the die body 102 preferably includes sloping side walls 134 that slope outwardly away from one another between the restricted flow area 132 and the bottom annular groove 124 of the die body. The sloping side walls 134 of the polymer melt outlet opening 126 preferably define the shape of an upright cone that substantially matches the shape of a cone projecting above proximal surface of a plate of a spinneret that is inserted into the polymer melt outlet opening 126, as will be described in more detail herein. In one embodiment, the polymer melt outlet opening 126 has the shape of a hollow cone that is adapted to receive a conical projection of the spinneret 106 (FIG. 7B).

In one embodiment, the die body 102 includes the bottom bolt holes 128 that are formed in the flat bottom surface 118 of the die body 102 for receiving alignment bolts to align the die body 102 with the die retainer ring 104 (FIG. 6A), as will be described in more detail herein.

Referring to FIGS. 10A-10D, in one embodiment, the die retainer ring 104 of the polymer extrusion die assembly 100 (FIGS. 6A and 6B) preferably includes a top, leading and/or proximal end 136 having a flat top surface 138 and a bottom, trailing and/or distal end 140 having a flat bottom surface 142. In one embodiment, the die retainer ring 104 preferably includes a top annular groove 144 that is formed in the flat top surface 138 of the die retainer ring 104. The top annular groove 144 is sized and shaped to seat an alignment projection that extends from an underside of a plate of the spinneret 106 (FIG. 7A), as will be described in more detail herein.

In one embodiment, the die retainer ring 104 preferably includes a central opening 146 that extends from the flat top surface 138 to the flat bottom surface 142 of the die retainer ring. In one embodiment, the top annular groove 144 of the die retainer ring 104 surrounds the central opening 146. In one embodiment, the outer perimeter of the top annular groove 144 preferably defines a second outer diameter $OD_2$ that is less than the first outer diameter $OD_1$ of the bottom annular groove 124 at the lower end of the die body 102 (FIG. 8D). In one embodiment, the second outer diameter $OD_2$ of the top annular groove 144 of the die retainer ring 104 is sized to accommodate the alignment projection that extends from an underside of a plate of a spinneret for aligning the spinneret with the die retainer ring 104, as will be described in more detail herein. In one embodiment, when the spinneret plate is seated within the top annular groove 144 of the die retainer ring 104, the distal ends of the capillary openings at an underside of the spinneret plate are preferably surrounded by the top annular groove 144 of the die retainer ring 104 whereby polymer fibers extruded from the capillary openings of the spinneret plate pass through the central opening 146 of the die retainer ring 104.

In one embodiment, the die retainer ring 104 preferably includes spaced bolt holes 148A-148D that are adapted to receive alignment bolts for aligning the die retainer ring 104 with the die body 102 (FIG. 7A). In one embodiment, an alignment bolt may be inserted through each of the spaced bolt holes 148A-148D.

Figure 11A:
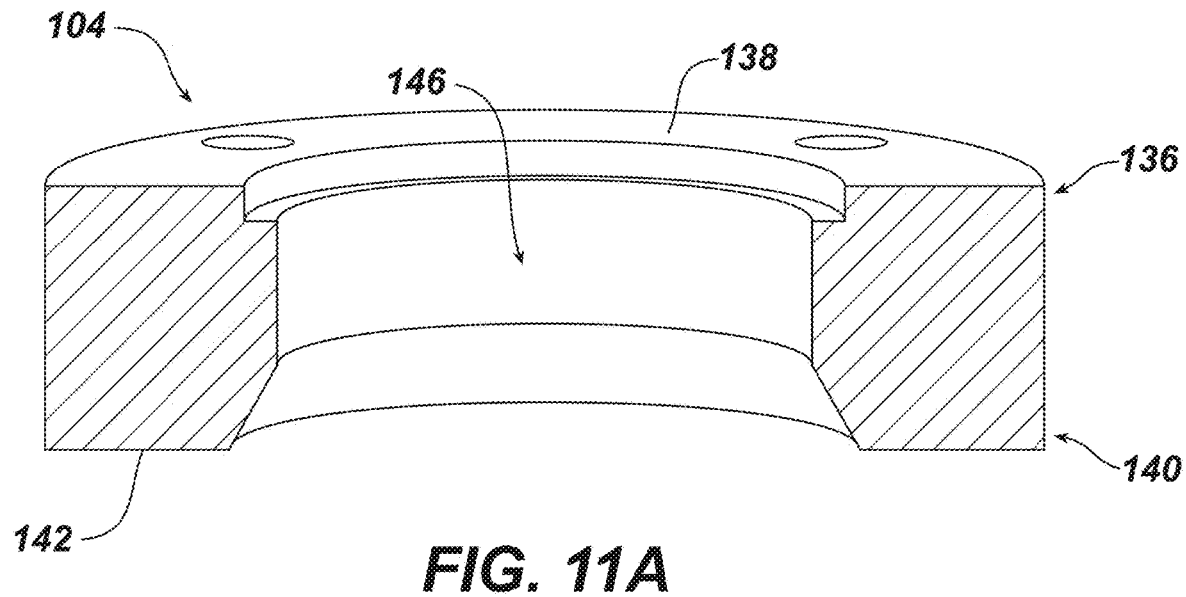
FIG. 11A is a cross-sectional view of the die retainer ring shown in FIGS. 10A-10D.
Figure 11B:
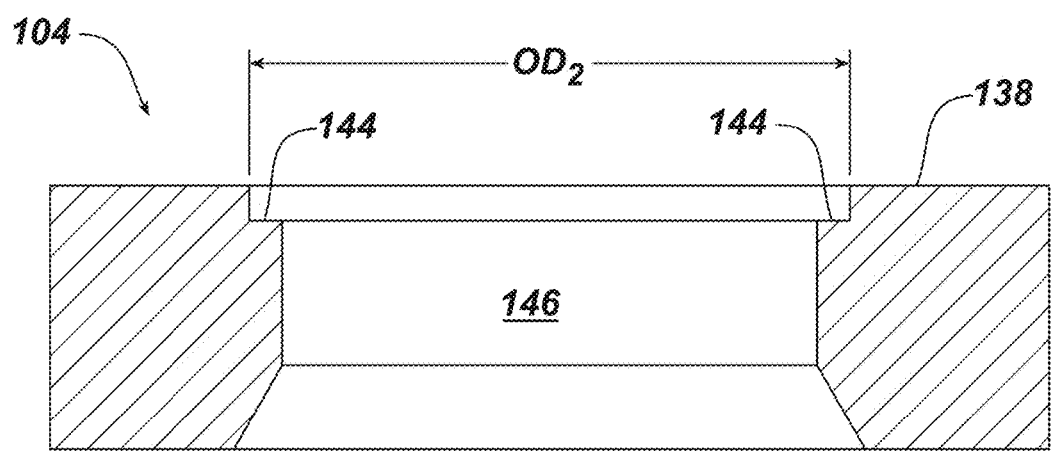
FIG. 11B is another cross-sectional view of the die retainer ring shown in FIGS. 10A-10D.

Referring to FIGS. 11A and 11B, in one embodiment, the die retainer ring 104 desirably includes the proximal end 136 having the flat top surface 138 and the distal end 140 having the flat bottom surface 142. The top annular groove 144 is formed in the flat top surface 138 of the die retainer ring 104. The central opening 146 preferably extends through the center of the die retainer ring 104 from the flat top surface 138 at the proximal end 136 of the die retainer ring 104 to the flat bottom surface 142 at the distal end 140 of the die retainer ring 104.

Referring to FIG. 11B, in one embodiment, the top annular groove 144 formed in the flat top surface 138 of the die retainer ring 104 preferably defines the second outer diameter $OD_2$ that matches an outer diameter of an alignment projection that extends from an underside of a plate of the spinneret 106 (FIG. 7A) for aligning the spinneret with the central opening 146 of the die retainer ring 104. The top annular groove 144 functions as a seat for the underside or distal side of the plate of the spinneret for preventing the plate of the spinneret from shifting and/or moving relative to the die retainer ring 104.

Referring to FIGS. 12A-12D, in one embodiment, the spinneret 106 (FIG. 7A), also commonly referred to as a die, preferably includes a plate 150 having a top or proximal surface 152 and a bottom or distal surface 154. In one embodiment, the plate 150 preferably has an outer perimeter 156 that defines an outer diameter $OD_3$ that substantially matches the outer diameter $OD_1$ of the bottom annular groove 124 of the die body 102 (FIG. 8D) for assembling the spinneret with the lower or distal end of the die body. The plate 150 may have annular or circular shape, however, in other embodiments, the plate may have a square or rectangular shape, or have one or more flat sides.

Figure 12A:
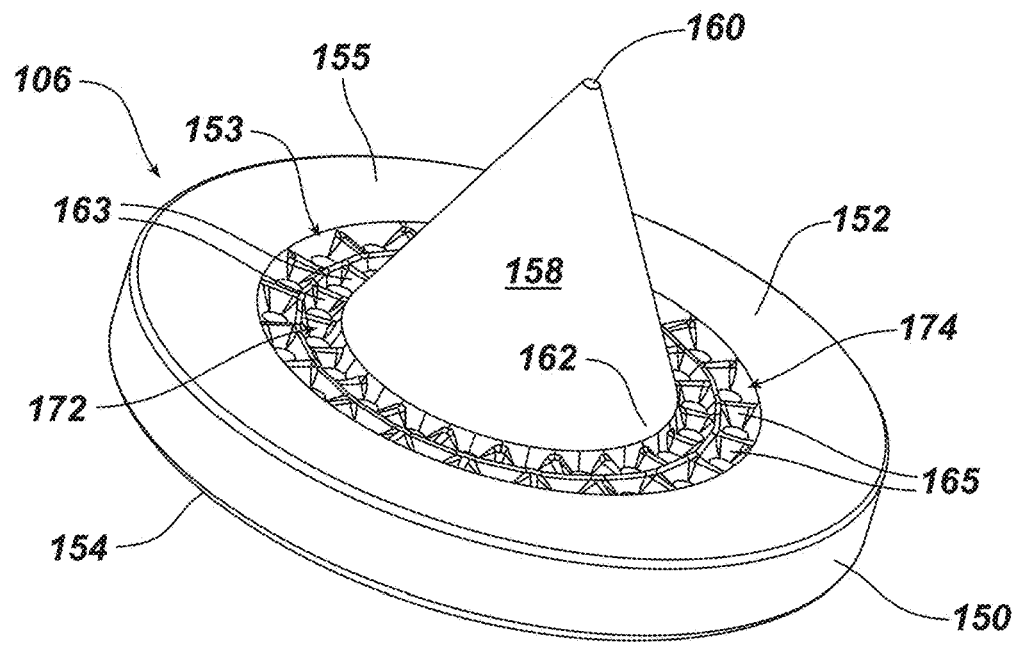
FIG. 12A is a perspective of a proximal side of the spinneret shown in FIGS. 7A and 7B.
Figure 12B:
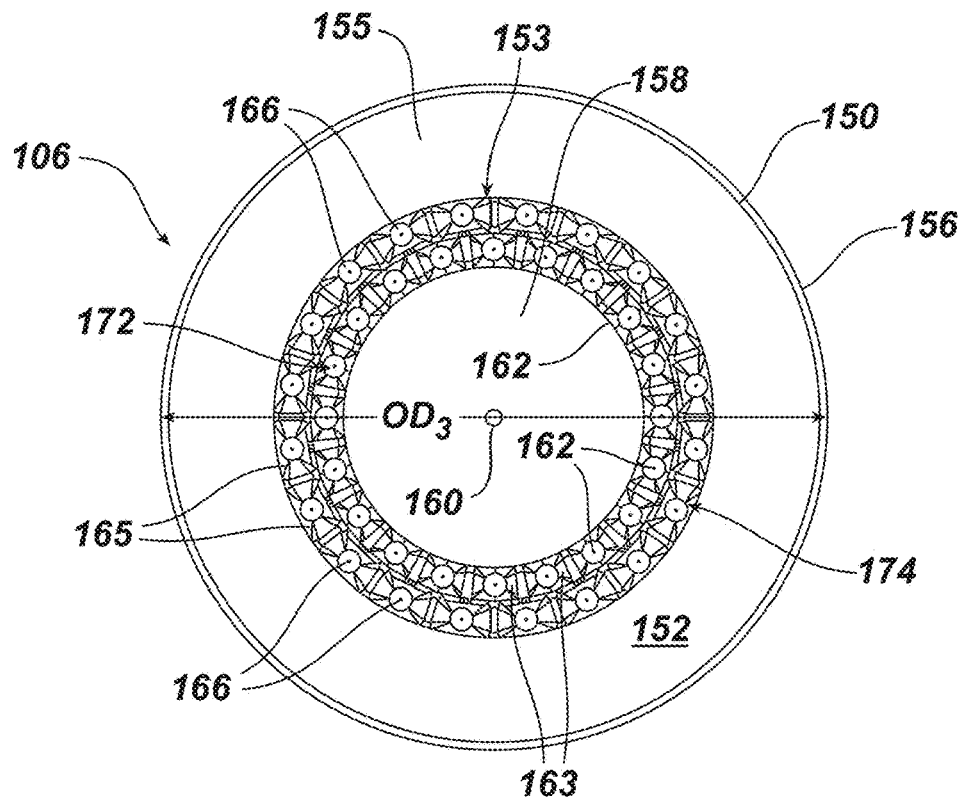
FIG. 12B is a top or proximal side view of the spinneret shown in FIG. 12A.

Referring to FIGS. 12A and 12B, in one embodiment, the spinneret 106 preferably includes a cone 158 that projects above the proximal surface 152 of the plate 150. The cone 158 desirably includes an apex 160 that is adapted to be inserted into the polymer melt outlet opening 126 located at the distal end of the die body 102 (FIG. 9B). The cone 158 preferably includes a base 162 at a lower end thereof that is in substantial alignment with a plane defined by the proximal surface 152 of the plate 150.

In one embodiment, the proximal surface 152 of the spinneret plate 150 preferably includes a wetted area 153 and a sealed area 155 that surrounds the wetted area 153. In one embodiment, the wetted area 153 of the proximal surface 152 of the plate 150 is the area of the plate 150 that comes in contact with the polymer melt as the polymer melt is extruded through the spinneret 106. The sealed area 155 of the proximal surface 152 is preferably an area of the plate that is assembled between the components of the polymer extrusion die assembly and does not come in contact with the polymer melt as it flows through the polymer extrusion die assembly. In one embodiment, the wetted area 153 of the proximal surface 152 of the plate 150 preferably surrounds the base 162 of the cone 158, and the sealed area 155 of the proximal surface 152 of the plate 150 preferably surrounds the wetted area 153.

Referring to FIGS. 12A and 12B, in one embodiment, the wetted area 153 of the proximal surface 152 of the plate 150 preferably includes an inner ring 172 that contains inner contoured entrance zones 163 that are in communication with proximal ends of inner holes 164 that are formed in the plate 150. In one embodiment, the inner ring 172, the inner contoured entrance zones 163, and the inner holes 164 are arrayed in an annular configuration. The inner holes 164 preferably extend from distal ends of the respective inner contoured entrance zones 163 toward the distal surface or underside of the plate 150 for passing a polymer melt through the plate.

In one embodiment, the wetted area 153 of the proximal surface 152 of the plate 150 preferably includes an outer ring 174 that contains outer contoured entrance zones 165 that are in communication with proximal ends of outer holes 166 that are formed in the plate 150. In one embodiment, the outer ring 174, the outer contoured entrance zones 165, and the outer holes 166 are arrayed in an annular configuration. The outer holes 166 preferably extend from the respective distal ends of the outer contoured entrance zones 165 toward the distal surface or underside of the plate 150 for extruding the polymer melt through the plate.

In one embodiment, inner ring 172 preferably surrounds the base 162 of the cone 158, whereby inner contoured entrance zones 163 and the inner holes 164 are located within the inner ring 172. In one embodiment, the outer ring 174 surrounds the inner ring 172, whereby the outer contoured entrance zones 165 and the outer holes 166 are located within the outer ring 174. In one embodiment, the inner and outer rings 172, 174 define the wetted area 153 of the proximal surface 152 of the plate 150, and the sealed area 155 of the proximal surface 152 of the plate 150 surrounds the wetted area 153.

Figure 12C:
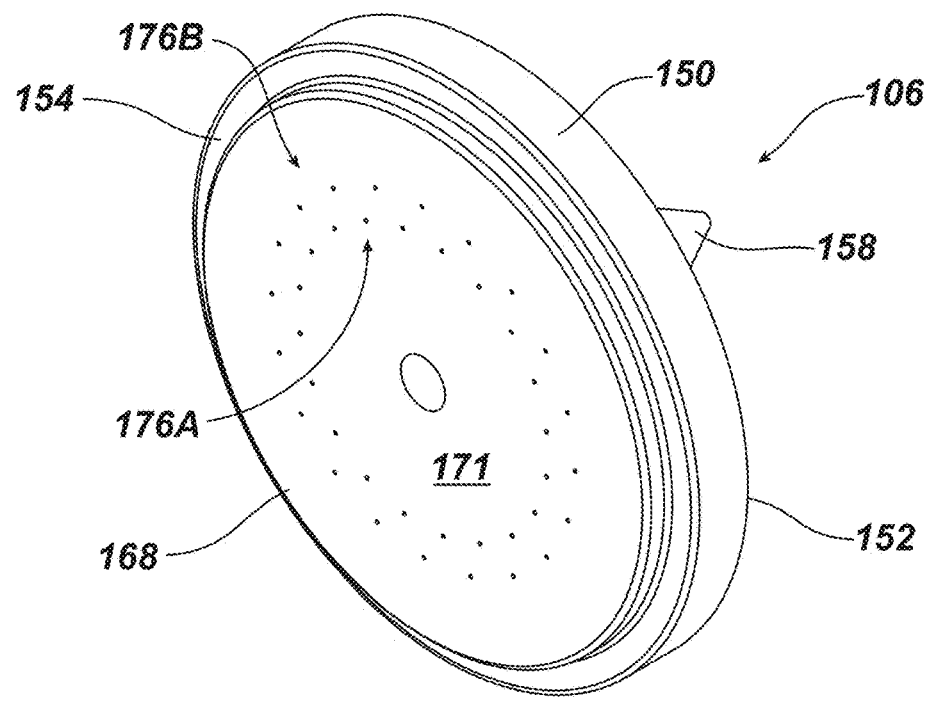
FIG. 12C is a perspective view of a distal side of the spinneret shown in FIGS. 12A and 12B.
Figure 12D:
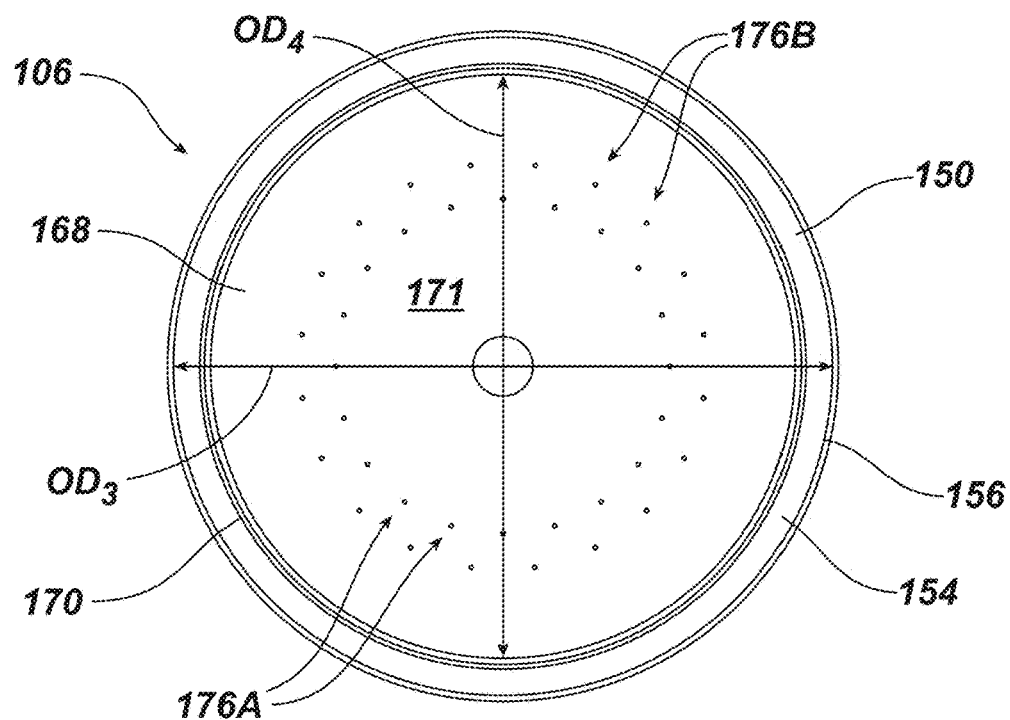
FIG. 12D is a bottom or distal side view of the spinneret shown in FIGS. 12A-12C.

Referring to FIGS. 12C and 12D, in one embodiment, the spinneret 106 preferably includes an alignment projection 168 that extends below and/or projects from the underside or distal surface 154 of the plate 150. In one embodiment, the alignment projection 168 has an outer perimeter 170 with a circular configuration that is concentric with the outer perimeter 156 of the plate 150 of the spinneret 106. In one embodiment, the outer perimeter 170 of the alignment projection 168 preferably defines an outer diameter $OD_4$ that is less than the outer diameter $OD_3$ of the plate 150. In one embodiment, the outer diameter $OD_4$ defined by the outer perimeter 170 of the alignment projection 168 preferably matches the second outer diameter $OD_2$ of the top annular groove 144 formed in the top surface 138 of the die retainer ring 104 (FIG. 11B). The matching diameters enable the alignment projection of the spinneret plate to be seated within the top annular groove of the die retainer ring.

In one embodiment, the alignment projection 168 has a bottom or distal surface 171. In one embodiment, the spinneret 106 preferably includes inner capillary holes 176A that are formed in the distal surface 171, which have proximal ends that are in communication with distal ends of the respective inner holes 164 (FIGS. 12A and 12B), and outer capillary holes 176B that are formed in the distal surface 171, which have proximal ends that are in communication with distal ends of the respective outer holes 166 (FIGS. 12A and 12B). In one embodiment, the polymer melt that is forced into the inner and outer holes of the plate is extruded as fibers through the respective inner and outer capillary holes 176A, 176B. In one embodiment, the inner and outer capillary holes 176A, 176B are preferably spaced from one another in a ring-shaped pattern that matches the spacing pattern of the inner and outer holes 164, 166 (FIGS. 12A and 12B).

Figure 13A:
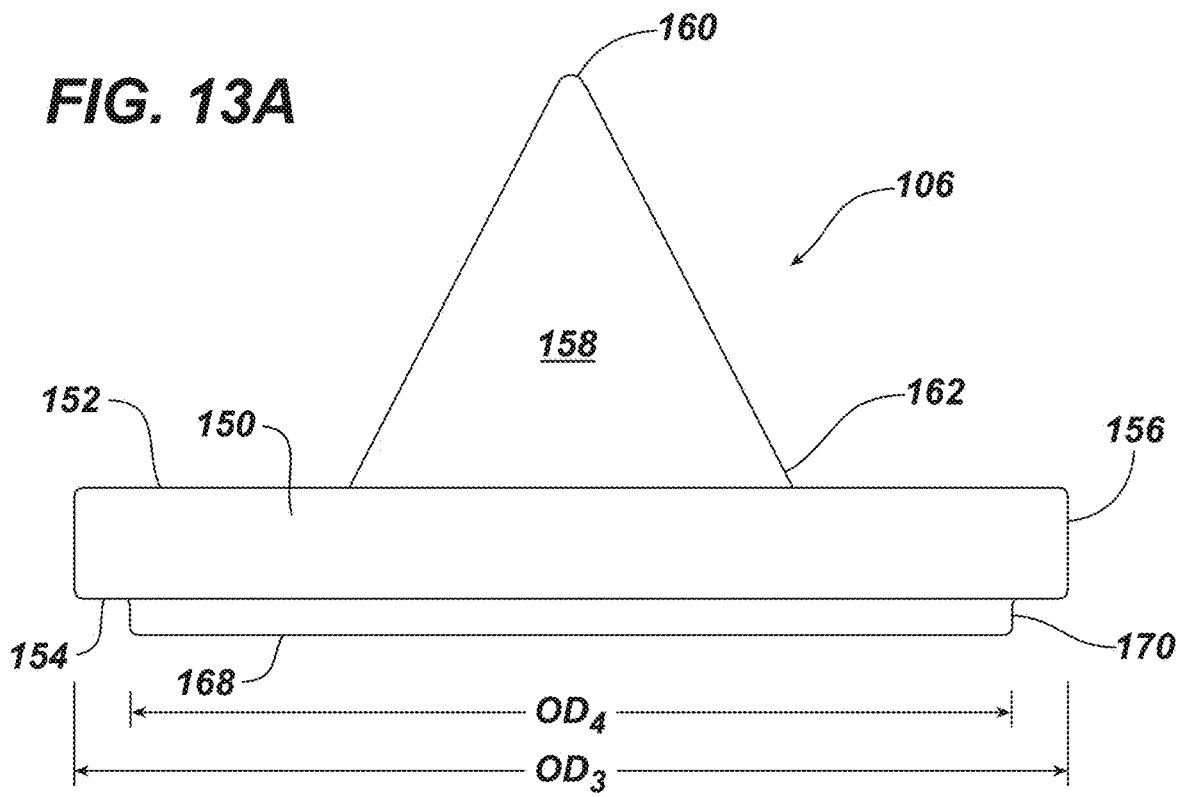
FIG. 13A is a side elevation view of the spinneret shown in FIGS. 12A-12D.
Figure 13B:
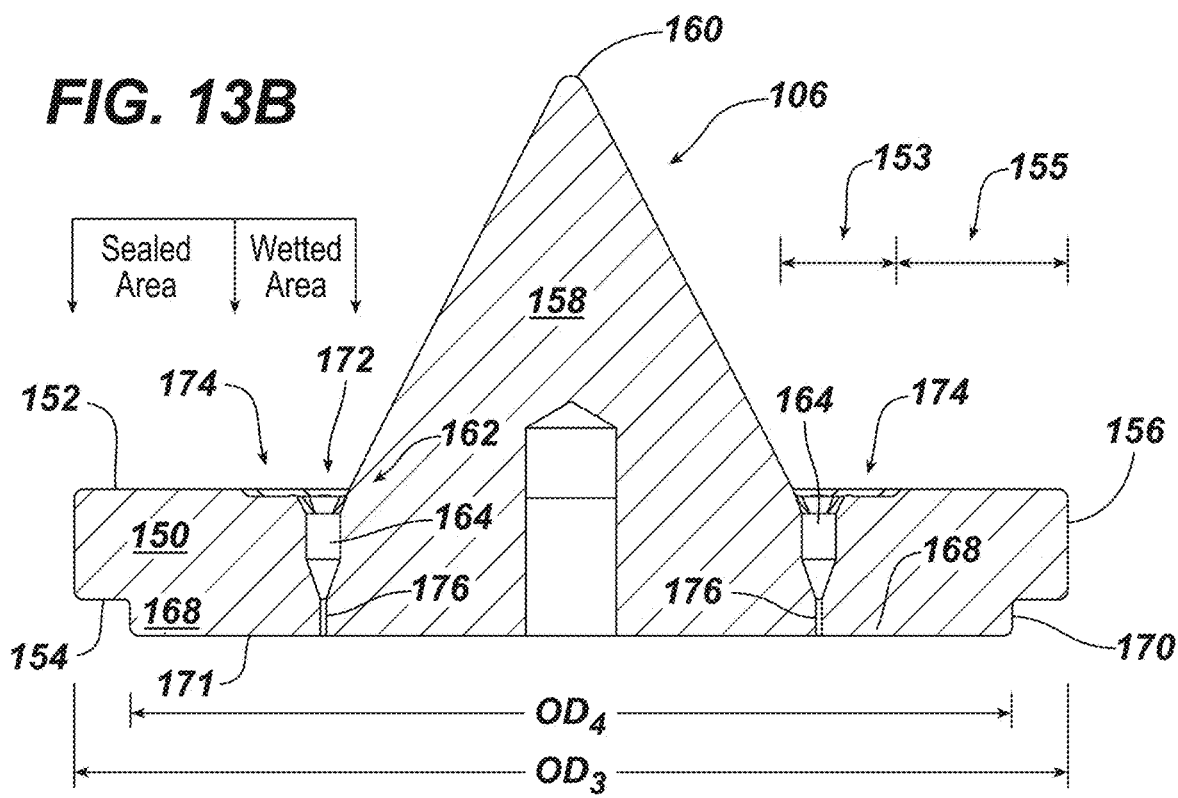
FIG. 13B is a cross-sectional view of the spinneret shown in FIGS. 12A-12D and 13A.

Referring to FIGS. 13A and 13B, in one embodiment, the spinneret 106 preferably includes the plate 150 having the proximal surface 152 and the distal surface 154. The plate 150 preferably has the outer perimeter 156 that defines the outer diameter $OD_3$ of the plate 150, which matches the size and shape of the bottom annular groove formed at the lower or distal end of the die body.

In one embodiment, the alignment projection 168 that projects from the underside of the plate 150 preferably extends from the distal surface 154 of the plate 150. The alignment projection 168 desirably includes an outer perimeter 170 that defines an outer diameter $OD_4$ that is less than the outer diameter $OD_3$ of the plate 150. The outer diameter $OD_4$ of the alignment projection 168 preferably matches the size and shape of the top annular groove formed at the upper or proximal end of the die retainer ring.

In one embodiment, the spinneret 106 includes the cone 158 that projects above the proximal surface 152 of the plate 150. In one embodiment, the proximal surface 152 of the plate 150 is a flat or planar surface, and may extend in a horizontal plane. The cone 158 includes the apex 160 and the base 162 having a lower end that is in substantial alignment with a plane defined by the proximal surface 152 of the plate 150.

Referring to FIG. 13B, in one embodiment, the proximal surface 152 of the plate 152 preferably includes the wetted area 153 and the sealed area 155 that surrounds the wetted area 153. In one embodiment, the inner and outer rings 172, 174 are located within the wetted area 153 of the proximal surface 152 of the plate, and the sealed area extends from the outer perimeter of the outer ring 174 to the outer perimeter 156 of the plate 150. In one embodiment, the spinneret 106 preferably includes the inner ring 172 formed in the wetted area 153 of the proximal surface 152, whereby the inner contoured entrance zones 163, the inner holes 164 and the inner capillaries 176A are associated with the inner ring 172. In one embodiment, the spinneret 106 preferably includes the outer ring 174, also formed in the wetted area 153 of the proximal surface 152, whereby the outer contoured entrance zones 165, the outer holes 166 and the outer capillaries 176B (FIG. 12D) are associated with the outer ring 174. In one embodiment, the inner and outer rings 172, 174 are concentric and preferably have an annular or ring shape. The spinneret 106 preferably includes the capillary holes 176A and 176B (FIG. 12D) that are formed in the distal surface 171 of the alignment projection 168. The capillary holes 176A and 176B (FIG. 12D) are preferably in communication with distal ends of the respective inner and outer holes 164, 166 (FIG. 12B) that are formed in the plate 150.

Figure 14A:
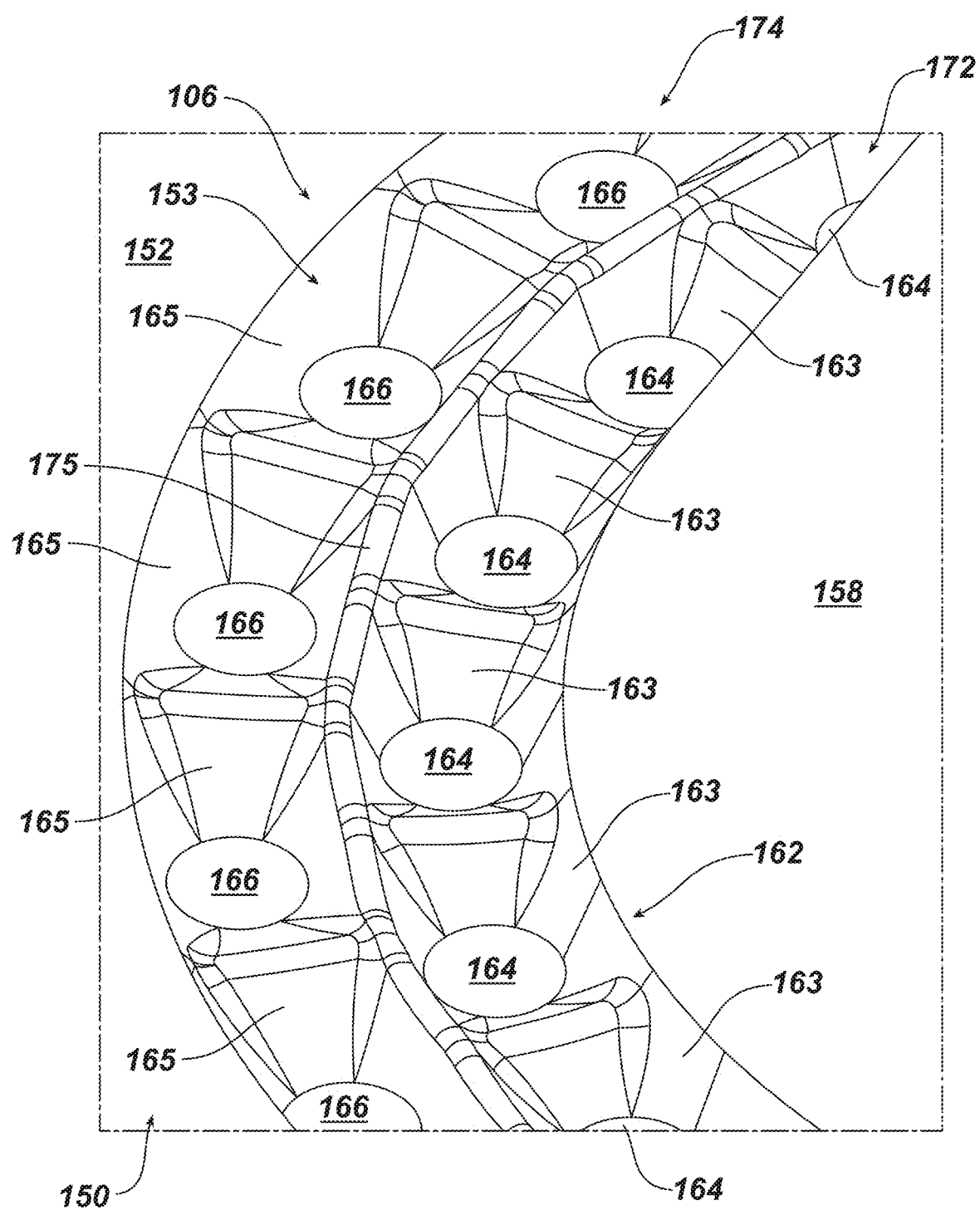
FIG. 14A is a perspective view of a section of the proximal side of the spinneret shown in FIGS. 12A and 12B with holes passing through a plate of the spinneret, in accordance with one embodiment of the present patent application.

Referring to FIG. 14A, in one embodiment, the proximal surface 152 of the plate 150 (FIG. 13B) of the spinneret 106 preferably includes the wetted area 153 that contains the inner ring 172 and the outer ring 174. The inner ring 172 preferably has an annular shape and surrounds the outer perimeter of the base 162 of the cone 158 that projects above the proximal surface 152 of the plate 150. In one embodiment, the inner contoured entrance zones 163 for each inner hole 164 are formed in the inner ring 172. The inner contoured entrance zones 163 preferably extend below or distal to the proximal surface 152 of the plate for being in communication with proximal ends of the respective inner holes 164. In one embodiment, the inner holes 164 are preferably located within the inner ring 172. The inner holes may be drilled. The inner holes 164 are preferably spaced from one another and have an array pattern that matches the annular shape of the inner ring 172. The inner holes 164 preferably extend toward and are in communication with the respective inner capillary holes 176A (FIG. 12C) that are formed in the bottom or distal surface 171 of the alignment projection 168 (FIG. 13B). Lower or distal ends of the inner holes 164 preferably intersect with upper or proximal ends of the respective inner capillary holes 176A (FIG. 12C) for directing the polymer melt into the inner capillary holes.

In one embodiment, the inner ring 172 preferably includes the inner contoured entrance zones 163 that extend to the proximal ends of the inner holes 164 so that within the wetted area 153 there are substantially no flat or planar surfaces normal to the direction of the central axes of the distal ends of the holes, and/or that are parallel with the flat, proximal surface 152 of the plate of the spinneret 106. In one embodiment, an inner contoured entrance zone 163 preferably surrounds the proximal end of each inner hole 164 that is formed in the plate. In one embodiment, each contoured entrance zone 163 preferably includes contoured surfaces that extend distally from the proximal surface 152 of the plate 150 (FIG. 13B) to the proximal end of one of the inner holes 164.

In one embodiment, within the inner ring 172, the inner contoured entrance zone 163 surrounding the proximal end of each inner hole 164 directly borders the inner contoured entrance zone 163 surrounding the proximal end of each adjacent inner hole 164 so that there are substantially no planar surfaces normal to the direction of the central axis of the distal ends of the holes that remain between adjacent holes on the proximal surface 152 of the spinneret plate 150. The contoured surfaces of the inner contoured entrance zones 163 located around the inner holes 164 may include sloping surfaces, and curved surfaces including concave curved surfaces and convexly curved surfaces. In one embodiment, a border 175 that extends between the inner and outer rings 172, 174 may have a convexly curved surface that is substantially devoid of any flat or planar surfaces that are normal to the direction of the central axes of the distal ends of the respective holes and/or that are parallel with the flat, proximal surface 152 of the spinneret plate. In one embodiment, the border 175 is located in the wetted area and may be distal to and/or located below the proximal surface 152 of the plate 150.

In one embodiment, the outer ring 174 is also located within the wetted area 153 of the proximal surface 152 of the plate 150 of the spinneret 106. The outer ring 174 preferably has an annular shape and surrounds the inner ring 172. In one embodiment, the outer contoured entrance zones 165 for each outer hole 166 are formed in the outer ring 174. The outer contoured entrance zones 165 preferably extend below or distal to the proximal surface 152 of the plate for being in communication with proximal ends of the respective outer holes 166. In one embodiment, the outer holes 166 are preferably located within the outer ring 174. The outer holes may be drilled. The outer holes 166 are preferably spaced from one another and have an array pattern that matches the annular shape of the outer ring 174. The outer holes 166 preferably extend toward the respective outer capillary holes 176B (FIG. 12D) formed in the bottom or distal surface 171 of the alignment projection 168 (FIG. 13B). Lower or distal ends of the outer holes 166 preferably intersect with upper or proximal ends of the respective outer capillary holes 176B (FIG. 12D) for directing the polymer melt into the outer capillary holes.

In one embodiment, the outer ring 174 preferably includes the outer contoured entrance zones 165 that are proximal to proximal ends of the outer holes 166 so that within the wetted area 153 there are no flat or planar surfaces that are normal to the direction of the central axes of the distal ends of the holes and/or that are parallel with the flat, proximal surface 152 of the plate of the spinneret 106. In one embodiment, an outer contoured entrance zone 165 preferably surrounds the proximal end of each outer hole 166 that is formed in the plate. In one embodiment, each outer contoured entrance zone 165 preferably includes contoured surfaces that extend distally from the proximal surface 152 of the plate 150 (FIG. 13B) to the proximal end of one of the outer holes 166.

In one embodiment, within the outer ring 174, the outer contoured entrance zone 165 surrounding the proximal end of each outer hole 166 directly borders the outer contoured entrance zone 165 surrounding the proximal end of each adjacent outer hole 166 so that no planar surfaces normal to the direction of the central axes of the distal ends of the respective holes remain between adjacent holes on the proximal surface 152 of the spinneret plate 150. The contoured surfaces of the outer contoured entrance zones 165 that extend around the outer holes 166 may include sloping surfaces, and curved surfaces including concave curved surfaces and convexly curved surfaces. In one embodiment, the border 175 extends between the inner and outer rings 172, 174, and may have a convexly curved surface that is devoid of any flat surfaces that are parallel with the flat, proximal surface 152 of the spinneret plate 150, thereby eliminating dead areas from the proximal surface of the spinneret plate.

Figure 14B:
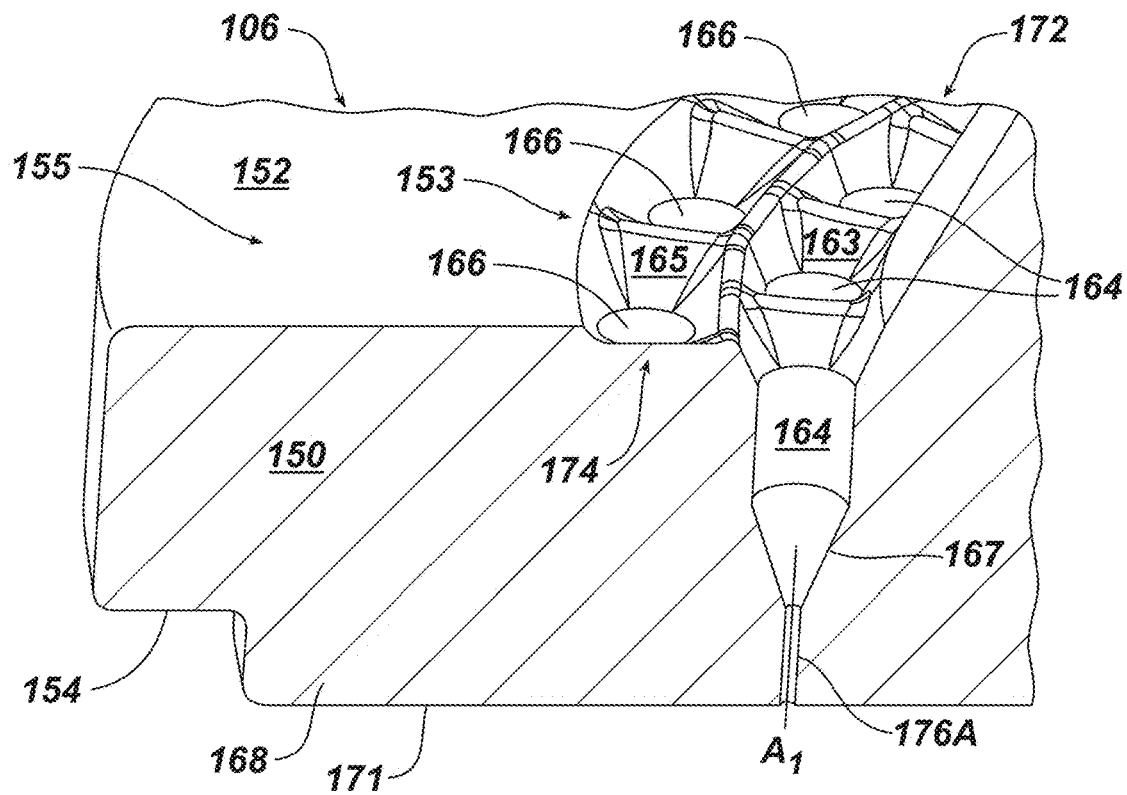
FIG. 14B is a cross-sectional view of a section of the spinneret shown in FIG. 14A.
Figure 14C:
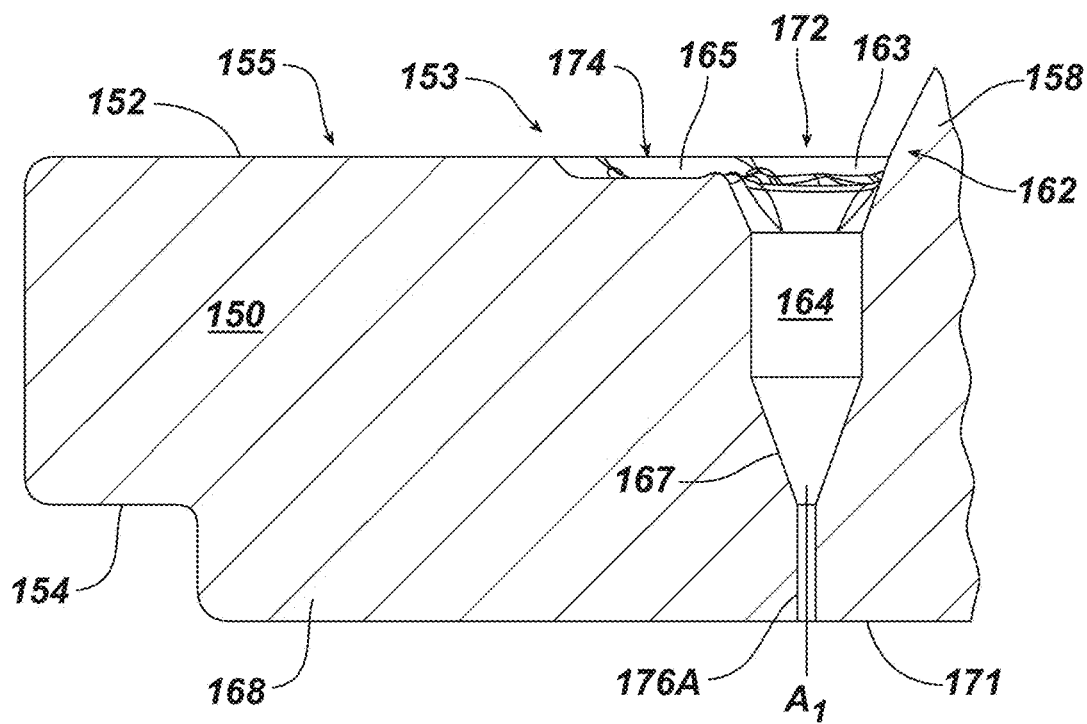
FIG. 14C is a side view of the cross-sectional view of a section of the spinneret shown in FIG. 14B.

Referring to FIGS. 14B and 14C, in one embodiment, the inner ring 172 and the outer ring 174 are formed in the wetted area 153 of the proximal surface 152 of the plate 150 of the spinneret 106. In one embodiment, the inner and outer rings 172, 174 are recessed and/or located below the proximal surface 152 of the plate 150 (FIG. 12A) of the spinneret 106.

In one embodiment, the spinneret 106 preferably includes the inner contoured entrance zones 163, the inner holes 164, and the inner capillary holes 176A that are associated with the inner ring 172. In one embodiment, distal ends of the inner contoured entrance zones 163 are in communication with proximal ends of the respective inner holes 164, and distal ends of the inner holes 164 preferably include conical sections 167 that are in communication with proximal ends of the respective inner capillary holes 176A. Thus, the inner diameters of the inner holes 164 taper inwardly at the conical sections 167 to match the inner diameters of the inner capillary holes 176A. Each inner capillary hole 176A preferably has a central axis $A_1$ that extends along the length of the inner capillary hole 176A. In one embodiment, the central axis $A_1$ of the inner capillary hole 176A is preferably normal to the flat, planar surface 152 of the plate 150.

In one embodiment, a polymer melt is forced into the inner contoured entrance zones 163 located within the inner ring 172, whereupon the polymer melt flows in series over the contoured surfaces of the inner contoured entrance zone 163, through the proximal ends of the inner holes 164, through the conical sections 167 at the distal ends of the inner holes 164, and into the proximal ends of the inner capillary holes 176A for extruding fibers from the distal ends of the inner capillary holes 176A at the distal side of the spinneret 106. In one embodiment, the inner contoured entrance zones 163 have substantially no planar or flat surfaces normal to the direction of the central axis $A_1$ of the inner capillary hole 176A, thereby eliminating and/or minimizing the presence of dead areas within the wetted area 153 of the proximal surface 152 of the plate 150.

In one embodiment, the spinneret 106 preferably includes the outer ring 174 formed in the proximal surface 152 of the plate 150 of the spinneret 106. The outer contoured entrance zones, and the outer holes 166 are preferably formed within the outer ring 174. The outer holes 166 have proximal ends that are in communication with distal ends of the outer contoured entrance zones 165 and distal ends that are in communication with proximal ends of respective outer capillary holes 176B (FIG. 12C) formed in the distal surface 171 of the alignment projection 168 of the spinneret. Although not shown in FIGS. 14B and 14C, the outer contoured entrances zones 165, the outer holes 166, and the outer capillary holes 176B (FIG. 12D) have the same structure and function in a similar manner as described above for the inner contoured entrance zones, the inner holes and the inner capillary holes for extruding polymer fibers. Thus, in one embodiment, the outer contoured entrance zones 165 have substantially no planar or flat surfaces normal to the direction of the central axis $A_1$ of the outer capillary hole 176B, thereby eliminating and/or minimizing the presence of dead areas within the wetted area 153 of the proximal surface 152 of the plate 150.

Figure 15:
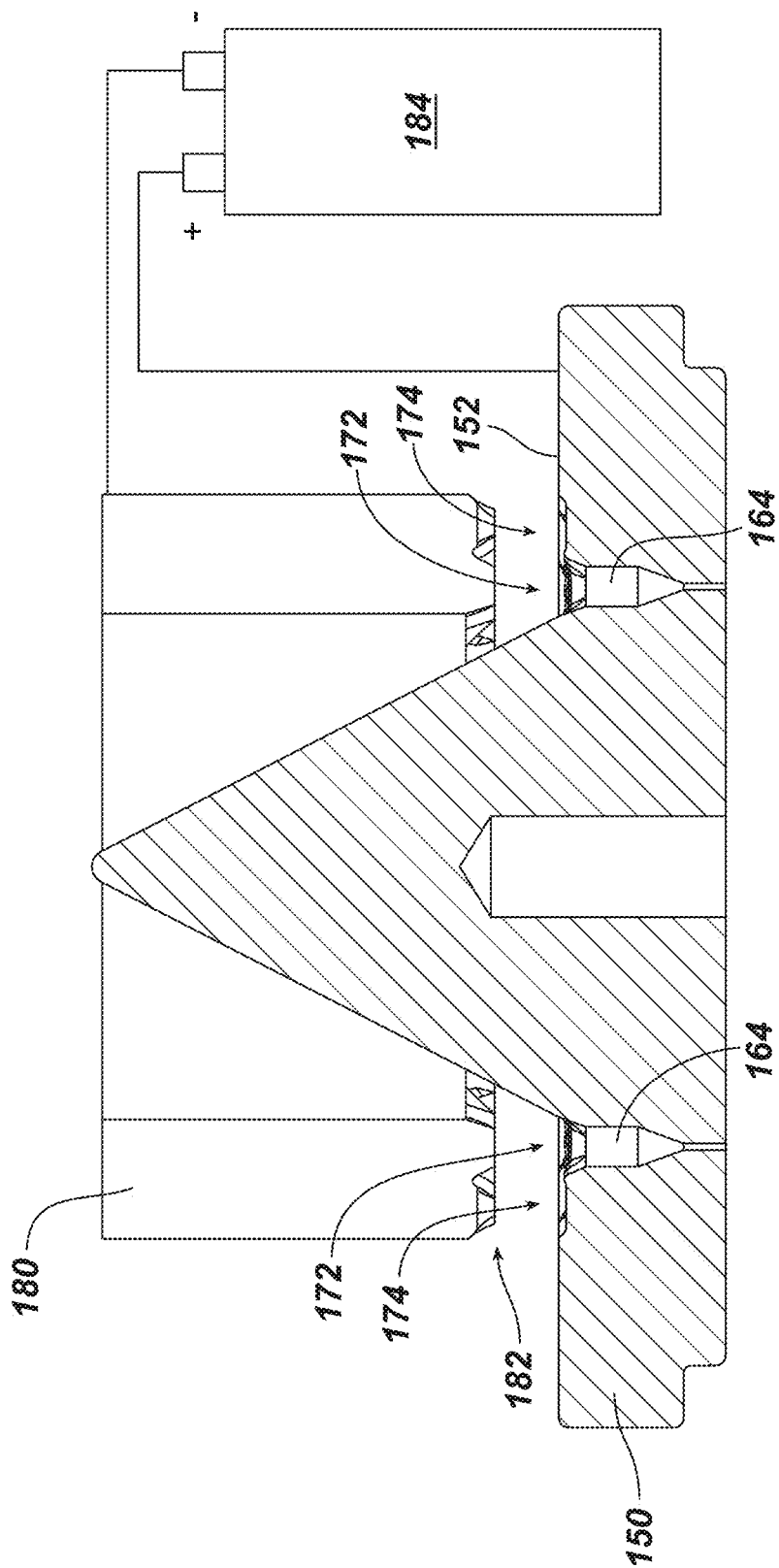
FIG. 15 shows a method of making the spinneret shown in FIGS. 14A-14C, in accordance with one embodiment of the present patent application.

Referring to FIG. 15, in one embodiment, an electric discharge machining (EDM) method may be utilized to shape the geometry of the inner and outer rings, the inner and outer contoured entrance zones, the inner and outer holes, and the inner and outer capillary holes that are formed in the spinneret plate. In one embodiment, the rings, slots, contoured entrance zones, holes, and capillary holes may be formed in the spinneret plate using micro EDM technology, such as that sold by National Jet Company, Inc. of LeVale, Maryland. In one embodiment, an EDM system preferably includes an electrode 180 having an underside 182. The underside 182 of the electrode 180 preferably has a complex geometry that is utilized for forming a mirror complex geometry in the plate of the spinneret. The complex geometry is designed to ensure that the wetted area of the proximal surface of the plate has no flat surfaces that are normal to the direction of the central axis of the respective capillary holes or the direction of the central axis of the distal ends of the holes used to extrude polymer fibers.

In one embodiment, the electrode 180 may be connected with a power source 184 that generates a recurring electrical discharge to form small, detailed contours or cavities in the plate so that the contoured entrance zones that surround the proximal ends of the holes have substantially no flat and/or planar surfaces that surround the proximal ends of the inner and outer holes 164, 166 formed in the respective inner and outer rings 172, 174. Eliminating flat and/or planar surfaces between the holes minimizes "dead areas" between the holes to avoid the degradation problems discussed above in conjunction with the prior art spinnerets shown in FIGS. 1-5 of the present patent application.

Figure 16A:
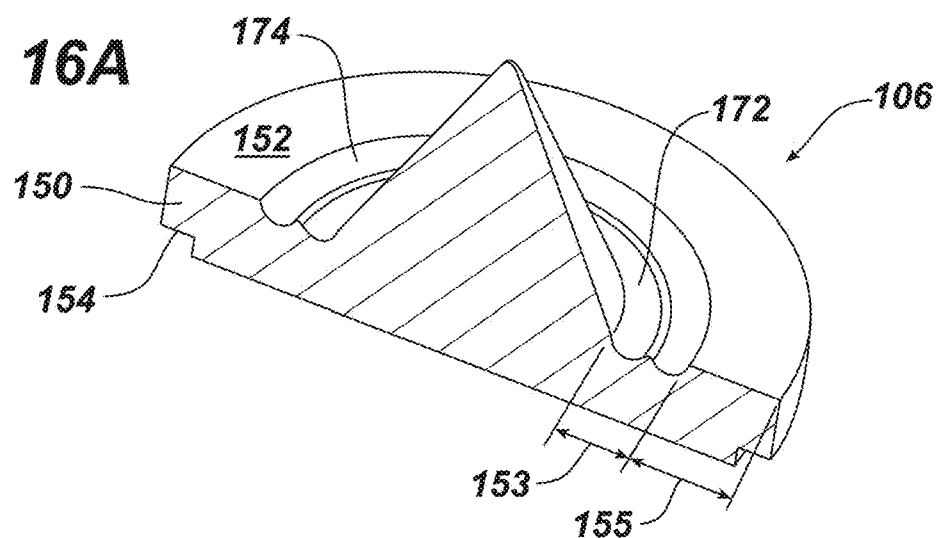
FIG. 16A shows a first stage of a method of making a spinneret, in accordance with one embodiment of the present patent application.

Referring to FIG. 16A, in one embodiment, a spinneret 106 preferably includes the plate 150 having the proximal surface 152 and the distal surface 154. In one embodiment, the inner ring 172 is formed in the proximal surface 152 of the plate 150. The inner ring 172 is preferably recessed and lies below the flat, proximal surface 152 of the plate 150.

In one embodiment, the outer ring 174 is preferably formed in the flat, proximal surface 152 of the plate 150. The outer ring 174 preferably surrounds the inner ring 172. The outer ring 174 preferably defines a depression or groove that is located below the proximal surface 152 of the plate 150.

In one embodiment, the inner and outer rings 172 and 174 are preferably located within a wetted area 153 of the proximal surface 152 of the plate 150, and the proximal surface 152 of the plate 150 includes a sealed area 155 that surrounds the wetted area 153.

Figure 16B:
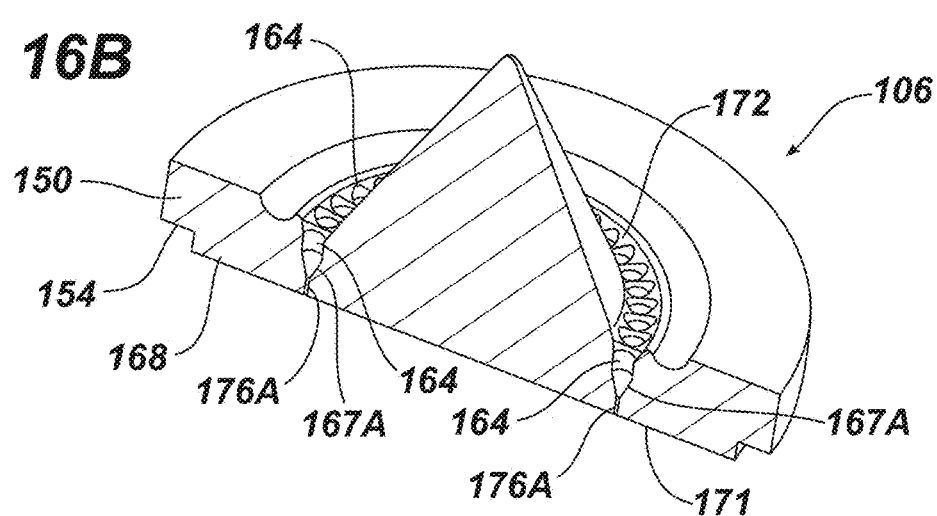
FIG. 16B shows a second stage of a method of making a spinneret, in accordance with one embodiment of the present patent application.
Figure 16C:
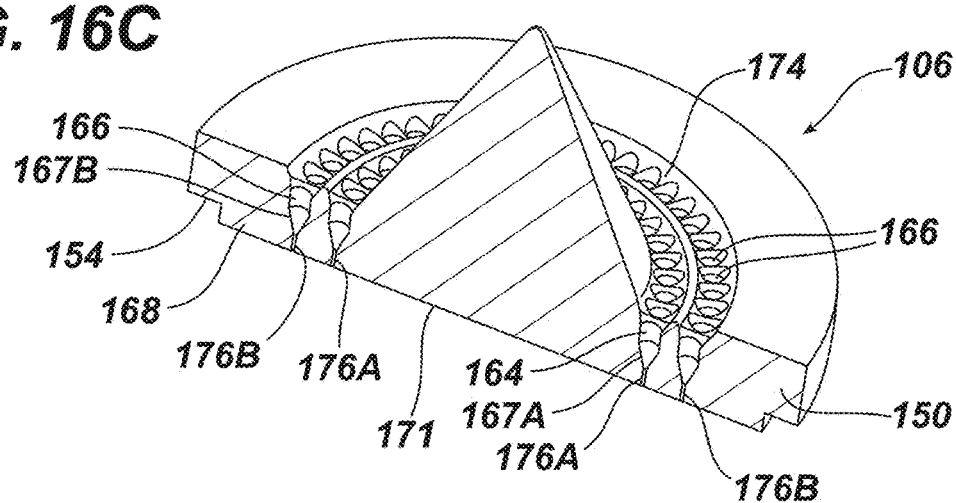
FIG. 16C shows a third stage of a method of making a spinneret, in accordance with one embodiment of the present patent application.
Figure 16D:
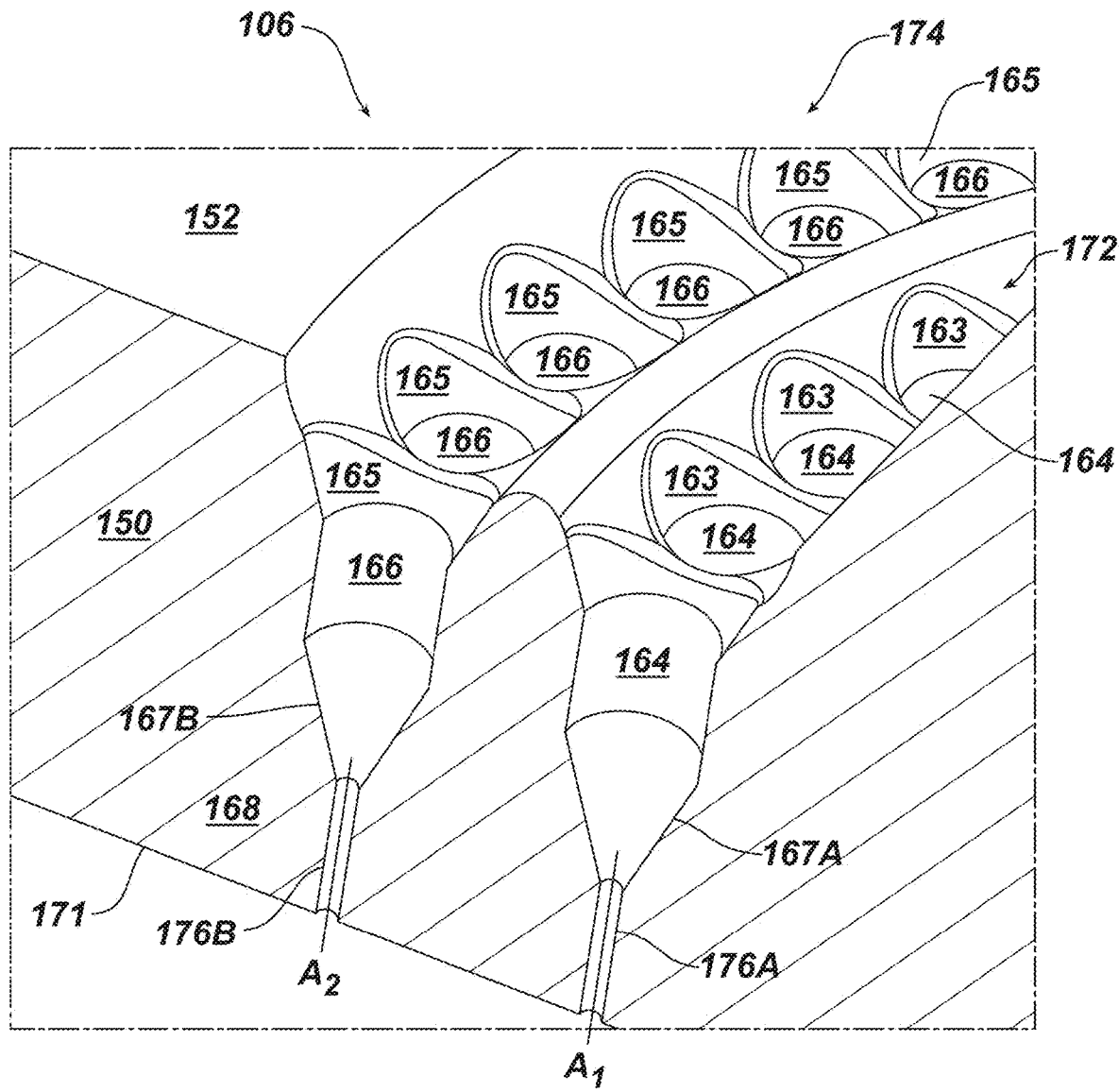
FIG. 16D is a magnified view of a section of the spinneret shown in FIG. 16C.

Referring to FIGS. 16B-16D, in one embodiment, the array of inner holes 164 are preferably formed (e.g., drilled, electric discharge machined) in the inner ring 172 and extend toward the bottom or distal surface 171 of the alignment projection 168 that extends below the distal surface 154 of the plate 150 of the spinneret 106. In one embodiment, the inner capillary holes 176A are formed in the bottom surface 171 of the alignment projection 168. The inner capillary holes 176A preferably have upper or proximal ends that intersect with lower or distal ends of the respective inner holes 164. The distal ends of the inner holes 164 preferably taper inwardly via conical sections 167A, which are in communication with proximal ends of the inner capillary holes 176A.

In one embodiment, the outer holes 166 are preferably formed in the outer ring 174 of the spinneret 106. The outer holes 166 preferably extend toward the distal surface 171 of the alignment projection 168 that extends below the distal surface 154 of the plate 150 of the spinneret 106. In one embodiment, the outer capillary holes 176B are formed in the distal surface 171 of the alignment projection 168 of the spinneret 106. The outer capillary holes 176B preferably have upper or proximal ends that are in communication with lower or distal ends of the respective outer holes 166 that are located within the outer ring 174 of the spinneret 106. The distal ends of the outer holes 166 preferably taper inwardly via conical sections 167B that are in communication with proximal ends of the outer capillary holes 176B.

Referring to FIG. 16D, in one embodiment, each inner capillary hole 176A preferably has a central axis $A_1$ that extends along the length of the inner capillary hole 176A. In one embodiment, the inner contoured entrance zones 163 have sloping, contoured, flat and/or planar surfaces, whereby none of the sloping, contoured, flat and/or planar surfaces within an inner contoured entrance zone 163 are normal to the central axis $A_1$ of the inner capillary hole 176A.

In one embodiment, each outer capillary hole 176B preferably has a central axis $A_2$ that extends along the length of the outer capillary hole 176B. In one embodiment, the outer contoured entrance zones 165 have sloping, contoured, flat and/or planar surfaces, whereby none of the sloping, contoured, flat and/or planar surfaces within an outer contoured entrance zone 165 are normal to the central axis $A_2$ of the outer capillary hole 176B.

Figure 17A:
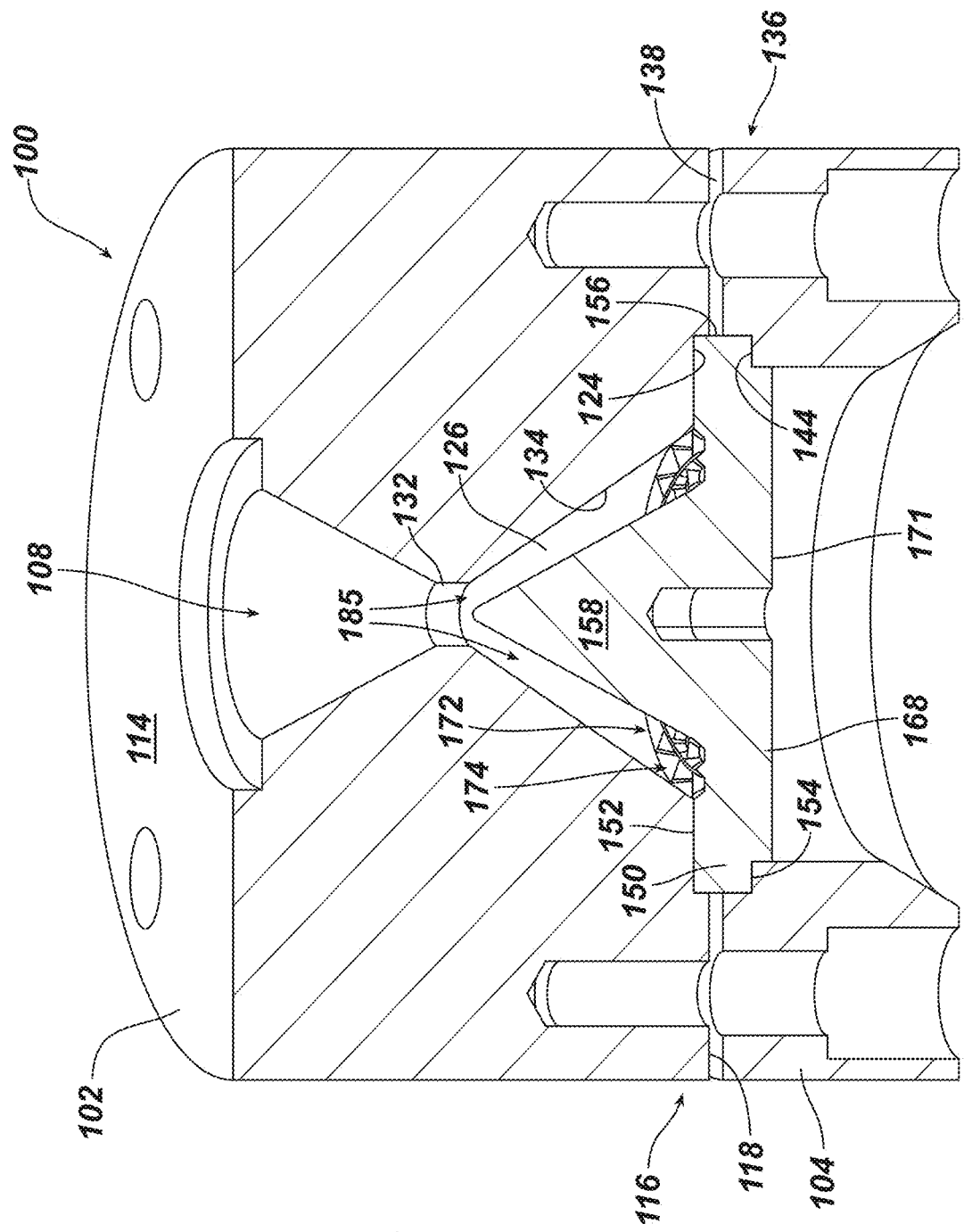
FIG. 17A is a cross-sectional view of the polymer extrusion die assembly of FIGS. 6A and 6B including the die body of FIGS. 8A-8D and 9A-9B, the die retainer ring of FIGS. 10A-10D, and 11A-11B, and the spinneret of FIGS. 12A-12D, 13A-13B, 14A-14C, 15A-15C and 16, in accordance with one embodiment of the present patent application.
Figure 17B:
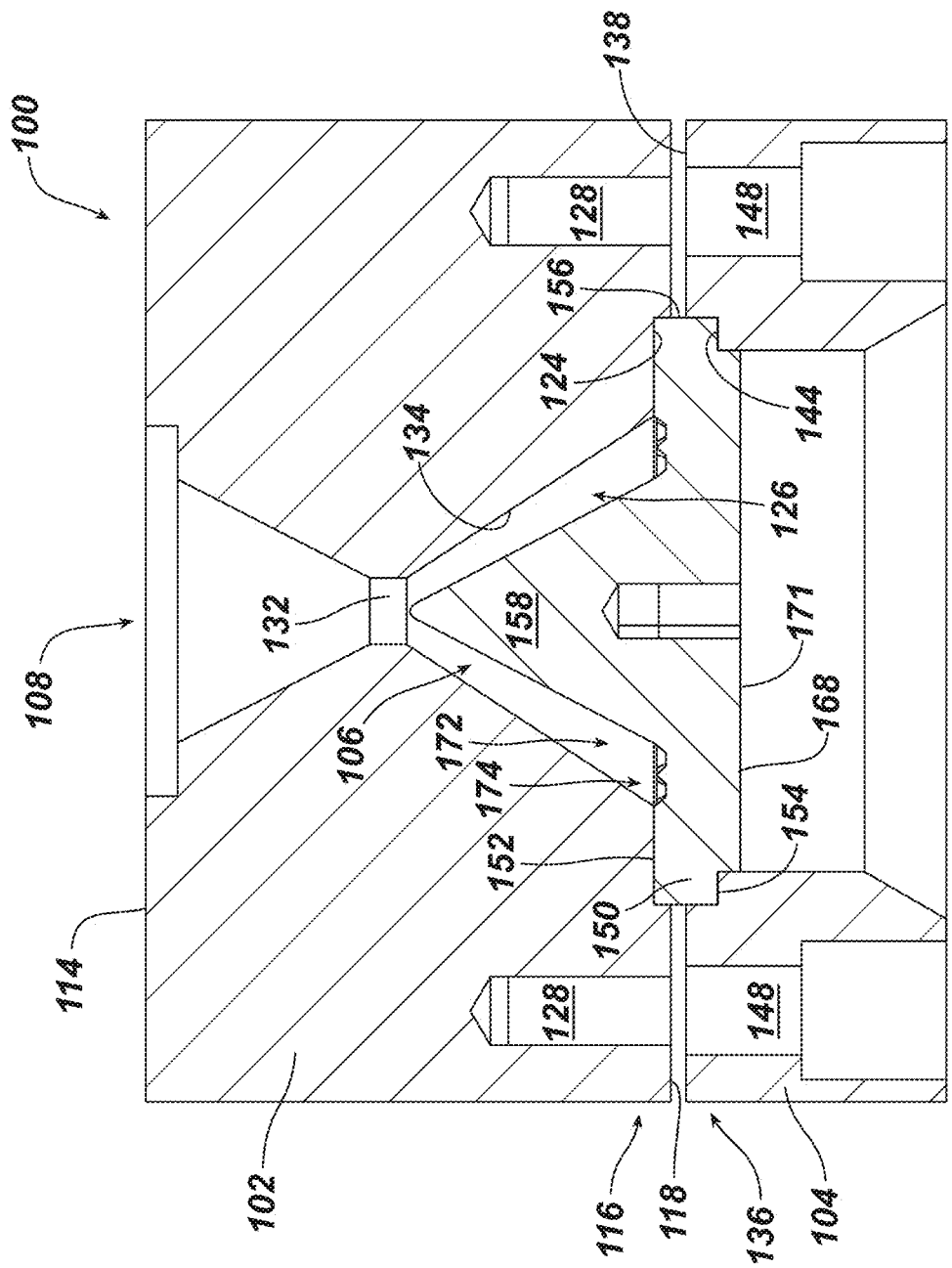
FIG. 17B is another cross-sectional view of the polymer extrusion die assembly of FIG. 17A including the die body, the die retainer ring, and the spinneret.

Referring to FIGS. 17A and 17B, in one embodiment, in order to assemble the polymer extrusion die assembly 100, the spinneret 106 is preferably disposed between the lower or distal end 116 of the die body 102 and the upper or proximal end 136 of the die retainer ring 104. In one embodiment, the distal surface 154 of the plate 150 of the spinneret 106 is preferably seated within the top annular groove 144 formed in the flat top surface 138 of the die retainer ring 104. The outer perimeter 156 of the plate 150 of the spinneret 106 is preferably seated within the bottom annular groove 124 formed in the bottom surface 118 of the die body 102. The cone 158 of the spinneret 106 is preferably disposed within the polymer melt outlet opening 126 of the die body 102. The outer sloping walls of the cone 158 are preferably spaced away from the sloping side walls 134 of the polymer melt outlet opening 126. The outer surface of the cone 158 and the sloping side walls 134 of the polymer melt outlet opening 126 preferably define a polymer melt flow path 185 that extends along the sides of the cone 158 and that has a lower end that intersects with the inner and outer rings 172, 174 that are located within the wetted area 153 (FIG. 13B) of the proximal surface 152 of the plate 150. The polymer melt flow path 185 preferably directs the polymer melt into the wetted area of the proximal surface 152 of the plate 150.

In one embodiment, as the polymer melt is fed into the inlet opening 108 formed in the top surface 114 of the die body 102, the polymer melt preferably passes through the restricted flow region 132 of the flow path and then into the polymer melt flow path 185 extending between the cone 158 and the sloping side walls 134 of the polymer melt outlet opening 126. The polymer melt is preferably forced into the inner and outer contoured entrance zones that are in communication with the proximal ends of the respective inner and outer holes 164, 166 (FIG. 16D) formed in the respective inner and outer rings 172, 174 of the plate 150 of the spinneret, and is then extruded through the respective inner and outer capillary holes 176A, 176B (FIG. 16D) formed in the distal surface 171 of the alignment projection 168 that extends from the distal surface of the plate 150 of the spinneret 106.

In one embodiment, fastening bolts (not shown) may be inserted into bolt holes 148A-148D (FIG. 10B) formed in the top surface of the die retainer ring 104 and the bolt holes 128A-128D (FIG. 8D) formed in the bottom surface of the die body 102 for aligning the die body 102 and the die retainer ring 104 with one another and for holding the components of the polymer extrusion die assembly 100 together during a fiber extrusion process.

In one embodiment, a spinneret may have a single ring of spaced holes that are designed for extruding a polymer melt to form polymer fibers. In one embodiment, the spinneret has 28 holes that are spaced from one another. In another embodiment, a single ring of spaced holes may be disposed within a preformed slot or ring-shaped groove.

Referring to FIGS. 18A-18D, in one embodiment, a spinneret 206 having 28 holes preferably includes a plate 250 having a top or proximal surface 252 and a bottom or distal surface 254. The spinneret 206 may incorporate one or more of the structural features shown and described above in the embodiments shown in FIGS. 12A-12D, 13A-13B, 14A-14C, and 16A-16D. In one embodiment, the plate 250 may have an annular or circular shape. In one embodiment, the plate 250 preferably has an outer perimeter 256 that defines an outer diameter $OD_5$ that substantially matches the outer diameter $OD_1$ of the bottom annular groove 124 formed at the distal end of the die body 102 (FIG. 8D).

Figure 18A:
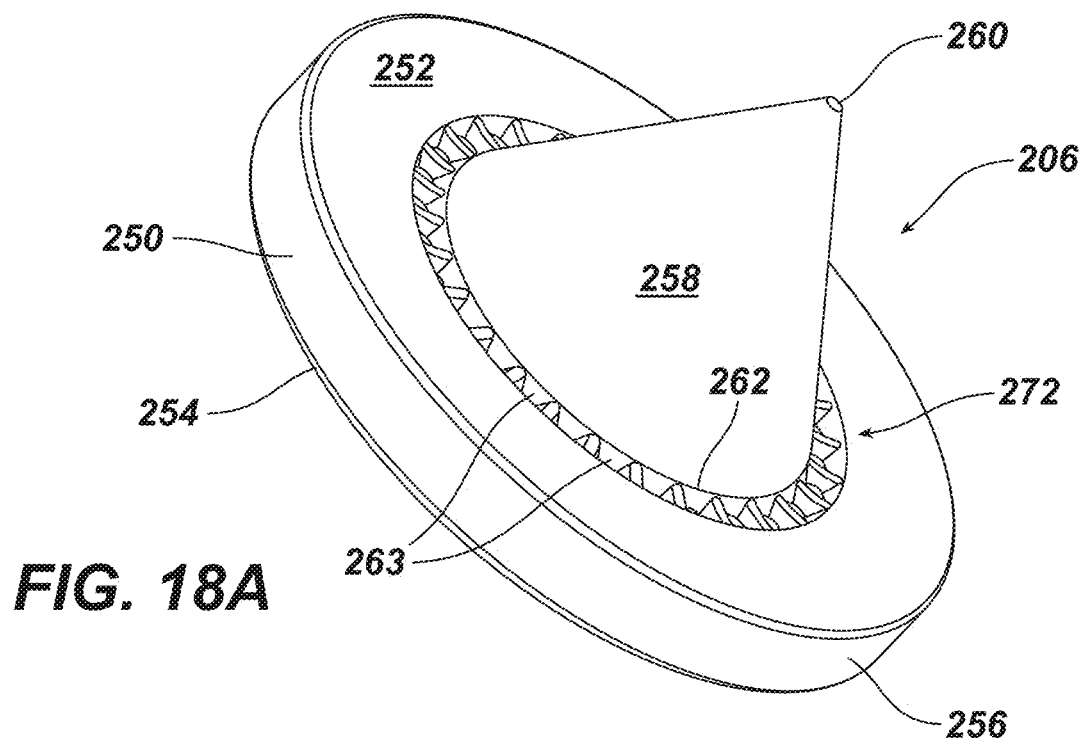
FIG. 18A is a perspective view of a proximal side of a spinneret, in accordance with another embodiment of the present patent application.
Figure 18B:
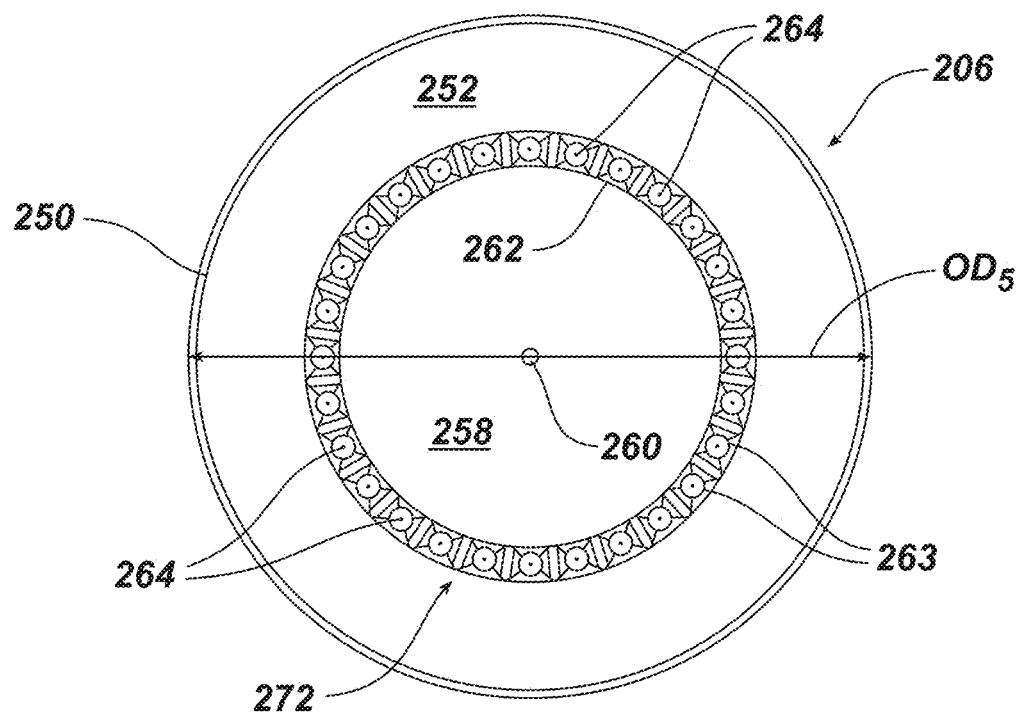
FIG. 18B is a top or proximal side view of the spinneret shown in FIG. 18A.

Referring to FIGS. 18A and 18B, in one embodiment, the spinneret 206 preferably includes a cone 258 that projects above the proximal surface 252 of the plate 250. The cone 258 desirably includes an apex 260 that is adapted to be inserted into the polymer melt outlet opening 126 (FIG. 9B) located at the distal end of the die body 102. The cone 258 preferably includes a base 262 at a lower end thereof that is in substantial alignment with a plane defined by the flat, proximal surface 252 of the spinneret 206.

Referring to FIGS. 18A-18D, in one embodiment, the spinneret 206 preferably includes a ring 272 having an annular or circular configuration that extends around the base 262 of the cone 258. The spinneret 206 preferably includes contoured entrance zones 263 that are disposed within the ring 272 and that are in communication with proximal ends of holes 264 that extend through the plate 250 for passing a polymer melt through the plate. In one embodiment, the holes 264 are preferably spaced from one another within the ring 272, with one of the contoured entrance zones 263 surrounding each hole 264.

Figure 18C:
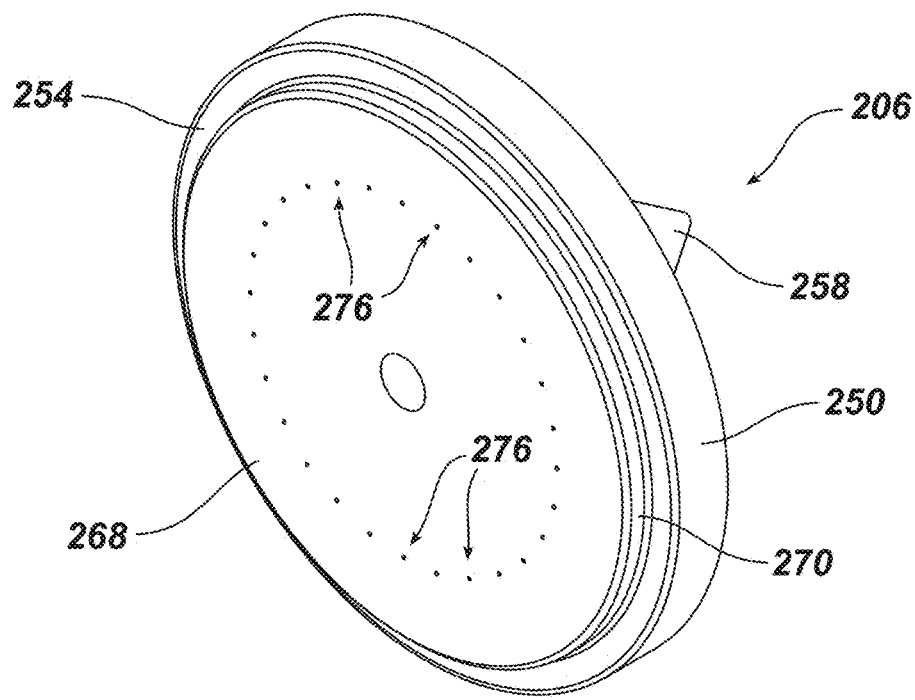
FIG. 18C is a perspective view of a distal side of the spinneret shown in FIGS. 18A and 18B.
Figure 18D:
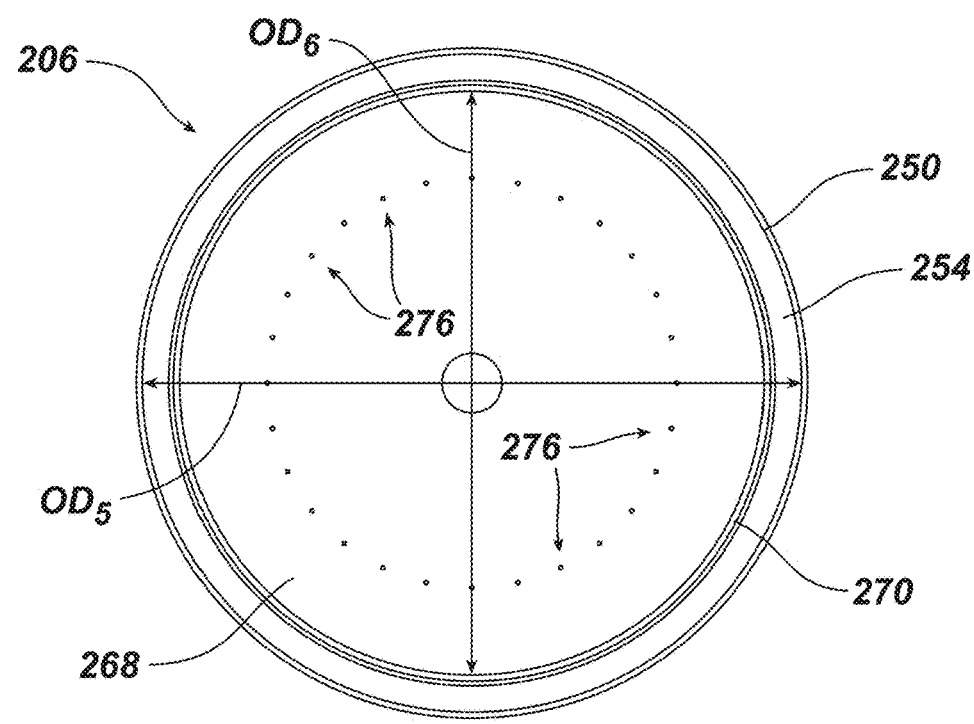
FIG. 18D is a bottom distal side view of the spinneret shown in FIGS. 18A-18C.

Referring to FIGS. 18C and 18D, in one embodiment, the spinneret 206 preferably includes an alignment projection 268 that extends below and/or projects from the distal surface 254 of the plate 250. In one embodiment, the alignment projection 268 has an outer perimeter 270 with a circular configuration that is concentric with the outer perimeter 256 of the plate 250 of the spinneret 206. In one embodiment, the outer perimeter 270 of the alignment projection 268 preferably defines an outer diameter $OD_6$ that is less than the outer diameter $OD_5$ of the plate 250. In one embodiment, the outer diameter $OD_6$ defined by the outer perimeter 270 of the alignment projection 268 preferably matches the second outer diameter $OD_2$ of the top annular groove 144 formed in the top surface 138 of the die retainer ring 104 (FIG. 11B). The matching diameters enable the alignment projection 268 to be seated within the top annular groove of the die retainer ring.

In one embodiment, the spinneret 106 preferably includes capillary holes 276 that are formed in the distal face 271 of the alignment projection 268. The capillary holes have proximal ends that preferably intersect with distal ends of the spaced holes 264 (FIGS. 18A and 18B) for receiving the polymer melt that is fed into the contoured entrance zones 263 and the spaced holes 264 (FIG. 18B).

Figure 19A:
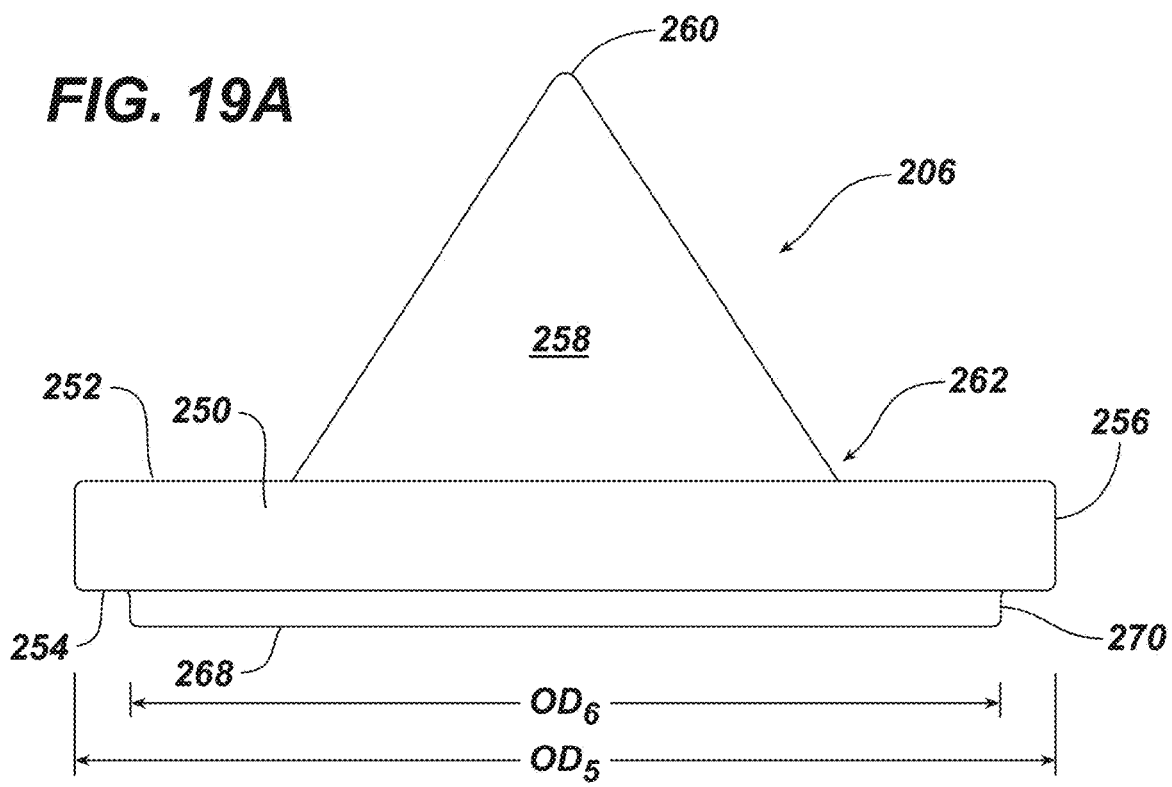
FIG. 19A is a side elevation view of the spinneret shown in FIGS. 18A-18D.
Figure 19B:
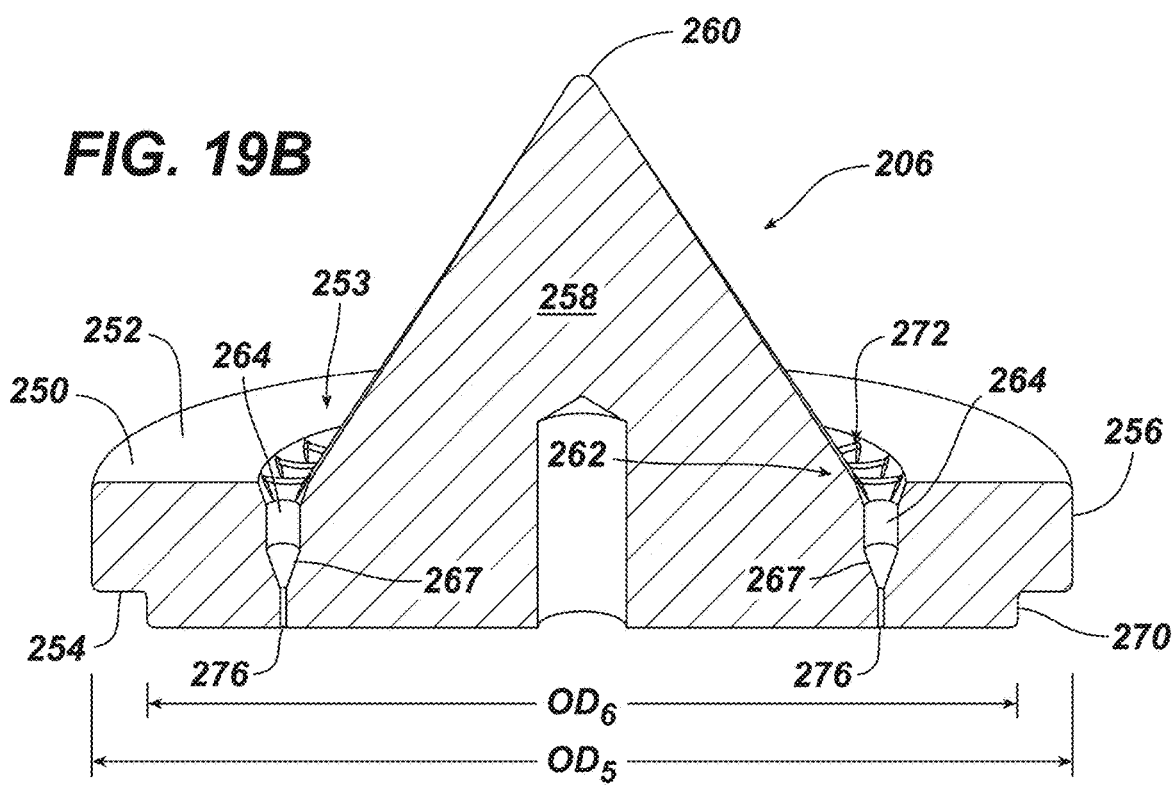
FIG. 19B is a cross-sectional view of the spinneret shown in FIGS. 18A-18D and 19A.

Referring to FIGS. 19A and 19B, in one embodiment, the spinneret 206 preferably includes the plate 250 having the proximal surface 252 and the distal surface 254. The plate 250 preferably has the outer perimeter 256 that defines the outer diameter $OD_5$ of the plate 150.

In one embodiment, the alignment projection 268 preferably extends from the distal surface 254 of the plate 250. The alignment projection 268 desirably includes an outer perimeter 270 that defines an outer diameter $OD_6$ that is less than the outer diameter $OD_5$ of the plate 250.

In one embodiment, the spinneret 206 includes the cone 258 that projects above the proximal surface 252 of the plate 250. In one embodiment, the proximal surface 252 of the plate 250 is flat, planar and/or extends in a horizontal plane. The cone 258 includes the apex 260 and the base 262 having a lower end that is in substantial alignment with a plane defined by the proximal surface 252 of the plate 250.

Figure 19C:
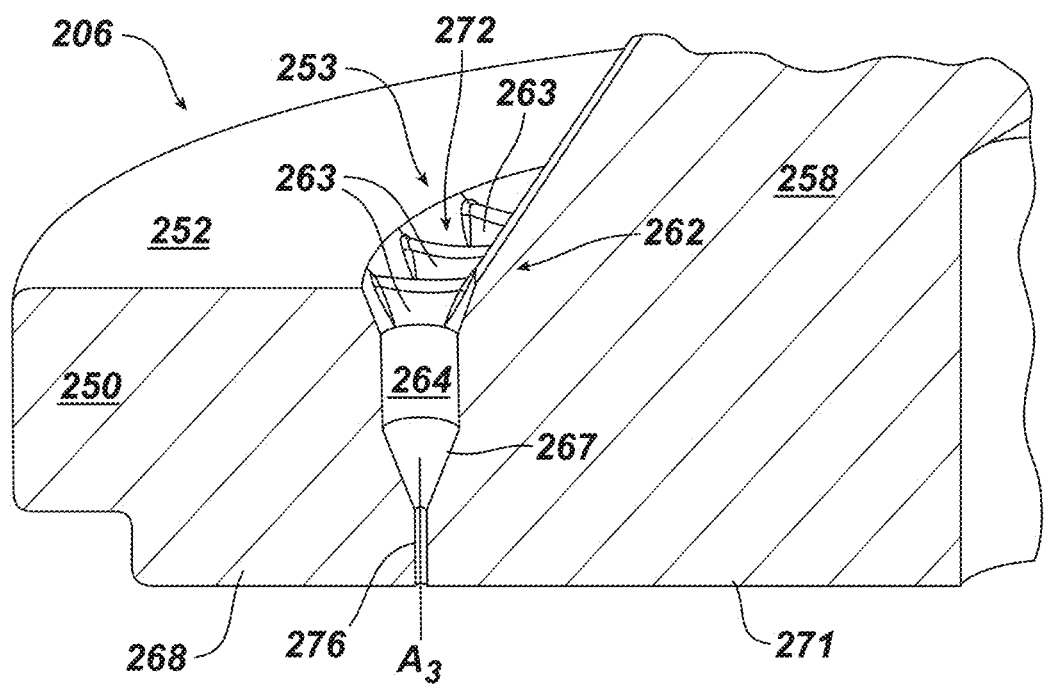
FIG. 19C is a cross-sectional view of a section of the spinneret shown in FIG. 19B.
Figure 19D:
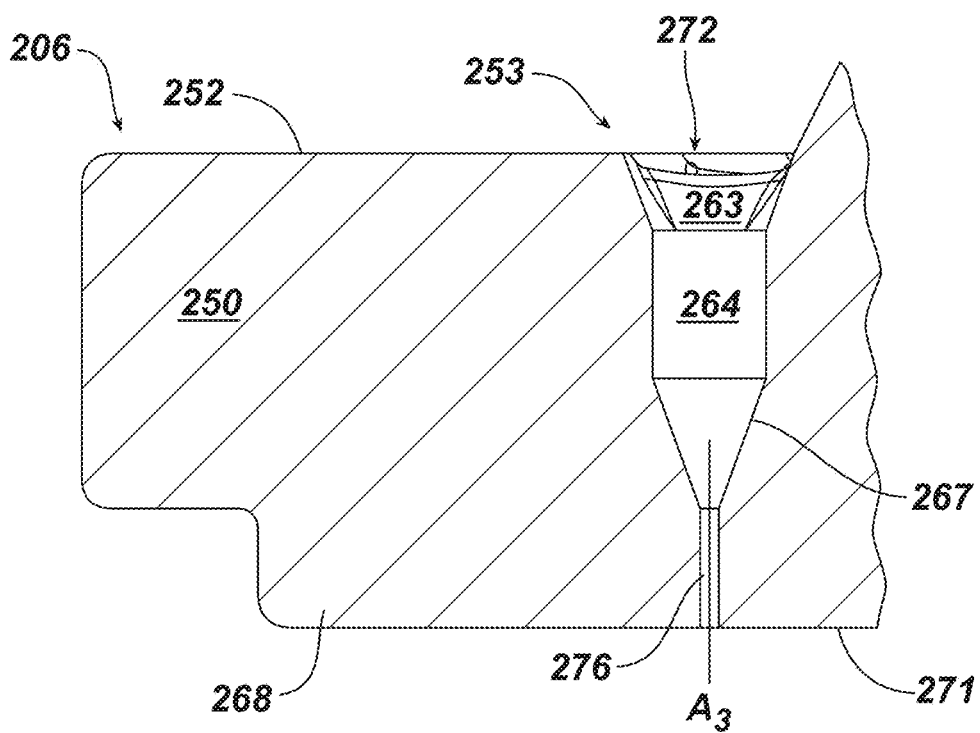
FIG. 19D is a magnified view of a section of the spinneret shown in FIG. 19C.

Referring to FIGS. 19B-19D, in one embodiment, the ring 272 is preferably located in the wetted area 253 of the proximal surface 252 of the plate 250. In one embodiment, the ring 272 is annular or ring shaped and extends around the base 262 of the cone 258. The spinneret 206 preferably includes contoured entrance zones 263 that are located in the ring 272. The contoured entrance zones 263 extend distally from the proximal surface 252 of the plate 250 and have distal ends that are preferably in communication with proximal ends of the holes 264 that extend through the plate. The holes 264 have distal ends including conical sections 267 that taper inwardly to proximal ends of capillary holes 276 that extends to the bottom or distal surface 271 of the alignment projection 268.

In one embodiment, the spinneret 206 preferably includes the contoured entrance zones 263 that extend distally to proximal ends of the holes 264, which insures that there are no flat surfaces that are parallel with the flat, proximal surface 252 of the plate of the spinneret 206. In one embodiment, each contoured entrance zone 263 preferably includes contoured surfaces that extend from the proximal surface 252 of the plate 250 to the proximal end of each hole 264.

In one embodiment, the contoured entrance zone 263 surrounding each hole 264 directly borders the contoured entrance zone surrounding each adjacent hole so that no planar and/or flat surfaces remain between adjacent holes extending through the spinneret plate. The contoured surfaces around the holes 264 may include sloping surfaces, and curved surfaces including concave curved surfaces and convexly curved surfaces.

Referring to FIGS. 19C and 19D, in one embodiment, each capillary hole 276 preferably has a central axis $A_3$ that extends along the length of the capillary hole 276. In one embodiment, the contoured entrance zones 263 have sloping, contoured, flat and/or planar surfaces, whereby none of the sloping, contoured, flat and/or planar surfaces within a contoured entrance zone 263 are normal to the central axis $A_3$ of the capillary hole 276.

In one embodiment, a spinneret may have a single annular ring formed in the proximal surface of a plate and a plurality of contoured entrance zones and spaced holes that are formed in the annular ring for extruding a polymer melt. In one embodiment, the spinneret may have 24 contoured entrance zones and 24 holes (one associated with each contoured entrance zone), which are spaced from one another within the single annular ring.

Referring to FIGS. 20A-20D, in one embodiment, a spinneret 306 having 24 holes preferably includes a plate 350 having a top or proximal surface 352 and a bottom or distal surface 354. The plate 350 may have an annular or circular shape. The plate 350 preferably has an outer perimeter 356 that defines an outer diameter $OD_7$ that substantially matches the outer diameter $OD_1$ of the bottom annular groove 124 at the distal end of the die body 102 (FIG. 8D).

Figure 20A:
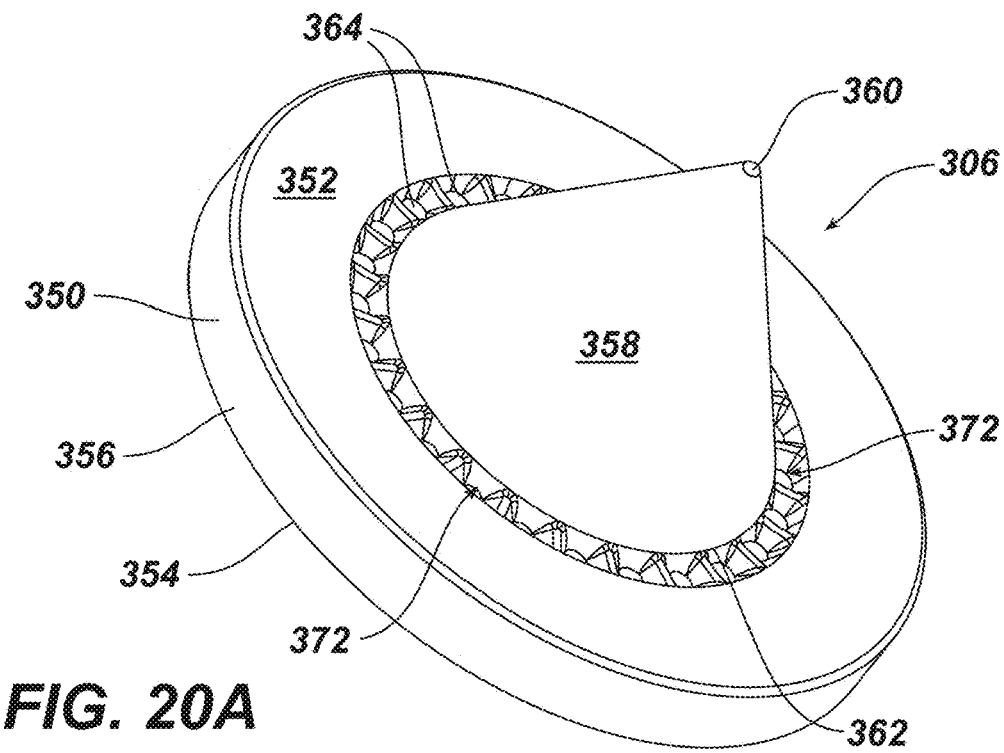
FIG. 20A is a perspective view of a proximal side of a spinneret, in accordance with another preferred embodiment of the present patent application.
Figure 20B:
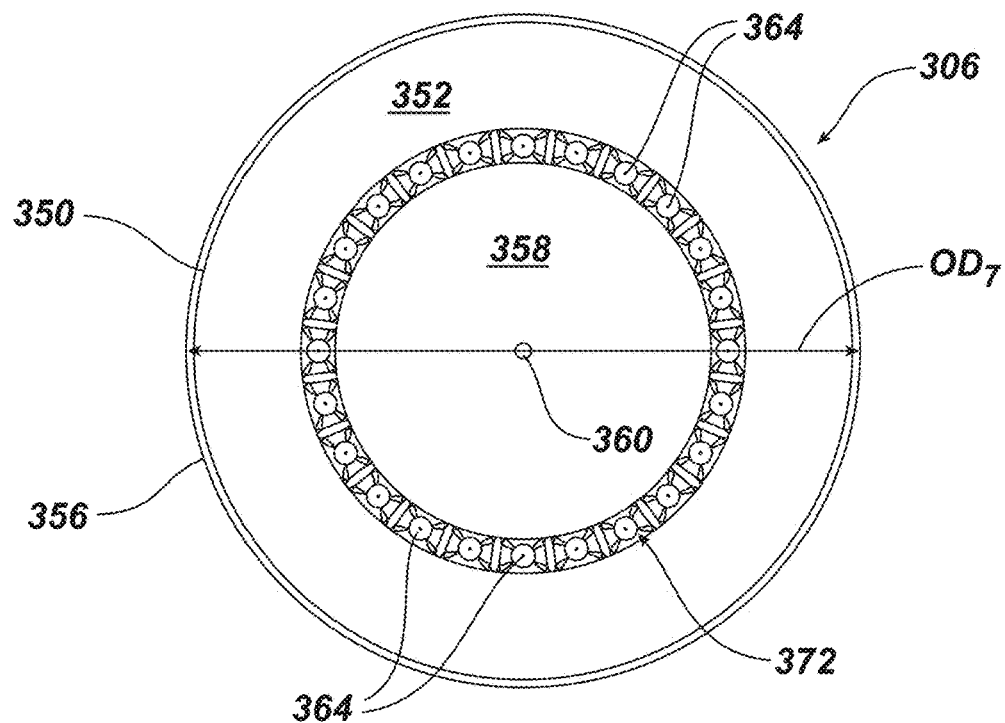
FIG. 20B is a top or perspective side view of the spinneret shown in FIG. 20A.

Referring to FIGS. 20A and 20B, in one embodiment, the spinneret 306 preferably includes a cone 358 that projects above the proximal surface 352 of the plate 350. The cone 358 desirably includes an apex 360 that is adapted to be inserted into the hollow cone of the polymer melt outlet opening 126 (FIG. 9B) located at the distal end of the die body 102. The cone 358 preferably includes a base 362 at a lower end thereof that is in substantial alignment with a plane defined by the flat, proximal surface 352 of the spinneret 306.

Referring to FIGS. 20A-20D, in one embodiment, the spinneret 306 preferably includes a ring 372 having an annular configuration that surrounds the base 362 of the cone 358. In one embodiment, the spinneret 306 preferably includes contoured entrance zones 363 that are located in the ring 372. Each contoured entrance zone 363 is preferably associated with a hole 364 that extends through the plate 350 for passing a polymer melt through the plate. In one embodiment, the contoured entrance zones extend toward the distal surface 354 of the plate 350 and have distal ends that are in communication with the proximal ends of the respective holes 364.

Figure 20C:
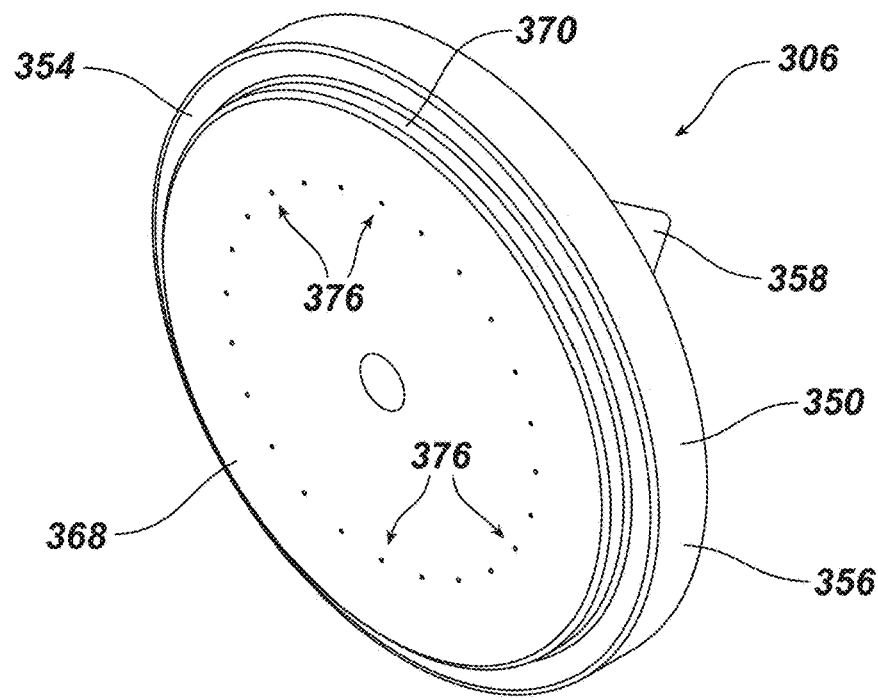
FIG. 20C is a perspective view of a distal side of the spinneret shown in FIGS. 20A-20B.
Figure 20D:
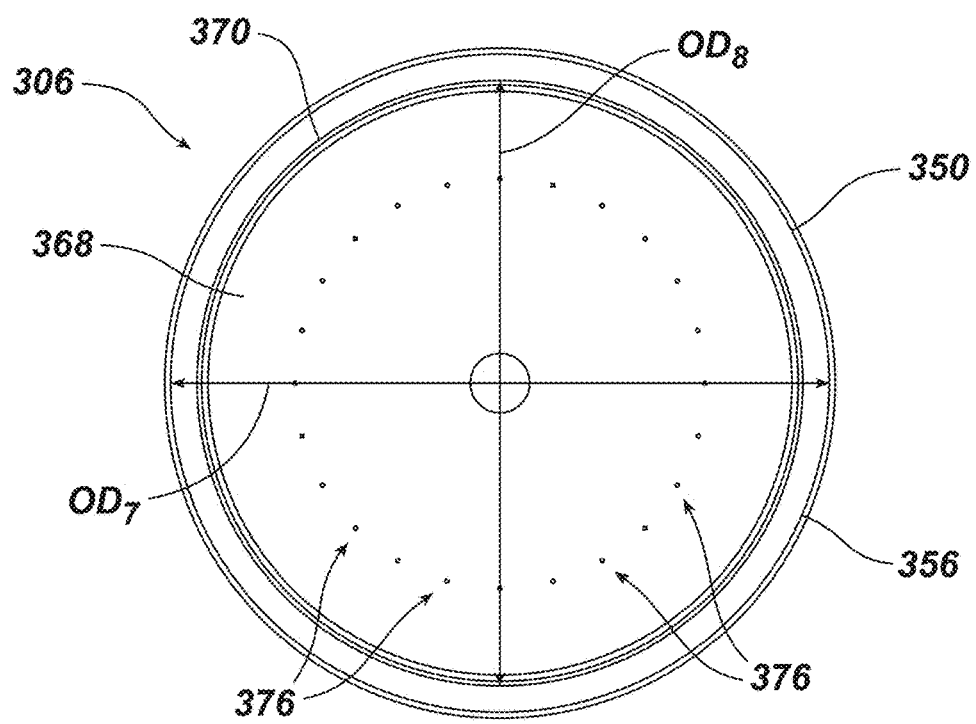
FIG. 20D is a bottom or distal side view of the spinneret shown in FIGS. 20A-20C.

Referring to FIGS. 20C and 20D, in one embodiment, the spinneret 306 preferably includes an alignment projection 368 that extends below and/or projects from the distal surface 354 of the plate 350. In one embodiment, the alignment projection 368 has an outer perimeter 370 with a circular configuration that is concentric with the outer perimeter 356 of the plate 350 of the spinneret 306. In one embodiment, the outer perimeter 370 of the alignment projection 368 preferably defines an outer diameter $OD_8$ that is less than the outer diameter $OD_7$ of the plate 350. In one embodiment, the outer diameter $OD_8$ defined by the outer perimeter 370 of the alignment projection 368 preferably matches the second outer diameter $OD_2$ of the top annular groove 144 formed in the top surface 138 of the die retainer ring 104 (FIG. 11B). The matching diameters enable the alignment projection 368 to be seated within the top annular groove of the die retainer ring.

In one embodiment, the spinneret 306 preferably includes capillary holes 376 that are formed in the distal face 371 of the alignment projection 368. The capillary holes have proximal ends that intersect with distal ends of the spaced holes 364 (FIGS. 20A and 20B) for receiving the polymer melt that is fed through the spaced holes.

Figure 21A:
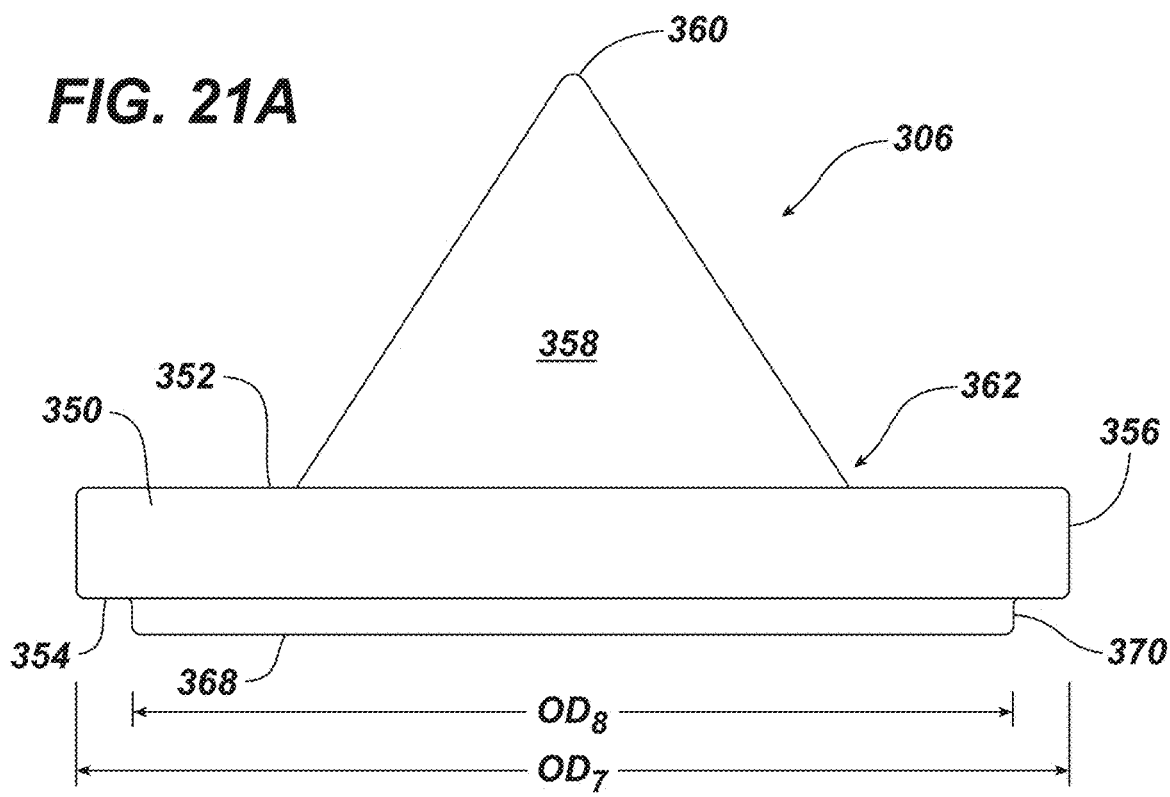
FIG. 21A is a side elevation view of the spinneret shown in FIGS. 20A-20D.
Figure 21B:
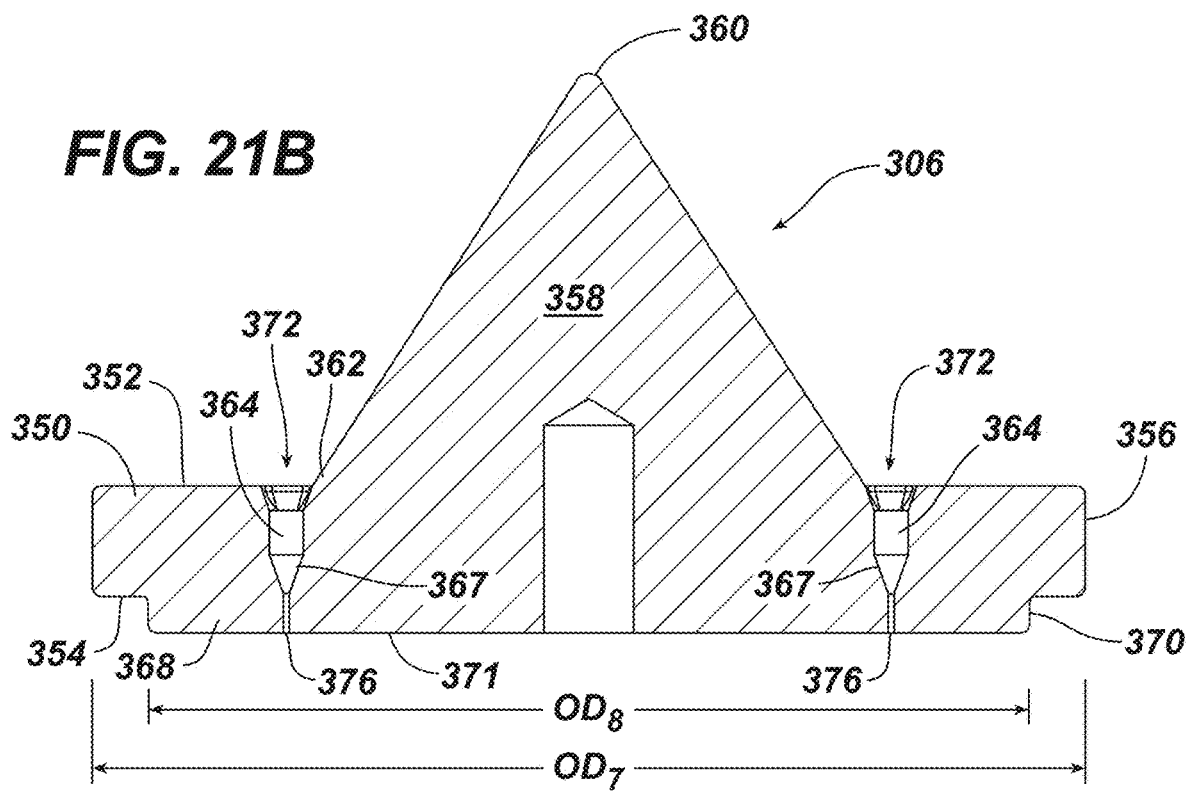
FIG. 21B is a cross-sectional view of the spinneret shown in FIGS. 20A-20D and FIG. 21A.

Referring to FIGS. 21A and 21B, in one embodiment, the spinneret 306 preferably includes the plate 350 having the proximal surface 352 and the distal surface 354. The plate 350 preferably has the outer perimeter 356 that defines the outer diameter $OD_7$ of the plate 250.

In one embodiment, the alignment projection 368 preferably extends from the distal surface 354 of the plate 350. The alignment projection 368 desirably includes an outer perimeter 370 that defines an outer diameter $OD_6$ that is less than the outer diameter $OD_7$ of the plate 350.

In one embodiment, the spinneret 306 preferably includes the cone 358 that projects above the proximal surface 352 of the plate 350. In one embodiment, the proximal surface 352 of the plate 350 is flat and/or extends in a horizontal plane. The cone 358 includes the apex 360 and the base 362 having a lower end that is in substantial alignment with a plane defined by the proximal surface 352 of the plate 350.

Figure 21C:
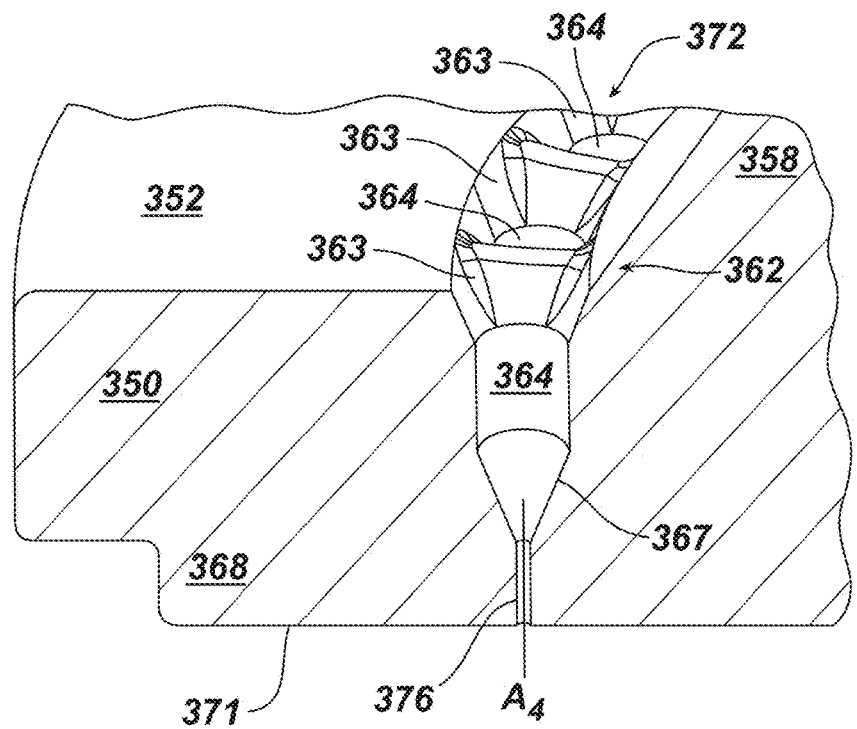
FIG. 21C is a cross-sectional view of a section of the spinneret shown in FIG. 21B.
Figure 21D:
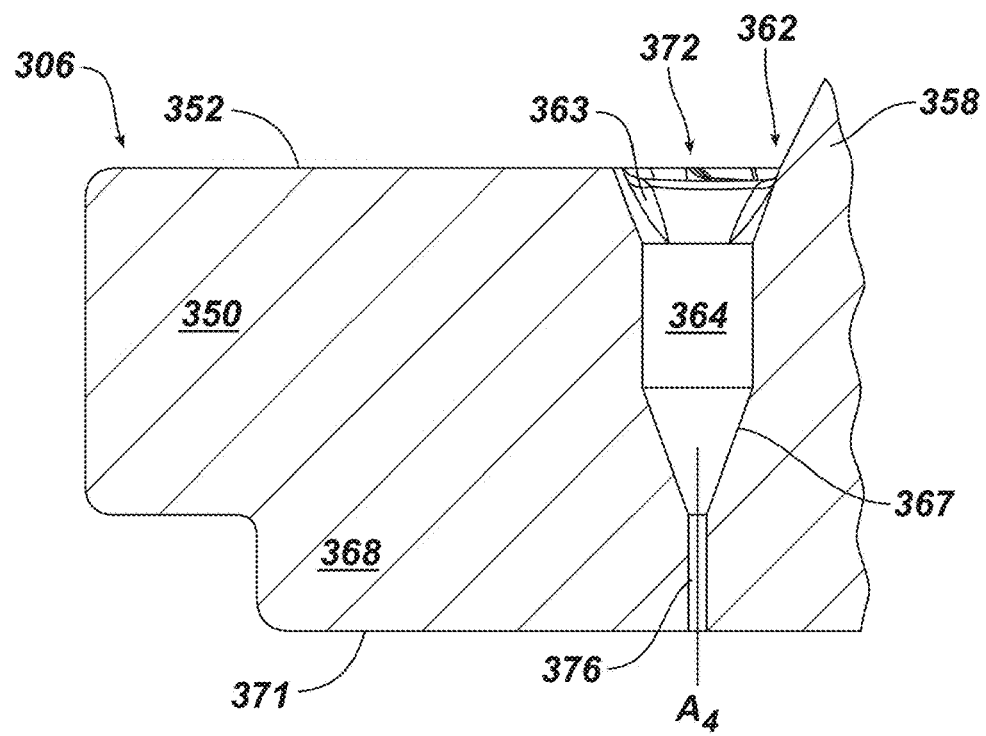
FIG. 21D is a magnified view of a section of the spinneret shown in FIG. 21C.

Referring to FIGS. 21B-21D, in one embodiment, the holes 364 that are formed in the plate (e.g., by drilling, using EDM) are preferably located within a ring 372 that is formed in the proximal surface 352 of the plate 350. In one embodiment, the ring 372 is annular or ring shaped and extends around the base 362 of the cone 358. The ring 372 is preferably recessed relative to the proximal surface 352 of the plate 350. The spinneret 306 preferably includes the capillary holes 376 that are formed in the bottom surface 371 of the alignment projection 368. The capillary holes 376 are preferably in communication with distal ends of the respective holes 364 that are formed in the plate 350. The distal ends of the holes 364 preferably include tapered, conical surfaces 367 that taper inwardly to the proximal ends of the capillary holes 376. In one embodiment, the capillary holes 367 preferably have lengths that extend along a longitudinal axis $A_4$.

In one embodiment, the ring 372 preferably includes contoured entrance zones 363 that extend distally to the proximal ends of the respective holes 364 that extend through the spinneret plate 350. The contoured entrance zones 363 preferably include contoured, sloping, flat and/or planar surfaces with none of the contoured, sloping, flat and/or planar surfaces being normal to the central axes $A_4$ that extend along the lengths of the respective capillary holes 376. In one embodiment, a contoured entrance zone 363 preferably surrounds the proximal end of each hole 364 that is formed in the plate.

In one embodiment, the contoured entrance zone 363 for each hole 364 directly borders the contoured entrance zone for each adjacent hole so that no planar and/or flat surfaces remain between adjacent holes within the wetted area of the proximal surface 352 of the spinneret plate 350. The contoured entrance zones 363 around the holes 364 may include sloping surfaces, and curved surfaces including concave curved surfaces and convexly curved surfaces.

Figure 2:
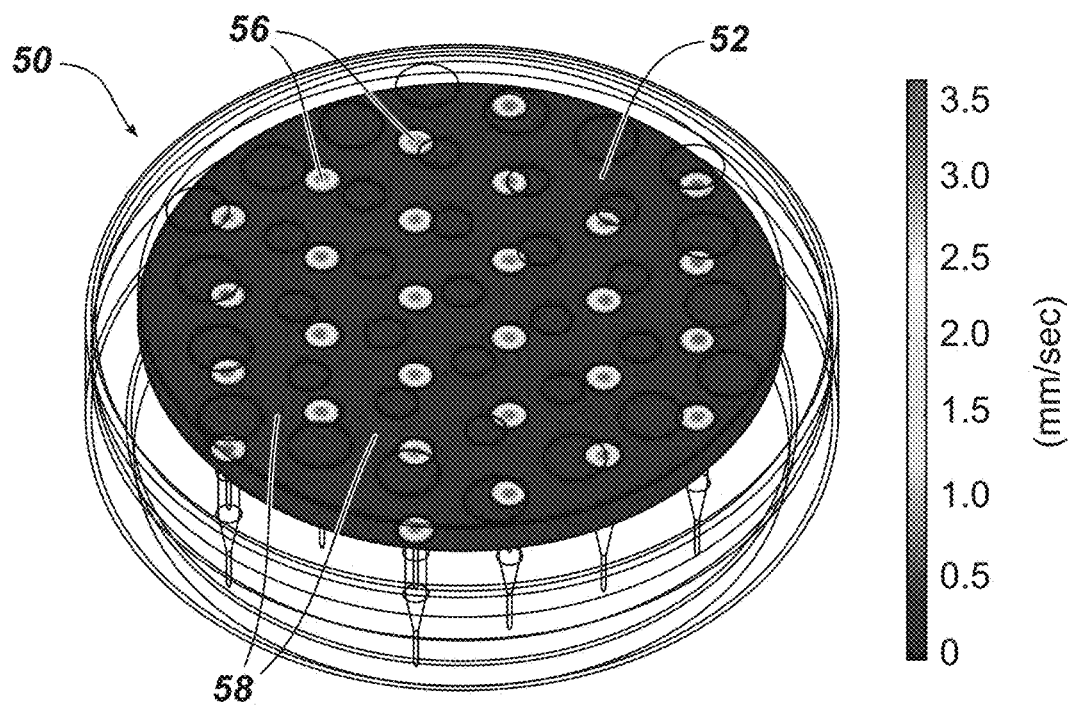
FIG. 2 illustrates the flow velocity profile of a polymer melt as it flows through the holes and across the polymer wetted surfaces of the prior art spinneret shown in FIG. 1.
Figure 3:
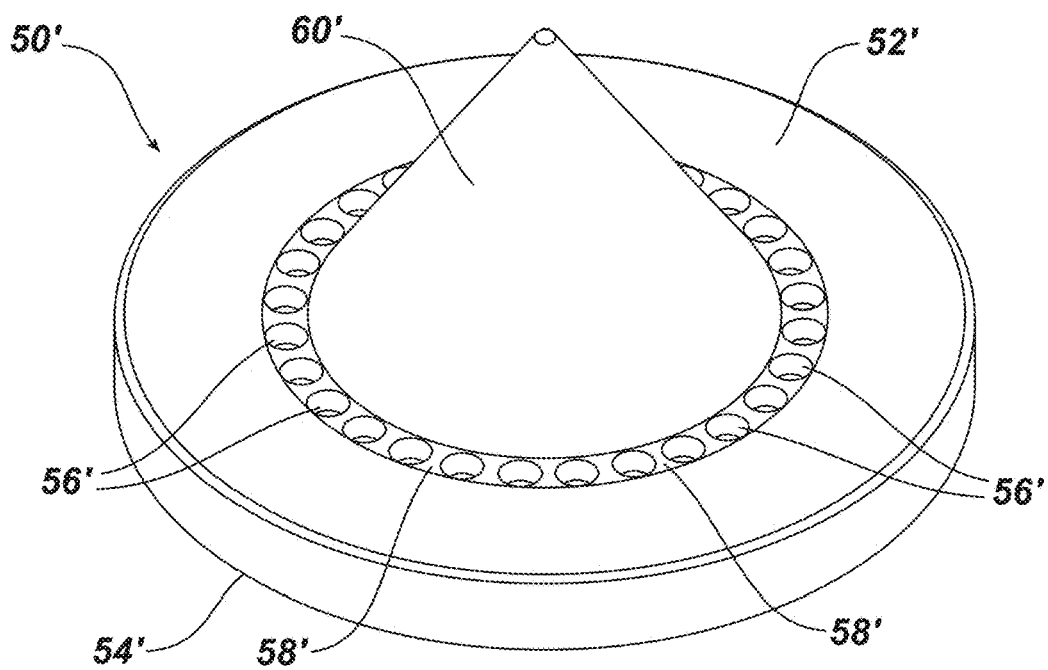
FIG. 3 is a perspective view of a second prior art spinneret having holes for extruding flowable polymer and a cone projecting from a top surface of a plate.
Figure 4:
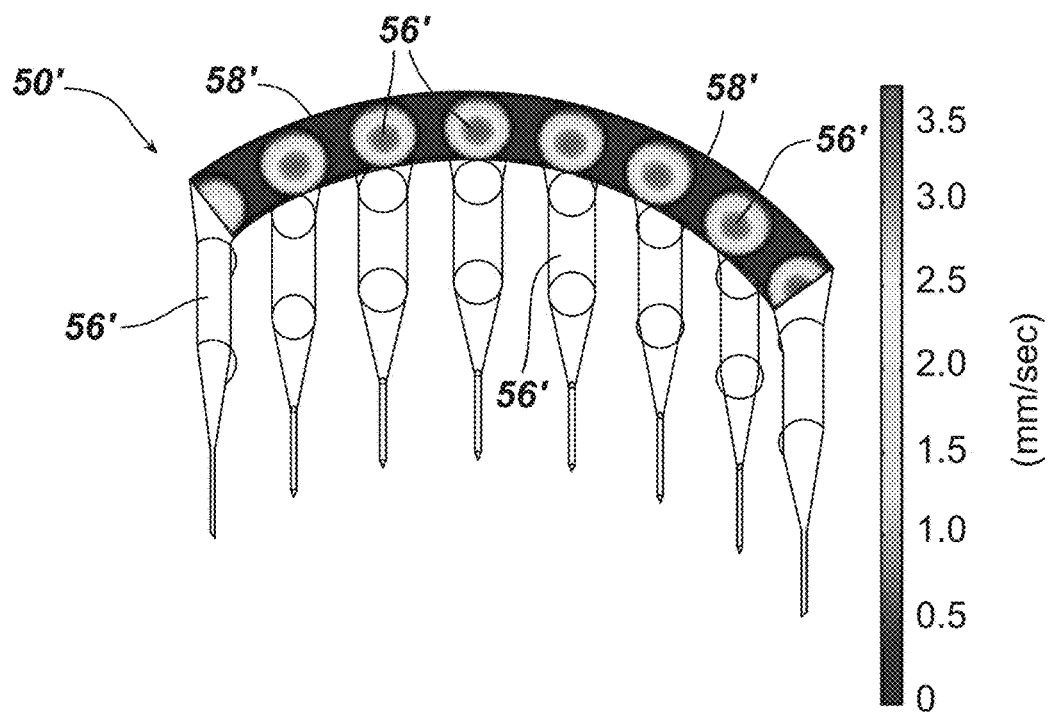
FIG. 4 shows the flow velocity profile of a polymer melt as it flows through the holes and across the polymer wetted surfaces of the second prior art spinneret shown in FIG. 3.
Figure 5:
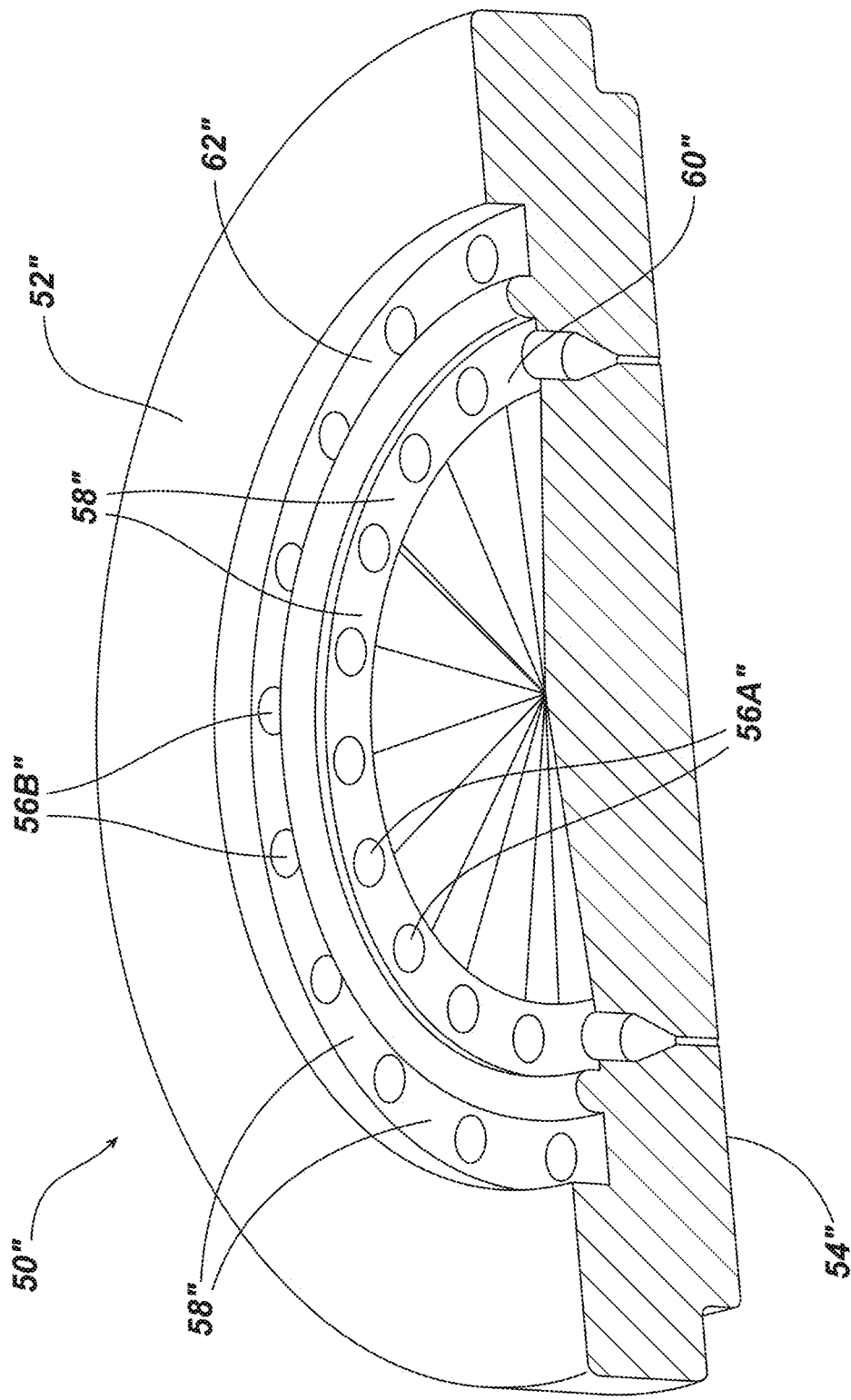
FIG. 5 is a perspective, cross-sectional view of a third prior art spinneret used for extruding flowable polymer.
Figure 22:
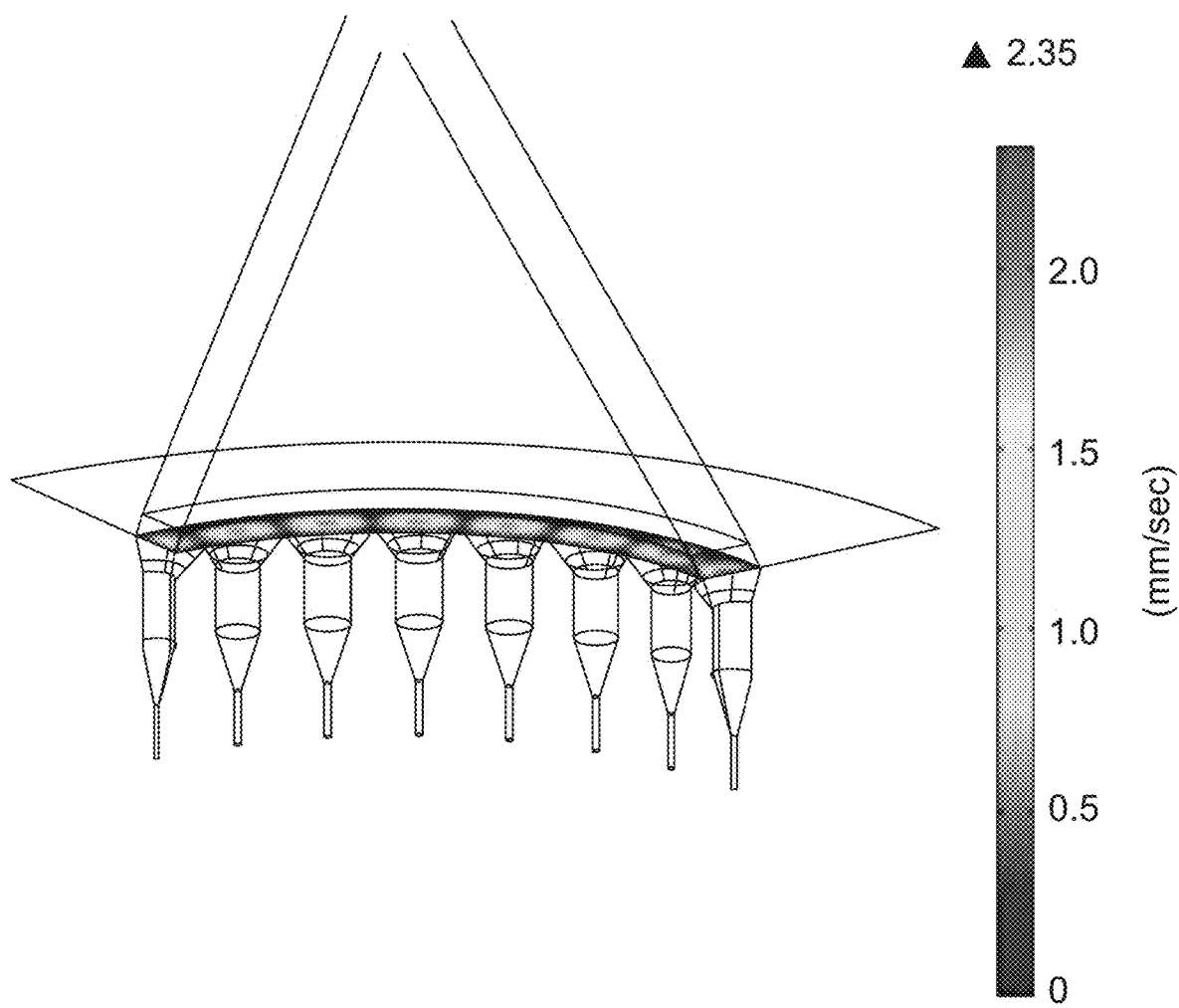
FIG. 22 illustrates a flow velocity profile of a polymer melt as it flows through the holes and across the polymer wetted surface of the spinneret shown in FIGS. 18A-18D.

FIG. 22 illustrates a flow velocity profile of a polymer melt as it flows through the holes and over the wetted area of the spinneret 206 shown and described above in FIGS. 18A-18D and 19A-19D. The flow velocity distribution of the polymer melt is significantly more uniform, as evidenced by much less stagnated flow (i.e., the dark blue area) within the wetted area than the flow velocity profile that is attained when using the prior art spinnerets shown in FIGS. 1-2 and 3-4 of the present patent application. Thus, the "dead area" of the inventive spinneret 206 of FIGS. 18A-18D and 19A-19D is relatively small, preferably about 12% or less, while the "dead area" of the prior art spinneret shown in FIGS. 1 and 2 is 90%, and the "dead area" of the spinneret shown in FIGS. 3 and 4 is as much as 43%.

A breaker plate is a component that directs a polymer melt into a proximal end of a die body of a polymer extrusion die assembly. The breaker plate is adapted to receive a filtering component, such as a filter screen. A breaker plate can also be designed to contain one or more mixing elements, such as ball bearings, placed into a hollow of a cylindrical wall that projects proximally from a proximal face of the breaker plate.

Figure 23A:
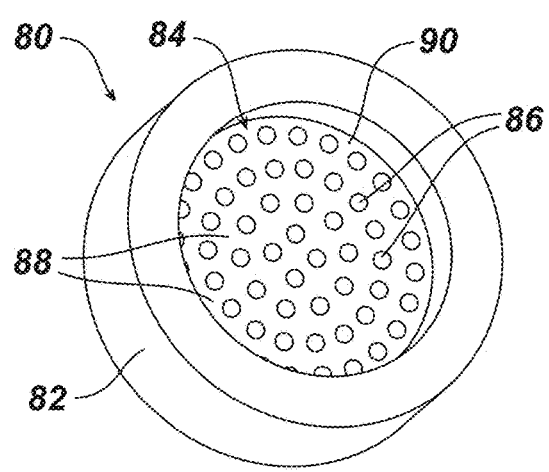
FIG. 23A is a perspective view of a prior art breaker plate used with a polymer extrusion die assembly.
Figure 23B:
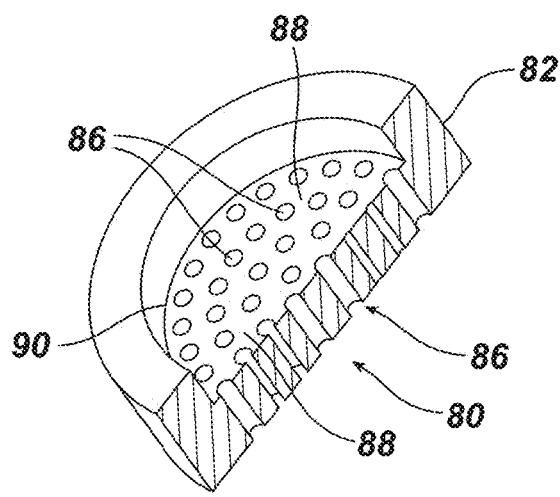
FIG. 23B is a cross-sectional view of the breaker plate shown in FIG. 23A.

Referring to FIGS. 23A and 23B, a conventional breaker plate 80 includes a cylinder 82 that defines a cylindrical hollow space 84 that is adapted to receive a filtering component such as a filter screen. The breaker plate 80 has holes 86 through which a polymer melt flows. A proximal surface of the breaker plate has flat surfaces 88 located between the holes 86. The flat surfaces 88 are also located at an outer perimeter 90 of the proximal surface of the plate. The flat surfaces 88, which comprise about 78.1% of the surface area of the proximal face of the plate, define dead zones in which the polymer melt cannot flow freely through the breaker plate 80. As the polymer melt flows through the breaker plate 80, the flowing polymer will stagnate in the dead zones, which will result in degradation of the polymer melt and the formation of weak suture strands.

Figure 24:
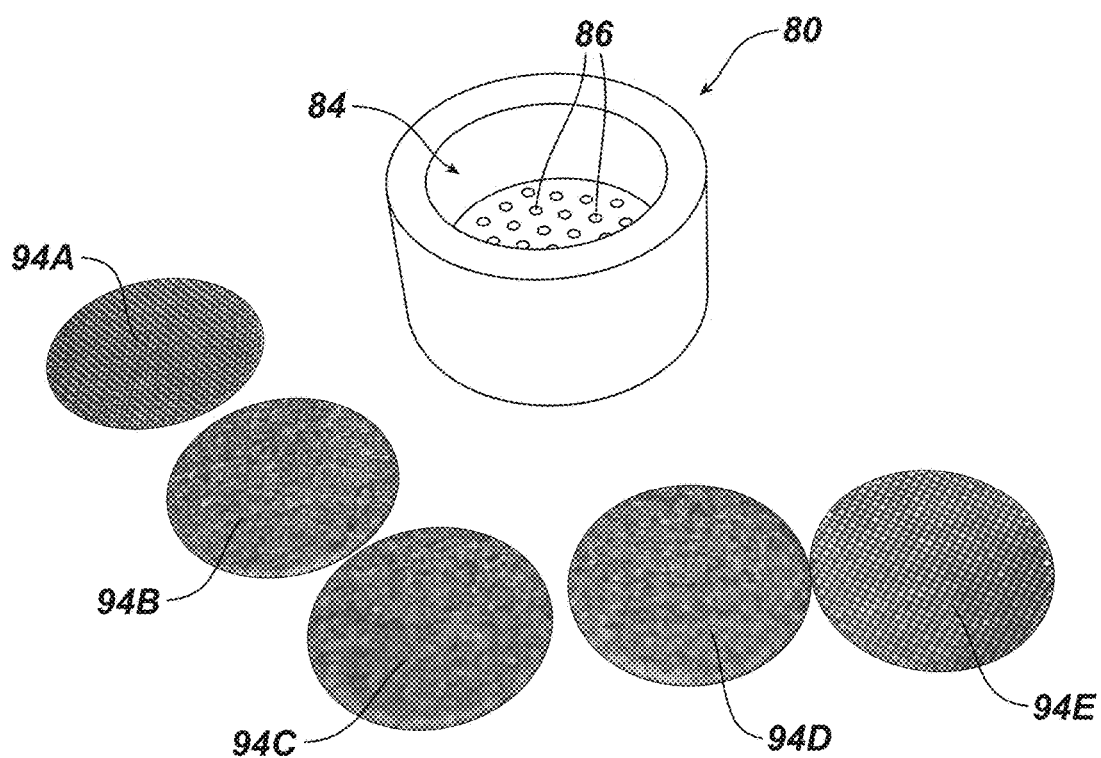
FIG. 24 is a perspective view of a prior art breaker plate and filtering screens that are placed into a cylindrical hollow space of the breaker plate.

FIG. 24 shows filtering elements 94A-94E (e.g., filtering screens) that are placed into the cylindrical hollow space 84 of the breaker plate 80 for covering the proximal surface of the breaker plate 80 and the holes 86 formed in the breaker plate. The filtering elements 94A-94E are designed to remove impurities that are present in the polymer melt.

FIG. 25A shows a die body 96 of a polymer extrusion die assembly. The die body 96 has an inlet opening 98 at a proximal end thereof that is adapted to receive a polymer melt after it has passed through the breaker plate 80 (FIG. 24). Referring to FIG. 25B, the breaker plate 80 (FIG. 24) is assembled with the die body 96 so that the cylinder 82 of the breaker plate 80 is aligned with the inlet opening 98 (FIG. 25A) of the die body 96. One or more mixing elements 99, such as stainless steel ball bearings, may be disposed within the cylindrical hollow space 84 (FIG. 24) of the breaker plate 80 for mixing the polymer melt as it passes through the breaker plate.

As noted above, conventional breaker plates have flat surfaces and/or dead zones on the proximal surface of the breaker plate that result in the degradation of the polymer melt as it flows through a polymer extrusion die assembly. There have been a number of efforts directed to minimizing the presence of dead zones between the holes of breaker plates. For example, U.S. Pat. Nos. 3,938,925 and 5,650,067 disclose breaker plates in which entrances to flow holes are enlarged in the central areas of the breaker plates in order to decease the presence of dead zones. In spite of these advances, conventional breaker plates still have a significant number of flat surfaces that are located along the corners and/or along the perimeter of the proximal surface of the breaker plate. Moreover, the inlets for the polymer melt flow holes or flow channels typically have ridges that define peaks, which fail to properly support filtering elements (e.g., filtering screens) when they are under high pressure during polymer extrusion processes.

Thus, in spite of the above efforts, there remains a need for improved breaker plates that substantially eliminate dead zones at the proximal surface of the breaker plate to minimize polymer degradation. There also remains a need for breaker plates that have structure for adequately supporting filters without the risk of the filters collapsing and/or deforming when under high pressure.

Figure 26A:
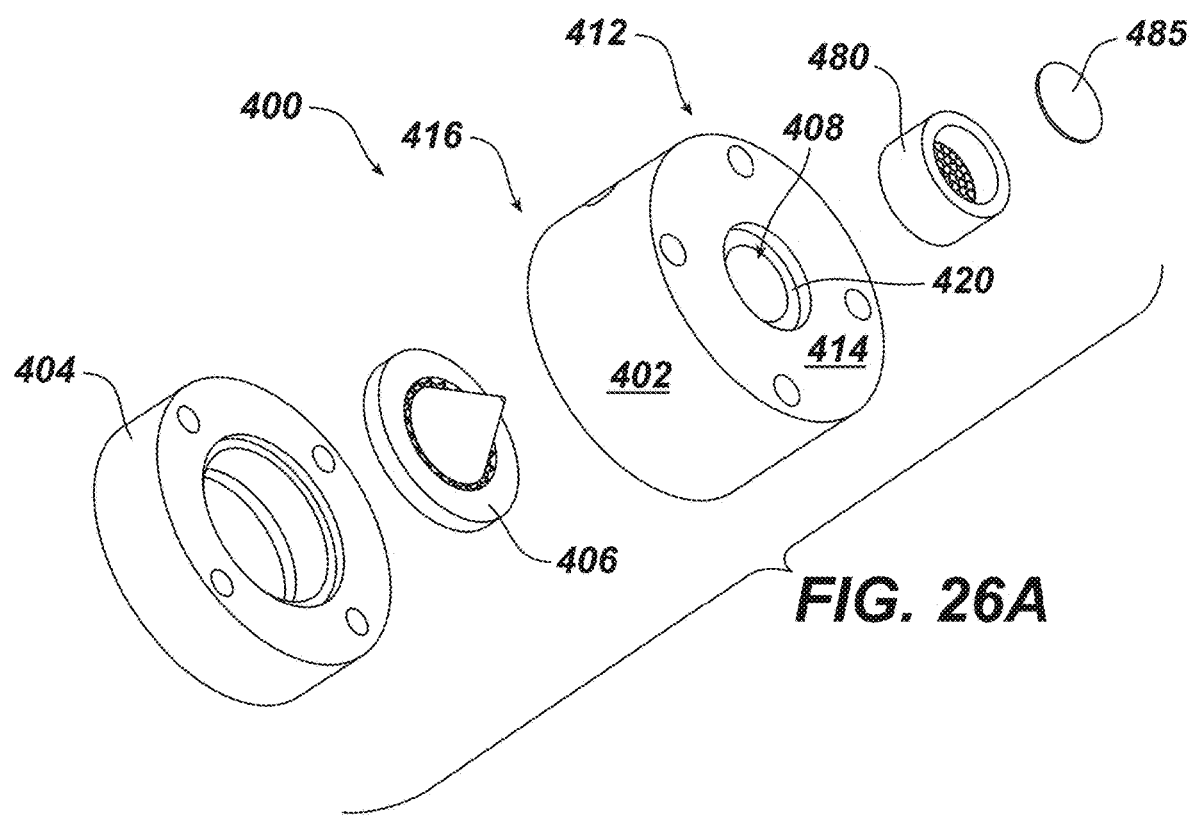
FIG. 26A is an exploded view of the polymer extrusion die assembly including a breaker plate, a die body, a spinneret, and a die retainer ring, in accordance with one embodiment of the present patent application.
Figure 26B:
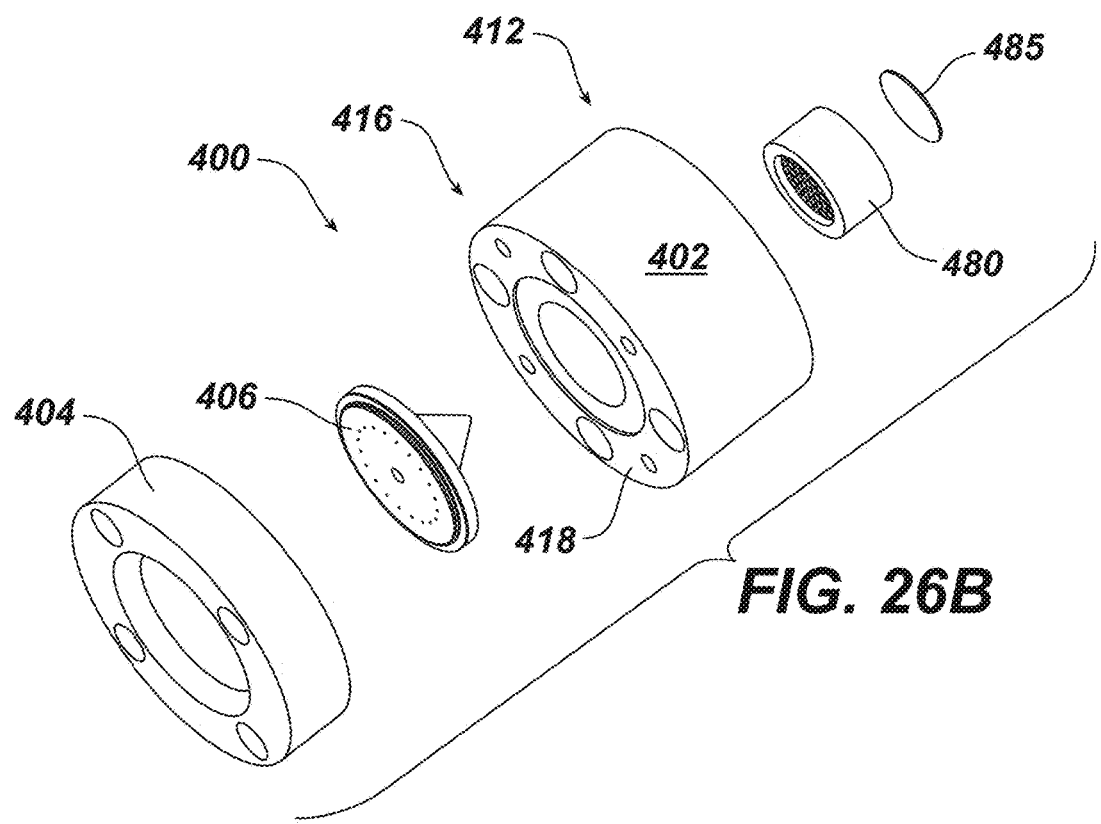
FIG. 26B is another exploded view of the polymer extrusion die assembly shown in FIG. 26A.
Figure 27A:
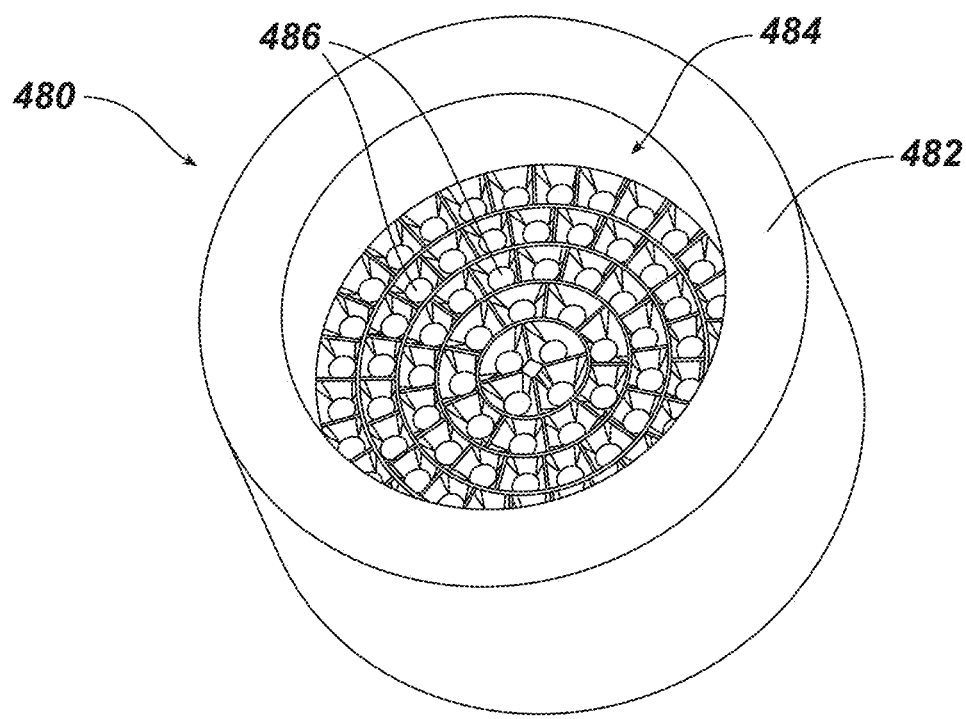
FIG. 27A is a perspective view of a proximal end of the breaker plate shown in FIGS. 26A and 26B.
Figure 27B:
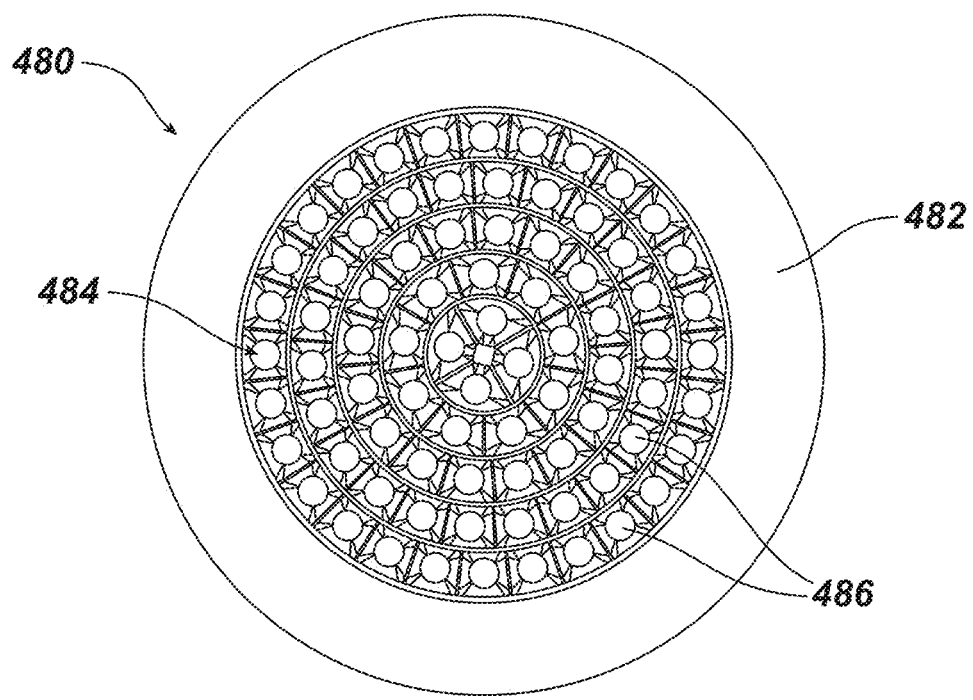
FIG. 27B is a proximal end view of the breaker plate shown in FIG. 27A.
Figure 27C:
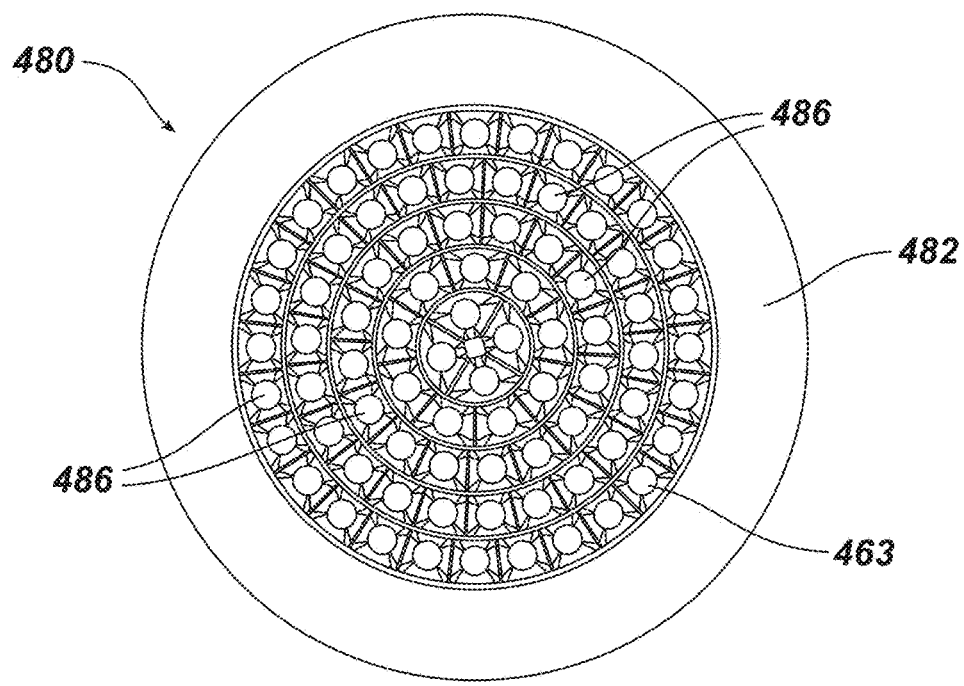
FIG. 27C is a distal end view of the breaker plate shown in FIGS. 27A and 27B.
Figure 27D:
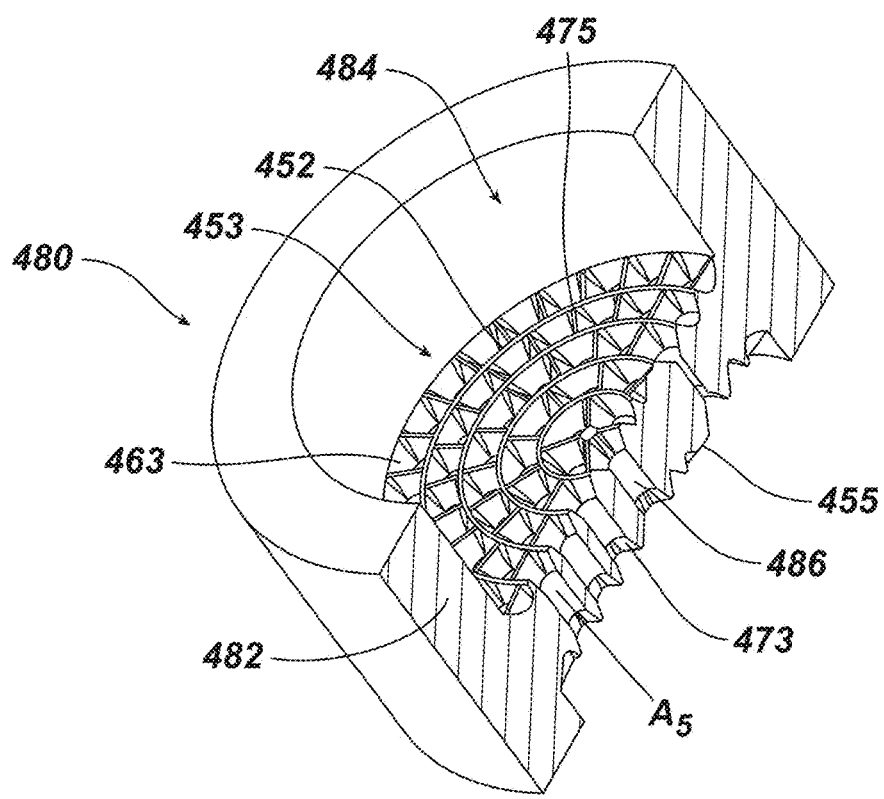
FIG. 27D is a cross-sectional view of the breaker plate shown in FIGS. 27A-27C.
Figure 28:
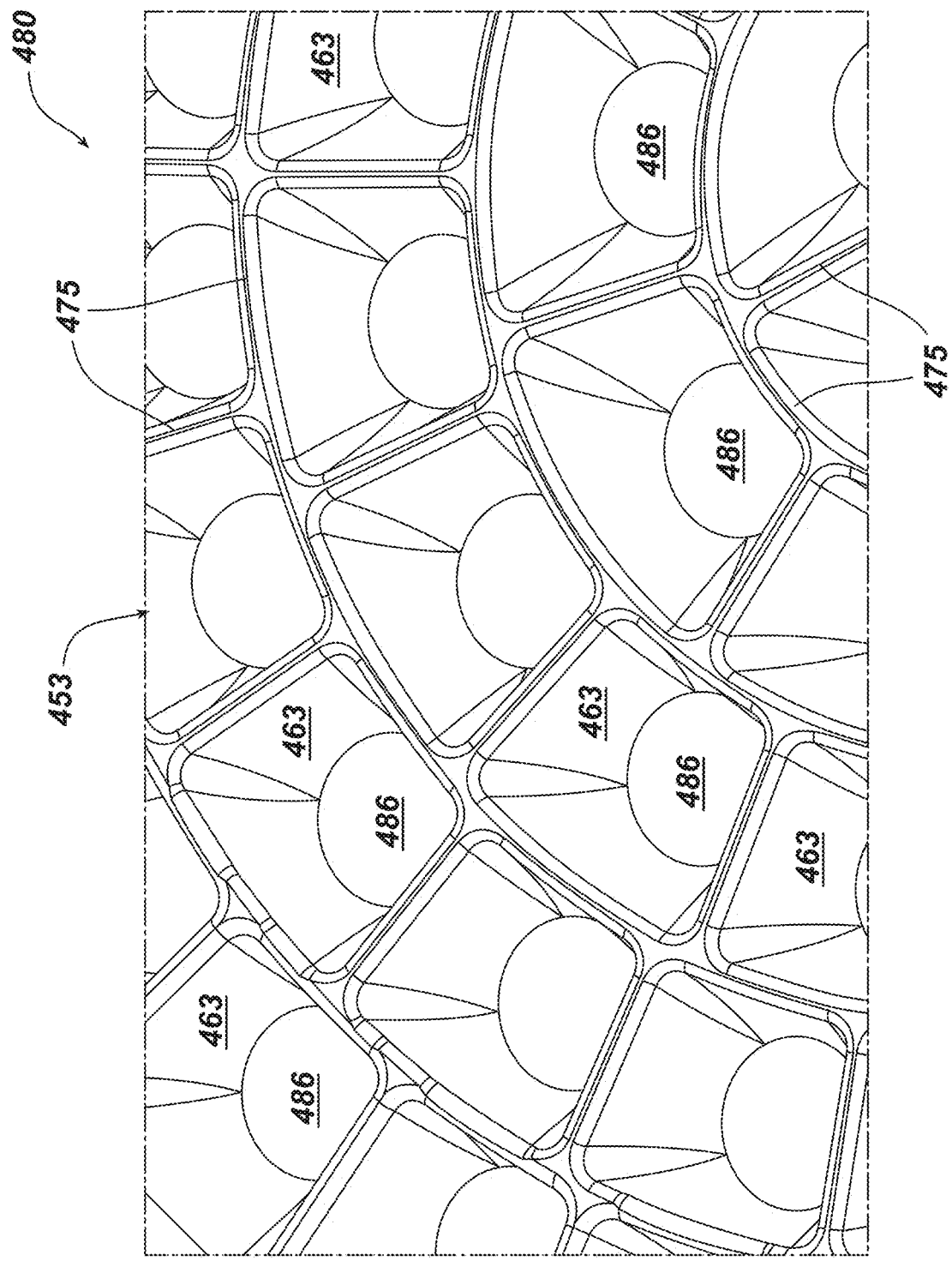
FIG. 28 is a perspective view of a section of the proximal surface of the breaker plate shown in FIGS. 27A-27E including contoured entrance zones and holes passing through the breaker plate, in accordance with one embodiment of the present patent application.

Referring to FIGS. 26A and 26B, in one embodiment, a polymer extrusion die assembly 400 preferably includes a die body 402, a die retainer ring 404, a spinneret 406, a breaker plate 480, and a filtering element 485. The polymer extrusion die assembly 400 is preferably adapted for receiving a polymer melt at a proximal end thereof and dispensing filaments or fibers from a distal end thereof, whereby the extruded fibers may be used for making sutures. The die body 402, the die retainer ring 404, and the spinneret 406 may have one or more of the structural features disclosed in the other embodiments that are disclosed in the present patent application. For example, the die body 402 may be similar to the die body 102 shown and described above in FIGS. 8A-8D and 9A-9B, the die retainer ring 404 may be similar to the die retainer ring 104 shown and described above in FIGS. 10A-10D and 11A-11B, and the spinneret 406 may be similar to the spinneret 106 shown in FIGS. 12A-14C, the spinneret 206 shown in FIGS. 18A-19D, and/or the spinneret 306 shown in FIGS. 20A-21D.

In one embodiment, the die body 402 preferably includes a proximal end 412 with a flat top surface 414 and a distal end 416 with a flat bottom surface 418. The proximal end 412 of the die body 402 desirably includes a proximal inlet opening 408 for directing a polymer melt into the proximal end of the die body. In one embodiment, the die body 402 of the polymer extrusion die assembly 400 preferably includes a top groove 420 having an annular shape that is formed in the top surface 414 of the die body and that surrounds the proximal opening 408 of the polymer extrusion die assembly 400.

In one embodiment, the breaker plate 480 is seated in the top groove 420 that is located at the proximal end of the die body 402. In one embodiment, the breaker plate 480 is preferably disposed within a polymer flow passage, wherein it is located between a polymer outlet of a pump block (not shown) and the inlet opening 408 of the die body 402. In one embodiment, the breaker plate 480 preferably mixes, homogenizes and/or filters the polymer melt before it floes into the inlet opening 408 of the die body 402.

Referring to FIGS. 27A-27E, in one embodiment, the breaker plate 480 preferably includes a cylinder 482 that defines a cylindrical hollow space 484 that is adapted to receive filtering and/or mixing components. The filtering components may include filtering screens and the mixing components may include a plurality of ball bearings (e.g., stainless steel ball bearings). The breaker plate 480 preferably has a plurality of flow holes 486 formed in the plate that are spaced from one another and that extend between a proximal (inlet) surface 452 and a distal (outlet) surface 455 of the plate for enabling a polymer melt to flow through the breaker plate. In one embodiment, each flow hole 486 preferably has a proximal end, a distal end, and a central axis $A_5$ that extends from the proximal end to the distal end. In one embodiment, the central axis $A_5$ may be perpendicular to planes defined by the respective proximal and distal surfaces 442, 445 of the breaker plate.

In one embodiment, the breaker plate 480 may have 10-100 flow holes 486. In one embodiment, each flow hole 486 may have an inner diameter of about 1-4 mm and depth of about 5-10 mm for enabling a polymer melt to flow from the outlet of a polymer source, such as a metering pump block (not shown), to the inlet of an extrusion die assembly 400 (FIG. 26A).

Referring to FIGS. 27A-27E and FIG. 28, in one embodiment, the proximal surface 452 of the breaker plate 480 preferably includes a wetted area 453 that contains the spaced flow holes 486. In one embodiment, the breaker plate 480 desirably includes contoured entrance zones 463 that desirably surround and are in communication with the proximal ends of each of the respective flow holes 486. In one embodiment, each contoured entrance zone 463 preferably includes contoured surfaces that extend distally from the proximal surface 452 of the plate 480 to the proximal end of each flow hole 486 associated therewith. In one embodiment, each proximal contoured entrance zone 463 preferably has substantially no planar or flat surfaces normal to the central axis of the flow hole associated therewith.

In one embodiment, the contoured entrance zone 463 surrounding the proximal end of each flow hole 486 directly borders the contoured entrance zone 463 surrounding the proximal end of each adjacent flow hole 486 so that there are substantially no planar surfaces normal to the direction of the central axes $A_5$ of the respective flow holes 486 that remain between adjacent holes on the proximal surface 452 of the breaker plate 480. The contoured surfaces of the contoured entrance zones 463 may include sloping surfaces, and curved surfaces including concave curved surfaces and convexly curved surfaces.

In one embodiment, the proximal side of the breaker plate desirably includes ridges 475 that preferably surround the contoured entrance zones 463. The ridges 475 may have convexly curved surfaces that are substantially devoid of any flat or planar surfaces that are normal to the direction of the central axes $A_5$ of the respective flow holes 486. In one embodiment, the ridges 475 lie in the same plane on the proximal surface 452 of the breaker plate 480 (e.g., the proximal surface 452 of the plate). In one embodiment, the ridges 475 preferably contact and support a distal face of the filtering element 485 (FIG. 26A) to minimize the risk of deformation of the filtering element when the filtering element is exposed to high pressure during an extrusion process.

In one embodiment, the breaker plate 480 preferably includes the distal surface 455 and contoured exit zones 473 formed in the distal surface 455 that surround the distal ends of the respective flow holes 486. The contoured exit zones 473 preferably extend between the distal ends of the flow holes 486 and the distal surface 455 of the plate. The contoured exit zones 473 preferably have substantially no flat surfaces normal to the central axes $A_5$ of the respective flow holes. The contoured entrance zones 463 formed in the proximal surface of the breaker plate and the contoured exit zones 473 formed in the distal surface of the breaker plate 480 desirably provide a dead-zone-free breaker plate that will desirably minimize polymer degradation, improve fiber uniformity and significantly increase the strength of the fibers or sutures produced.

In one embodiment, the contoured entrance zones 463 and the contoured exit zones 473 have substantially no planar or flat surfaces normal to the direction of the central axes $A_5$ of the respective flow holes 486, thereby eliminating and/or minimizing the presence of dead areas within the wetted areas of the proximal and distal surfaces 452, 455 of the breaker plate 480.

In one embodiment, after the breaker plate 480 is disposed between a pump block (not shown) and the proximal end of the die body 402 (FIG. 26A), a polymer melt may be forced into the proximal end of the breaker plate 480, whereupon the polymer melt flows in series into the cylindrical hollow space 484, over the contoured entrance zones 463, through the flow holes 486, over the contoured exit zones 473, and into the inlet opening 408 of the die body 402 (FIG. 26A).

The breaker plate 480 preferably has the hollow space 484 inside the tubular wall 482 that is directly connected with the proximal surface 452 of the plate. In one embodiment, polymer mixing and/or filtering elements, such as stainless steel balls, sintered and/or wire mesh screens, may be held within the hollow space 484 to homogenize the polymer melt and/or to filter impurities from the polymer stream. The tubular wall 482 of the breaker plate 480 may have an outer diameter $OD_9$ of about 2-5 cm, a wall thickness $T_1$ of 2-8 mm, a height $H_1$ of about 1-4 cm, and an inner diameter $ID_1$ that is equal to the outer diameter $OD_{10}$ of the proximal surface 452 of breaker plate 480.

In one embodiment, the tubular wall 482 has a proximal surface 485 and distal surface 495, which may serve as sealing faces when the breaker plate is installed in a polymer passage line. The distal surface 455 of the breaker plate 480 may be slightly recessed with respect to the distal sealing surface 495.

Figure 29A:
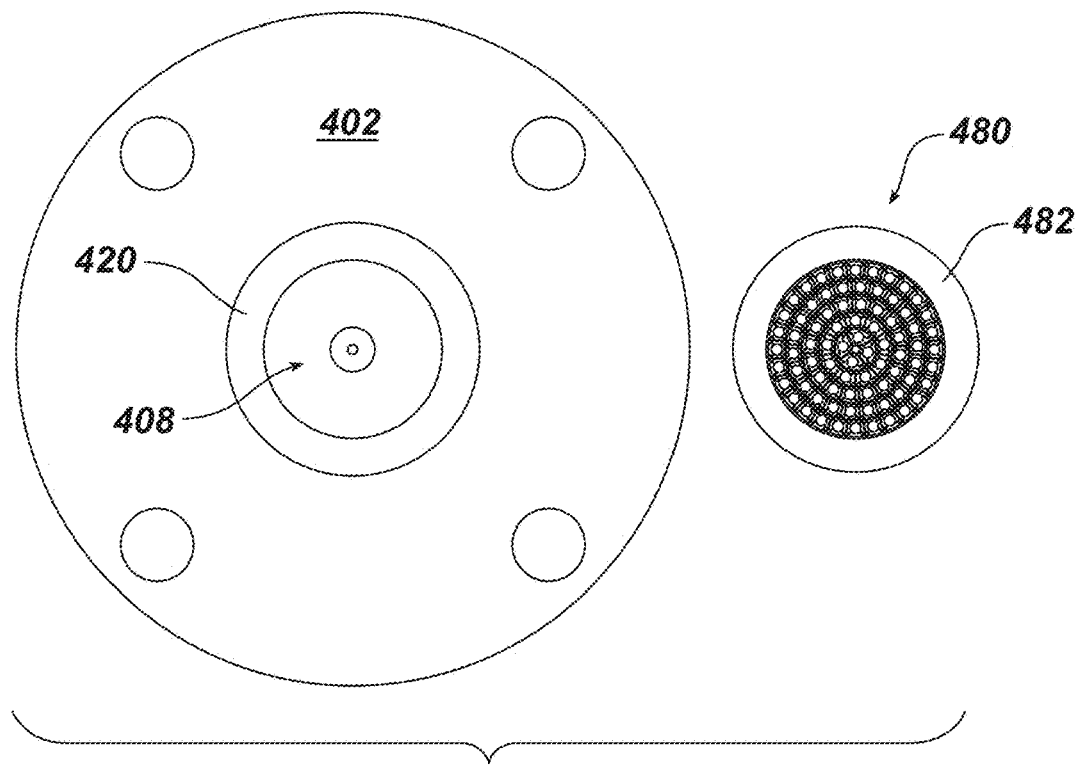
FIG. 29A is a proximal end view of a die body and a breaker plate adapted to be assembled with the die body, in accordance with one embodiment of the present patent application.
Figure 29B:
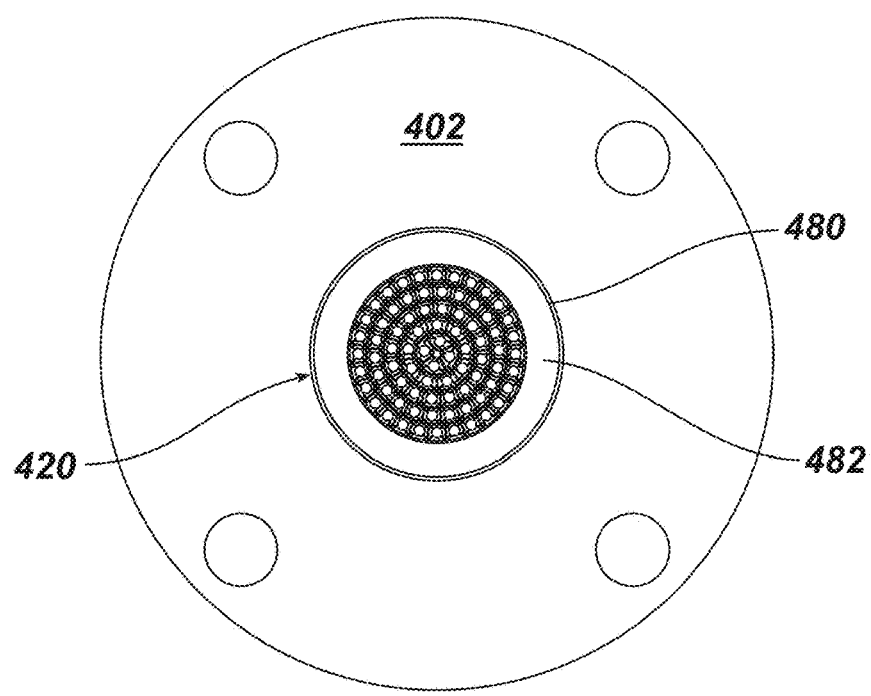
FIG. 29B shows the breaker plate of FIG. 29A assembled with the proximal end of the die body shown in FIG. 29A.
Figure 29C:
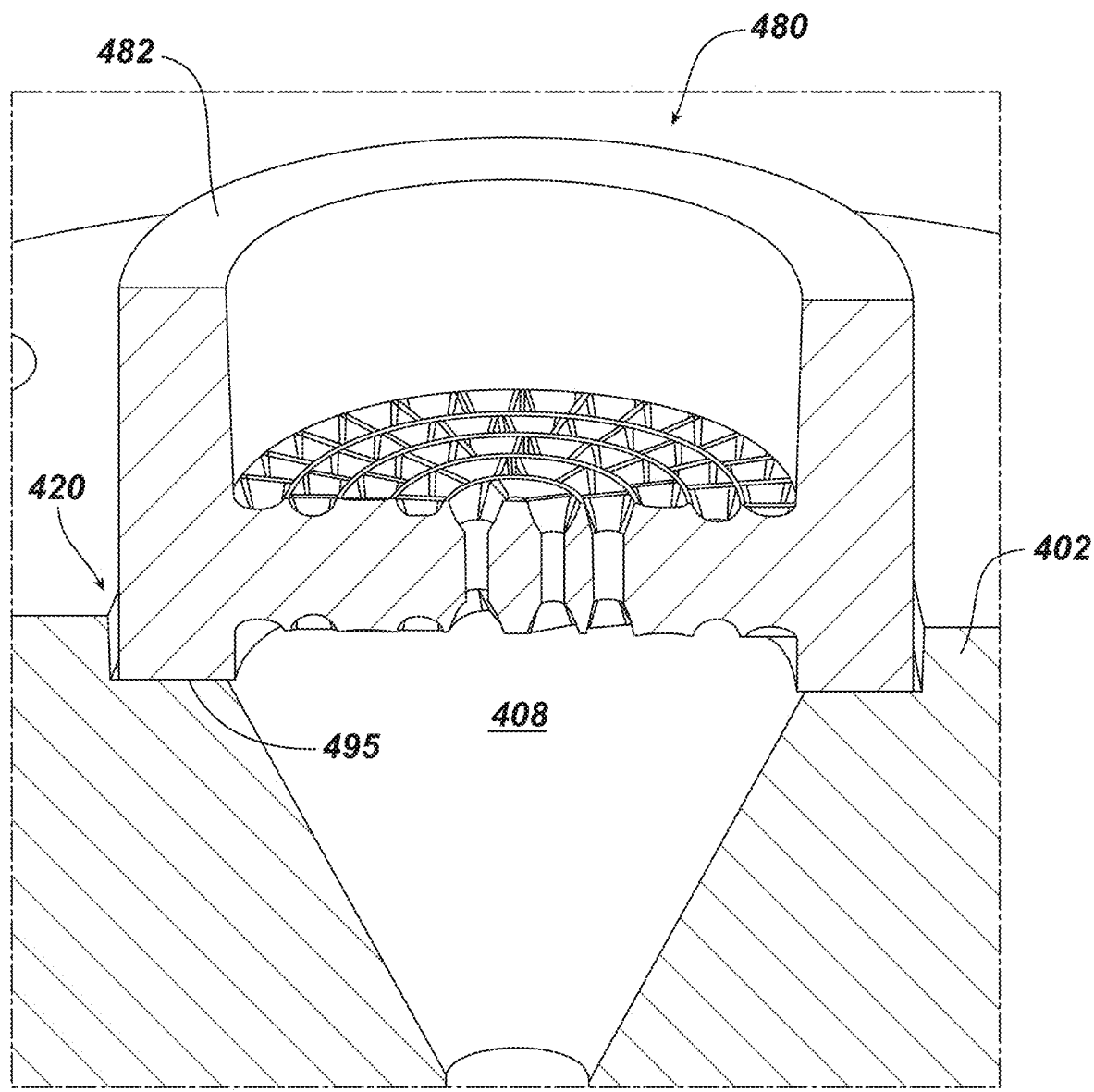
FIG. 29C is a cross-sectional view of the breaker plate and the die body of FIG. 29B.

Referring to FIGS. 29A-29C, in one embodiment, the breaker plate 480 is preferably assembled with the inlet opening 408 of the die body 402. The die body includes an annular groove 420 that surrounds the inlet opening 408, which is adapted to seat the distal sealing surface 495 at the distal end of the cylindrical wall 482 of the breaker plate. FIG. 29A shows the breaker plate 480 before it is seated in the annular grove 420 of the die body 402. FIGS. 29B and 29C show the breaker plate 480 after it has been seated in the annular groove 420 of the die body 402. The holes 486 of the breaker plate are preferably aligned with the inlet opening 408 of the die body 402.

Figure 30A:
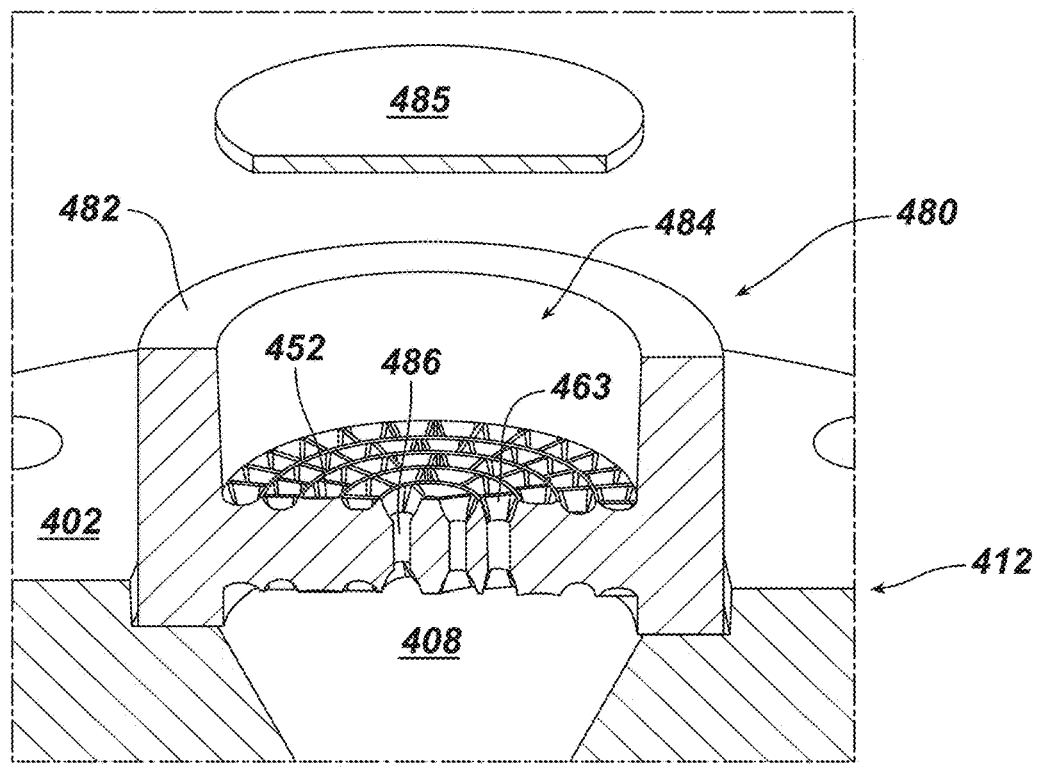
FIG. 30A illustrates a first stage of a method of inserting a filtering screen into a cylindrical hollow space of a breaker plate, in accordance with one embodiment of the present patent application.
Figure 30B:
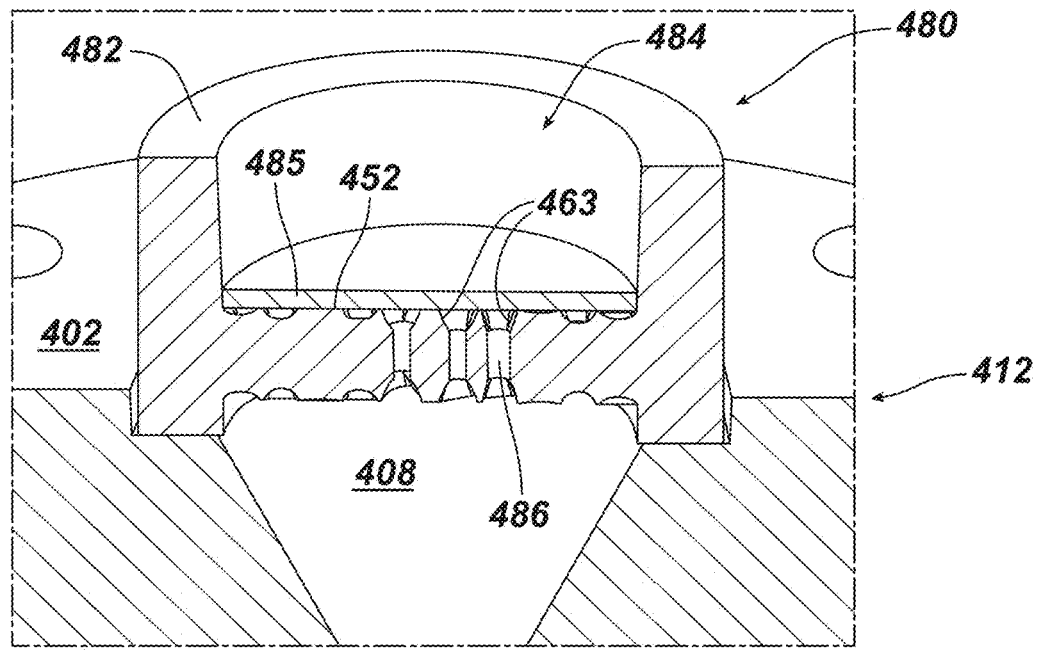
FIG. 30B illustrates a second stage of a method of inserting a filtering screen into a cylindrical hollow space of a breaker plate, in accordance with one embodiment of the present patent application.
Figure 30C:
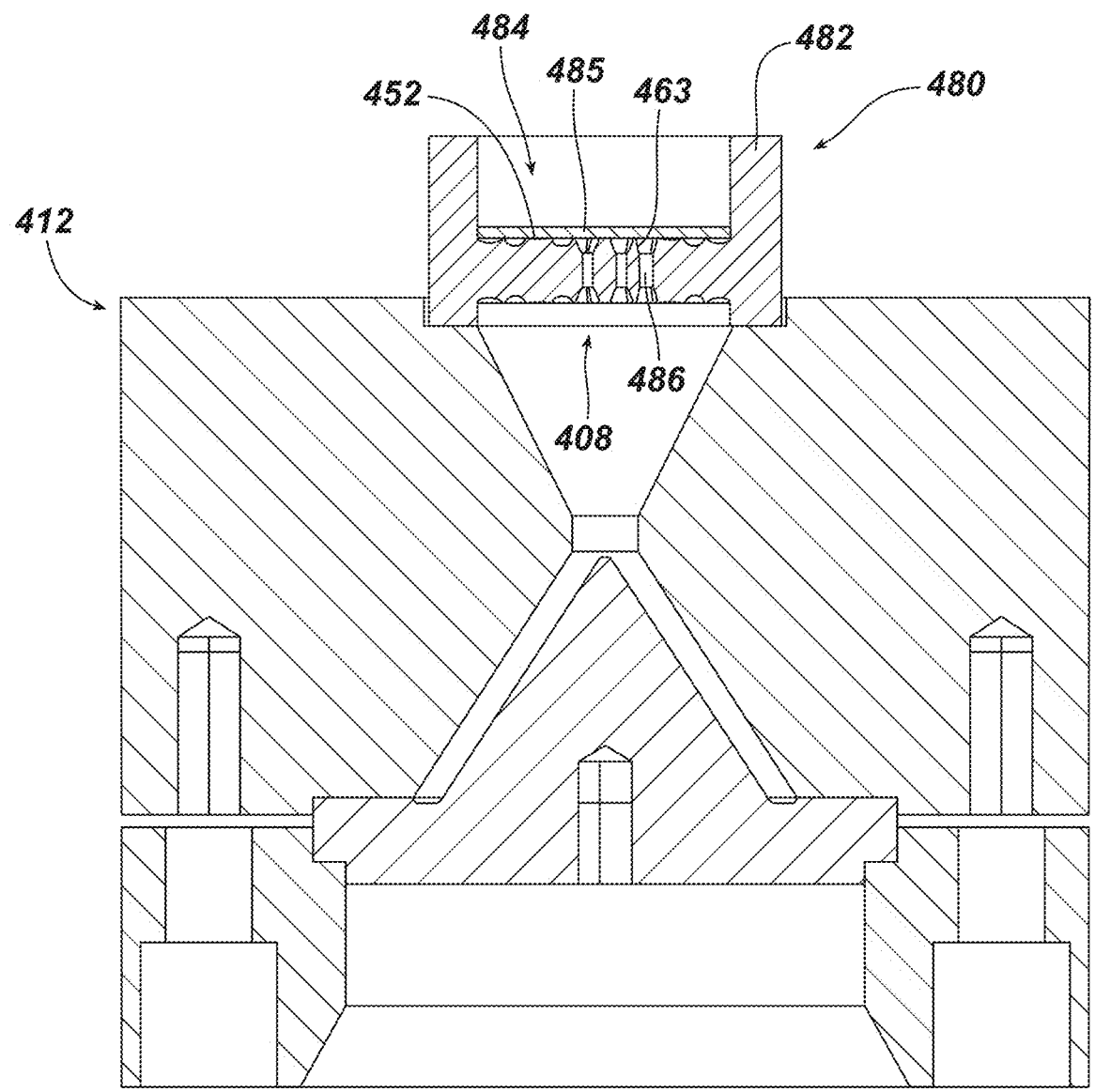
FIG. 30C is a cross-section view of a polymer extrusion die assembly including the breaker plate and the die body of FIG. 30B assembled with a spinneret and a die retainer ring, in accordance with one embodiment of the present patent application.

Referring to FIGS. 30A-30C, in one embodiment, with the breaker plate 480 assembled with the inlet opening 408 at the proximal end 412 of the die body 402 of the polymer extrusion die assembly 400, a filtering element 485, such as a filtering screen, may be inserted into the cylindrical hollow space 484 that is surrounded by the cylindrical wall 482 of the breaker plate 480. In one embodiment, the filtering element 485 preferably has an outer diameter that substantially matches the inner diameter of the cylindrical wall 482 so that the filtering element 485 completely covers the proximal surface 452 of the breaker plate 480, as well as the contoured inlet zones 463 and the flow holes 486 of the breaker plate.

Conventional cone die bodies remain deficient because they typically have large hollow spaces in the upper sections of the cone die bodies. For example, FIG. 31 shows a conventional die body having a large hollow, cone-shaped space in the upper section of the die body, which causes slow polymer flow and longer residence time that can lead to undesirable polymer degradation resulting in weak or broken filaments.

Another problem with conventional cone die body is poor heat transfer between the die body and the polymer melt that flows through the die body. The die zone temperature is usually set and controlled to an optimum specification for fiber extrusion. The inlet polymer temperature depends on the temperature of the polymer source that is provided from an extruder or a pump block, which is normally set to a different temperature than the temperature of the die body. As a result, the temperature of the polymer melt from the polymer source could be significantly colder or hotter than the temperature of the die body. Poor heat transfer between the die body and the polymer melt will prevent the attainment of an homogeneous equilibrium melt temperature before the streams of the polymer melt enter into the capillary holes of a spinneret, resulting in non-uniform fiber structure and/or other deficiencies.

Figure 32:
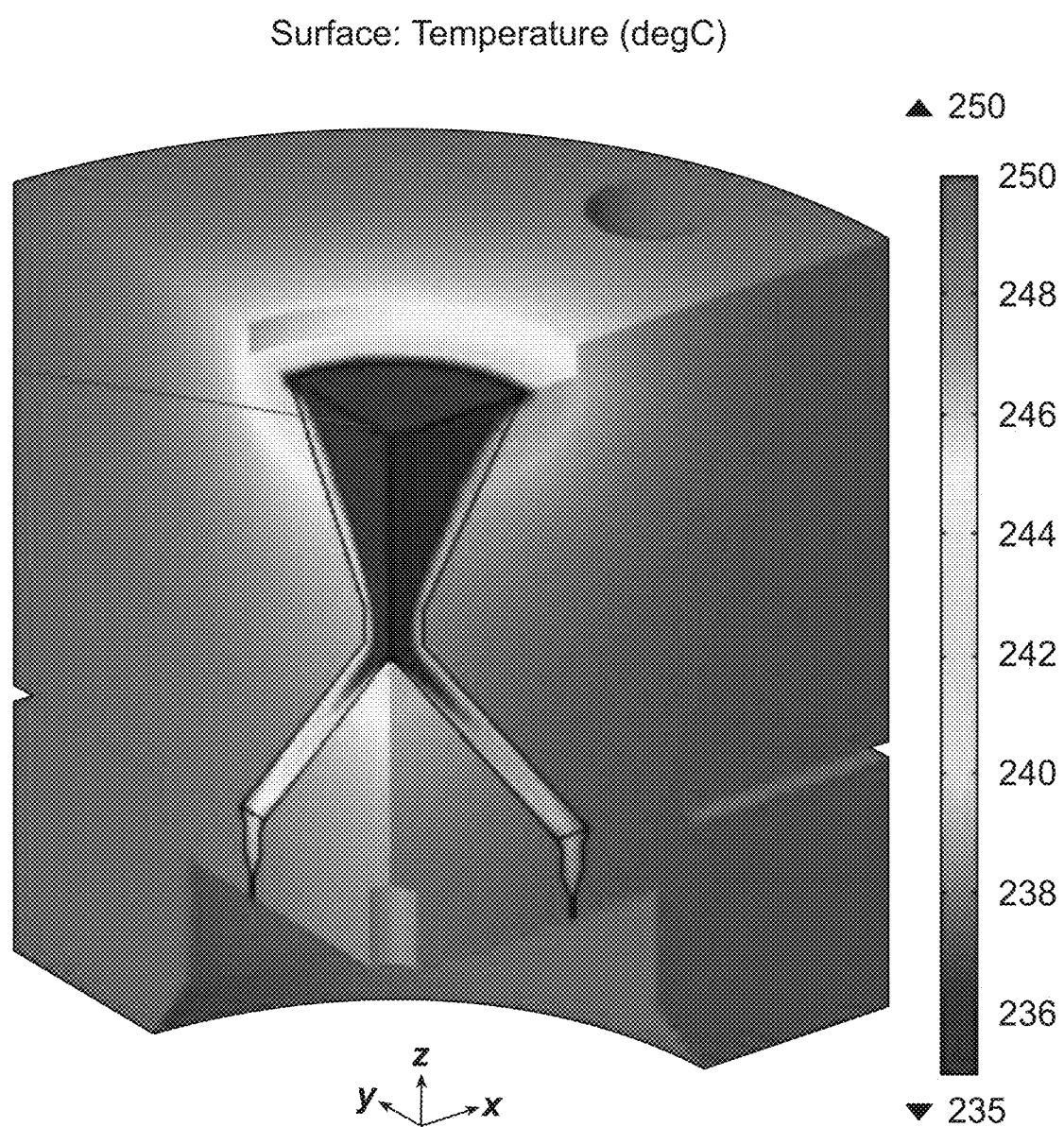
FIG. 32 is a cross-sectional view of another prior art die body.

FIG. 32 shows the results of a simulation in which the source polymer from a pump block is at about 235 degrees Centigrade when entering from the inlet of a cone die body. The temperature of a large portion of the polymer remains almost unchanged through the inverted cone space. The polymer temperature rises quickly only after reaching the lower part of the die body, where the polymer melt stream is split into a thin layer along the polymer melt flow passageway that is formed between the center cone of the die/spinneret and the hollow cone space of the die body. As a result of less than optimal heat transfer, it is difficult to heat the polymer melt to the preferred equilibrium temperature of 250 degrees Centigrade, which is a preferred extrusion temperature for the die body.

Figure 31:
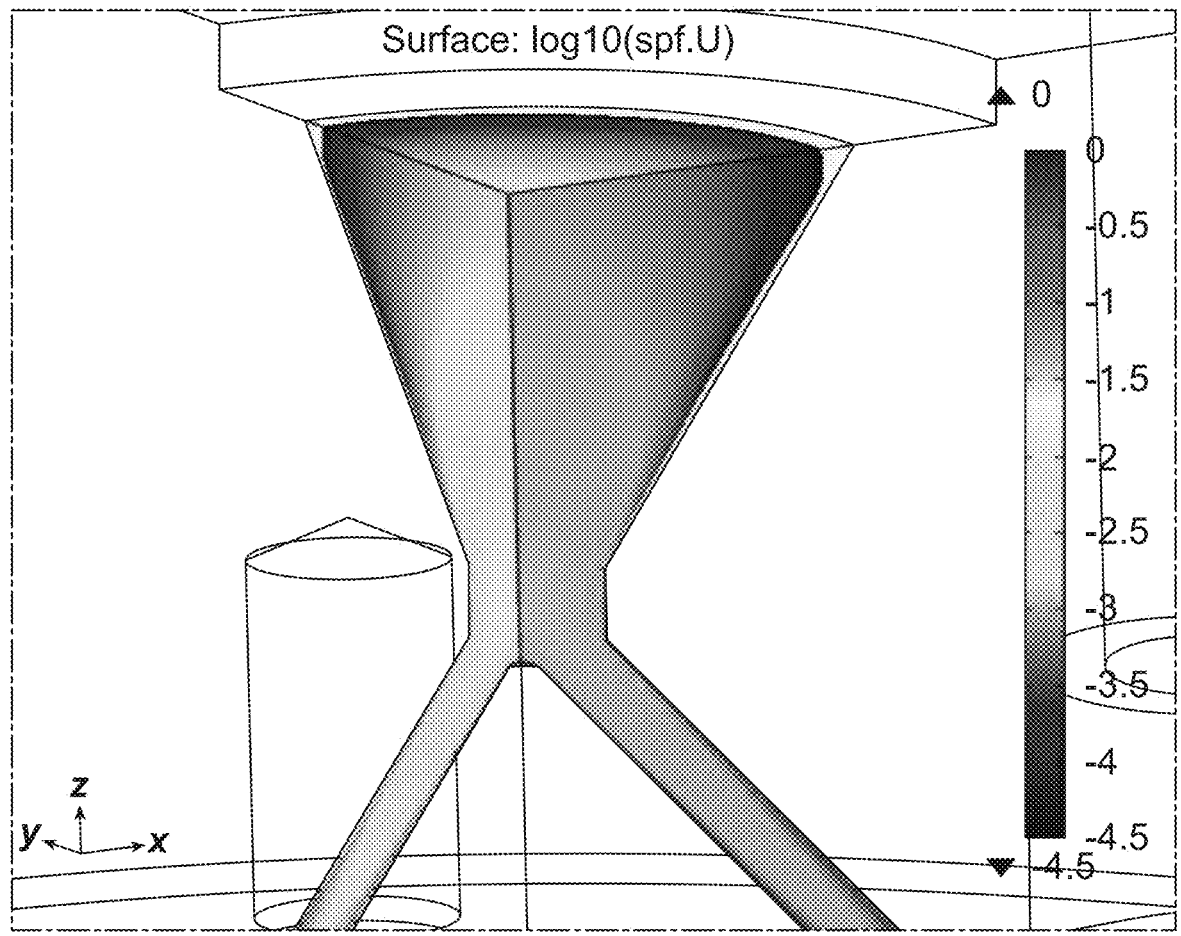
FIG. 31 is a cross-sectional view of a prior art die body.

In view of the above-noted deficiencies in the die bodies disclosed in FIGS. 31 and 32, there have been some efforts directed to improving heat transfer between die bodies and the polymer melt flowing through the die bodies. For example, U.S. Patent Application Publication No. 2002/0107326 discloses adding a cone to the downstream side of a breaker plate with the peak of the cone extending away from the breaker plate in the downstream direction. Flow channels are drilled through the center disk of the breaker plate, which contains a cone. The cone shaped center disk is designed to reduce the downstream flow volume by occupying part of the hollow space of the inverted cone in the die adapter. Unfortunately, heat transfer between the polymer streams and the die body or die adapter is not improved because the temperature of the cone shaped center disk is essentially the same as that of the source polymer flowing into the die body. As a result, heat is not easily transferred from or to the die adapter assembly, which makes it difficult to tightly control temperatures that are required for attaining optimum, uniform and stable fiber extrusion.

U.S. Pat. No. 4,072,457 discloses a spin pot for extruding fibers with polymer delivery channels drilled in a top cap in a branching-out fashion. The top cap has less total flow channel volume than a top cap having an inverted cone hollow space for polymer to flow from a small inlet to a breaker plate having an increased diameter. While the system disclosed in the '457 patent reduces the average residence time due to the decreased free volume in the top cap, a significant amount of flat surfaces are present on the exit side of the top cap. The flat surfaces are normal to the axis of the flow channels of the breaker plate beneath the top cap. As a result, the polymer at or near the flat surfaces of the top cap tends to stagnate or flow at a much slower speed than that flowing into the holes of the breaker plate near the outlets of the branching-out polymer delivery channels of the top cap. In addition to the potentially slower speed, the passage of the melt flow is significantly longer for the holes near the center areas than for the holes near the perimeter of the breaker plate where the outlets of the delivery channels are located. Thus, the residence time of the polymer passing through the spin pot is significantly different between the holes at different positions across the top cap. Longer residence time will generally lead to polymer degradation, poor fiber uniformity and/or poor tensile strength properties.

Thus, in spite of the above efforts, there remains a need for improved designs for die bodies that have reduced free volume, improved heat exchange features, and good homogeneity in the polymer melt stream before the polymer enters the capillary holes of an extrusion die/spinneret.

Figure 33A:
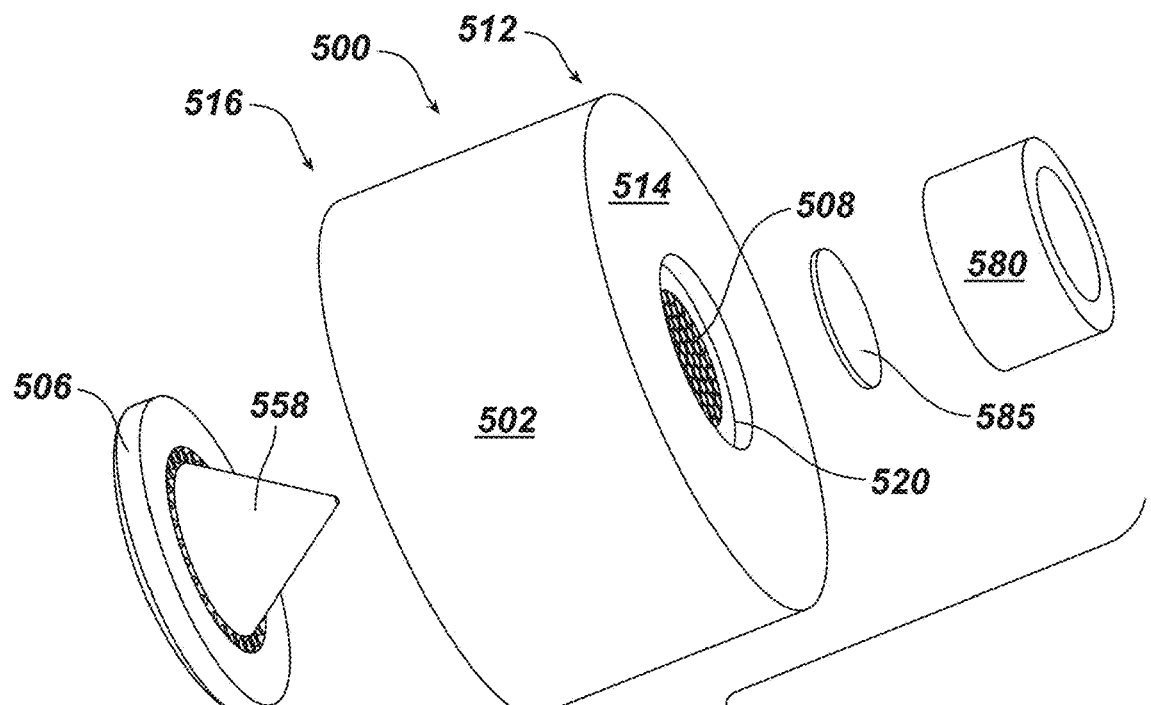
FIG. 33A is an exploded view of the polymer extrusion die assembly including a tubular adapter, a filtering screen, a die body, and a spinneret, in accordance with one embodiment of the present patent application.
Figure 33B:
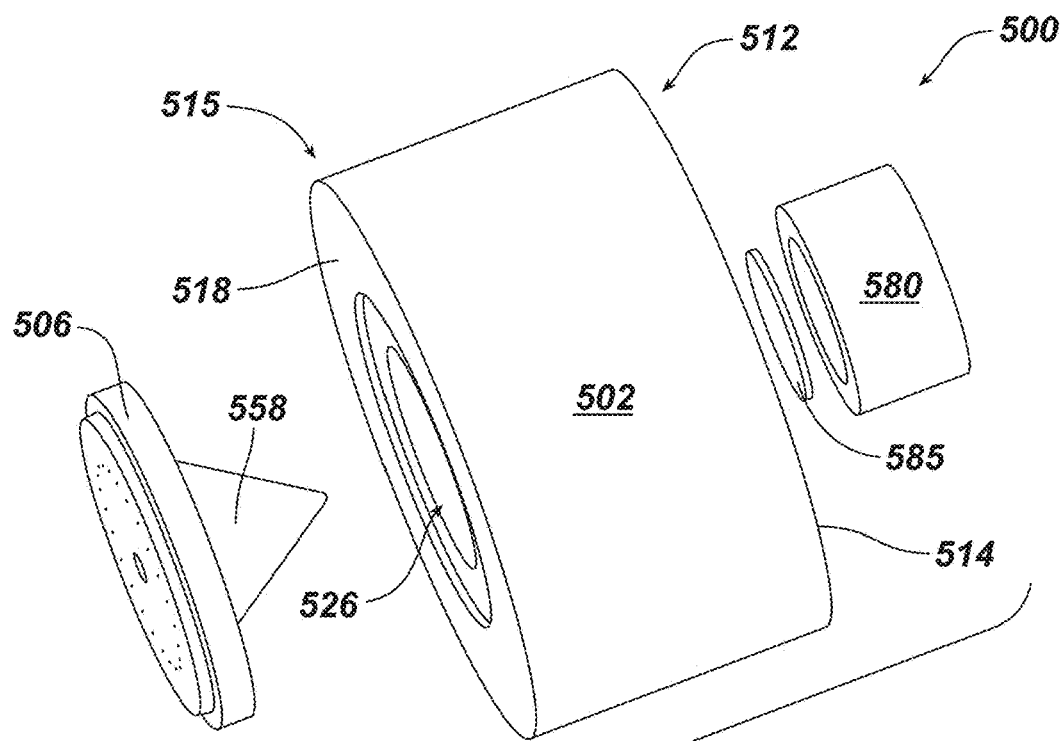
FIG. 33B is another exploded view of the polymer extrusion die assembly shown in FIG. 33A.

Referring to FIGS. 33A and 33B, in one embodiment, a polymer extrusion die assembly 500 preferably includes a die body 502, a spinneret 506, a tubular adapter 580, and a filtering element 585. The polymer extrusion die assembly 500 is preferably adapted for receiving a polymer melt at a proximal end thereof and dispensing filaments or fibers from a distal end thereof, whereby the extruded fibers may be used for making sutures. The die body 502 and the spinneret 506 may have one or more of the structural features described in the other embodiments that are disclosed in the present patent application. For example, the die body 502 may have one of more structural features that are similar to the die body 102 shown and described above in FIGS. 8A-8D and 9A-9B, and the spinneret 506 may be similar to the spinneret 106 shown in FIGS. 12A-14C, the spinneret 206 shown in FIGS. 18A-19D, and/or the spinneret 306 shown in FIGS. 20A-21D.

In one embodiment, the die body 502 preferably includes a proximal end 512 with a flat top surface 514 and a distal end 516 with a flat bottom surface 518. The proximal end 512 of the die body 502 desirably includes a proximal inlet opening 508 for directing a polymer melt into the proximal end of the die body. In one embodiment, the die body 502 of the polymer extrusion die assembly 500 preferably includes a top groove 520 having an annular shape that is formed in the top surface 514 of the die body and that surrounds the inlet opening 508 of the polymer extrusion die assembly 500.

In one embodiment, the distal end 516 of the die body 502 has a cone-shaped opening 526 that is adapted to receive the cone 558 of the spinneret 506 when the spinneret is assembled with the distal end of the die body 502.

In one embodiment, the tubular adapter 580 is adapted to be seated in the top annular groove 520 that is located at the proximal end 512 of the die body 502. In one embodiment, the tubular adapter 580 is preferably disposed within a polymer flow passage, wherein it is located between a polymer outlet of a pump block (not shown) and the inlet opening 508 of the die body 502. In one embodiment, the tubular adapter 580 may receive components for mixing, homogenizing and/or filtering the polymer melt before it flows into the inlet opening 508 of the die body 502. In one embodiment, the filtering element 585 is disposed inside the tubular element 580 for covering the inlet opening 508 at the proximal end 512 of the die body 502.

Referring to FIGS. 34A-34F, in one embodiment, the die body 502 preferably includes a plurality of flow channels 586 that extend between the inlet opening 508 at the proximal end 512 of the die body 502 and the cone opening 526 formed in the flat surface 518 at the distal end 516 of the die body 502. In one embodiment, the die body 502 desirably includes about 3-60 flow channels 586 that preferably extend between the inlet opening 508 and the cone opening 526. In one embodiment, the inlet opening 508 of the die body 502 preferably includes a plurality of contoured entrance zones 563 that are in communication with proximal ends of the respective flow channels 586. The inlet opening 508 desirably includes ridges 575 that extend between the contoured entrance zones 563, whereby the ridges 575 preferably lie in a common plane 552. Due to the presence of the contoured entrance zones 563 at the inlet opening 508 of the die body 502, within the area of the inlet opening, there are substantially no flat surfaces that are located between the proximal ends of the respective flow channels 586.

Figure 34A:
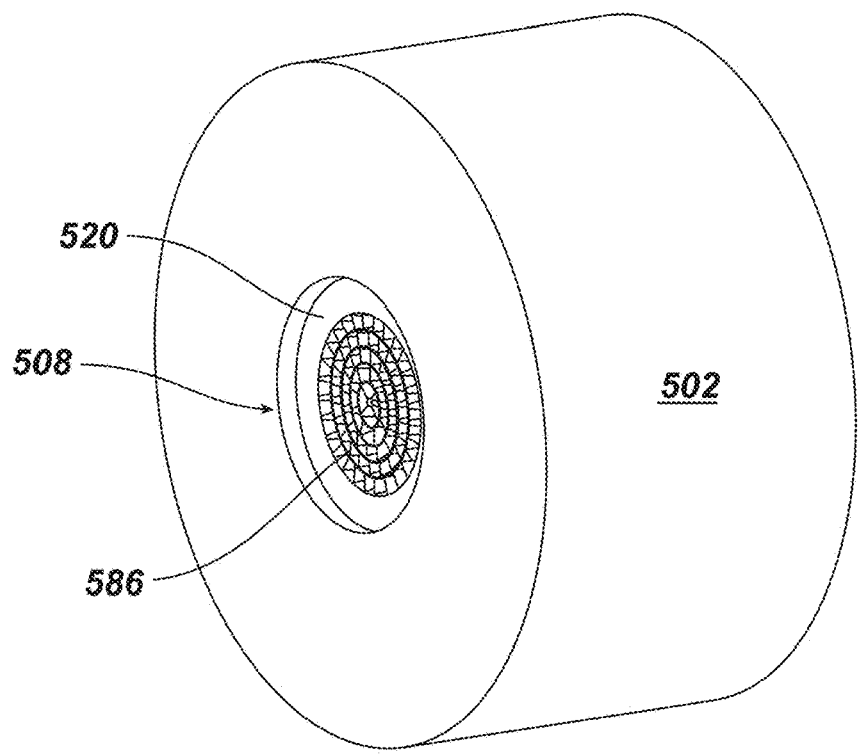
FIG. 34A is a perspective view of a proximal end of the die body shown in FIGS. 33A and 33B.
Figure 34B:
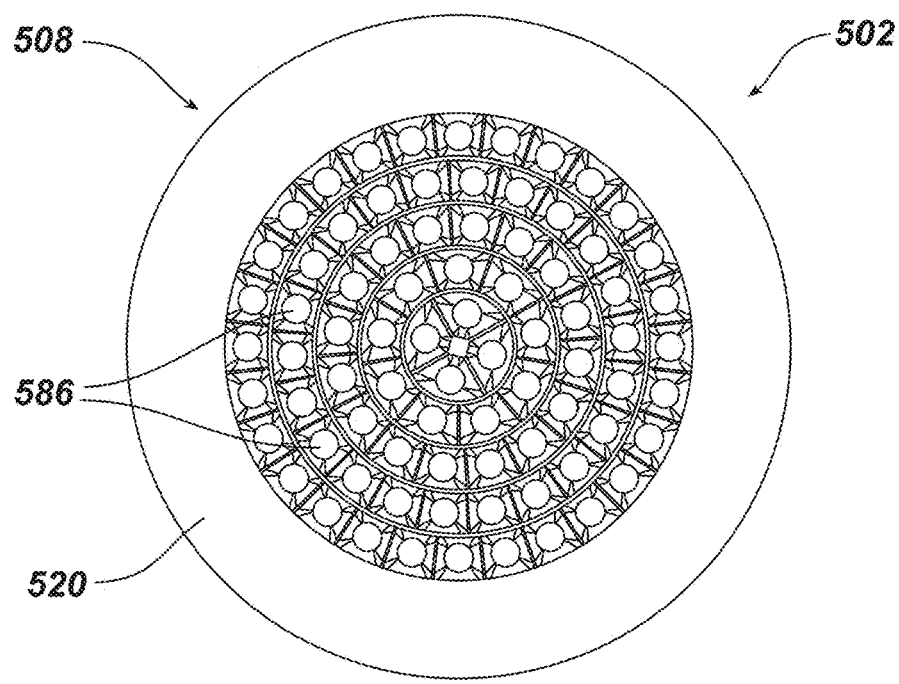
FIG. 34B is a proximal end view of the die body shown in FIG. 34A.
Figure 34C:
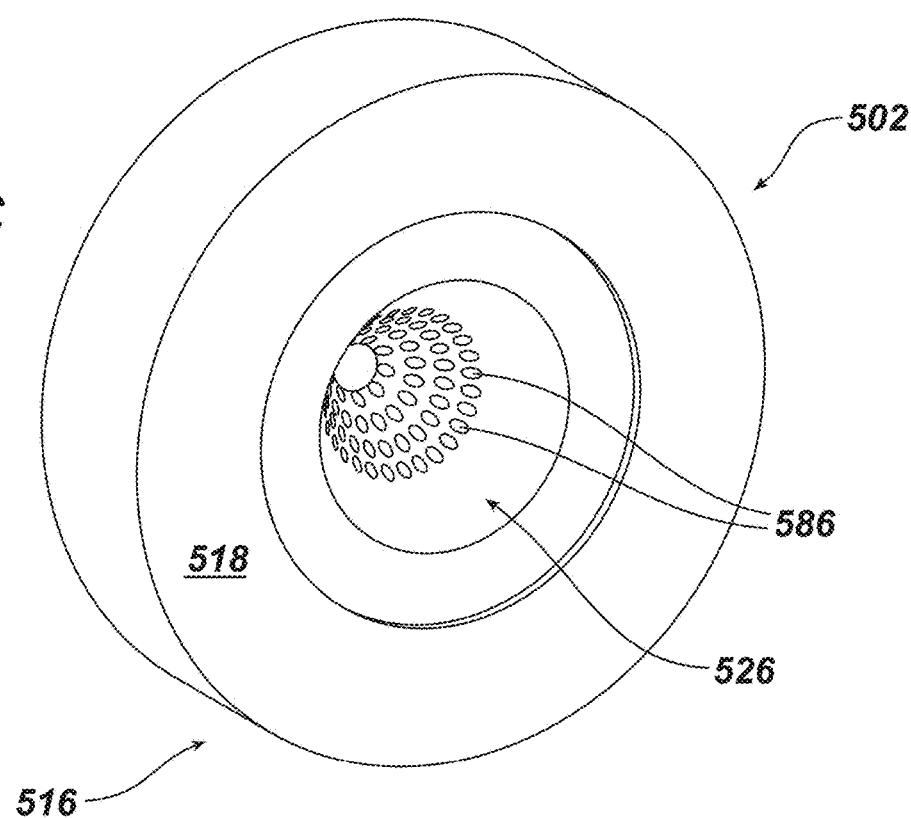
FIG. 34C is a perspective view of a distal end of the die body shown in FIGS. 34A and 34B.
Figure 34D:
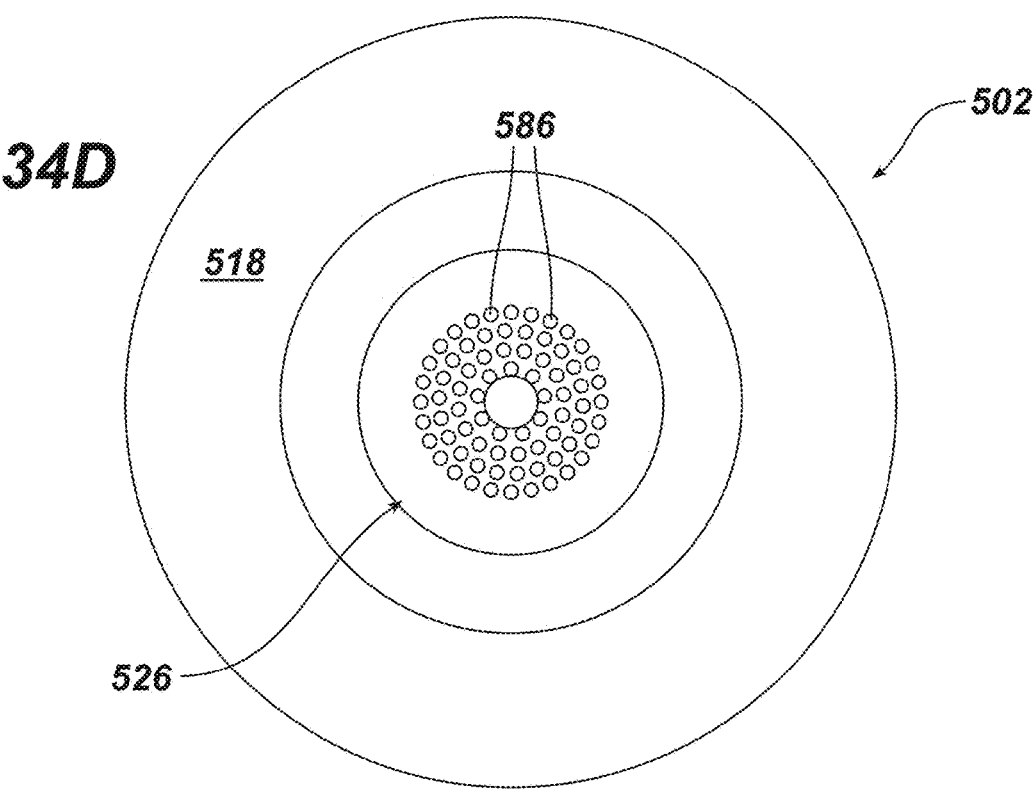
FIG. 34D is a distal end view of the die body shown in FIGS. 34A-34C.
Figure 34E:
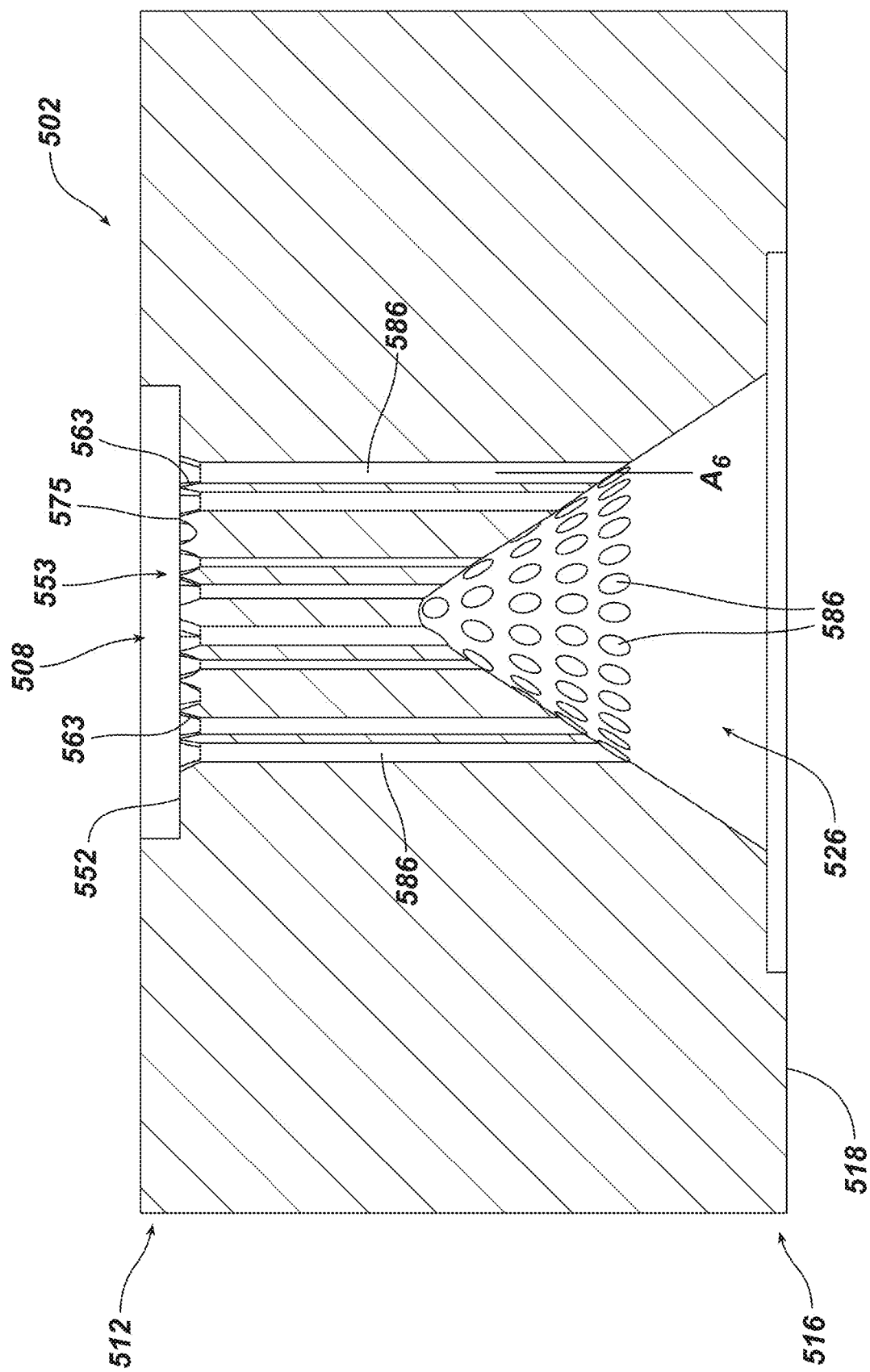
FIG. 34E is a cross-sectional view of the die body shown in FIGS. 34A-34D.
Figure 34F:
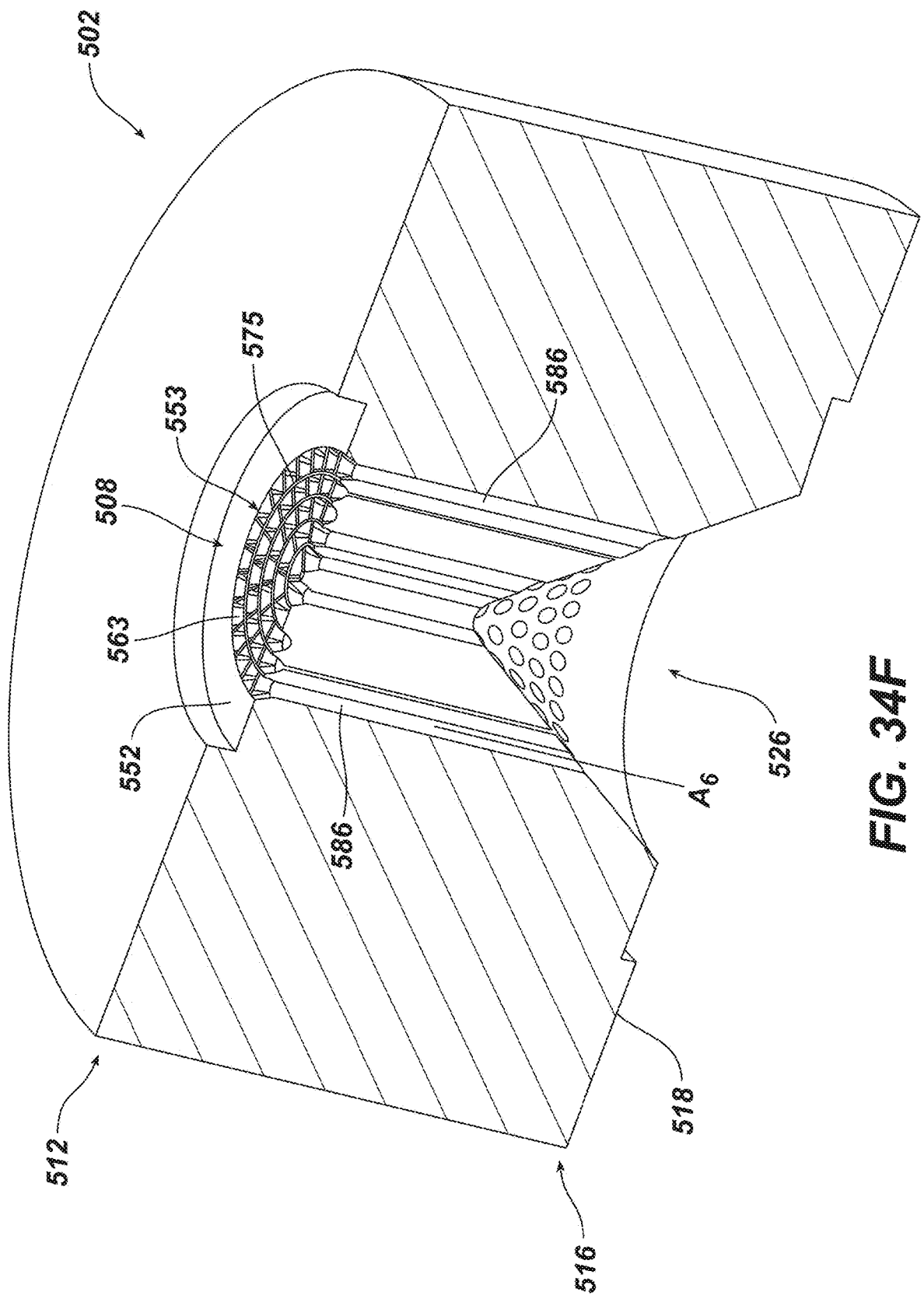
FIG. 34F is another cross-sectional view of the die body shown in FIGS. 34A-34E.

Referring to FIGS. 34E and 34F, in one embodiment, distal ends of the flow channels 586 are preferably in communication with the cone opening 526 that is formed in the distal face 518 of the die body 502.

Figure 35:
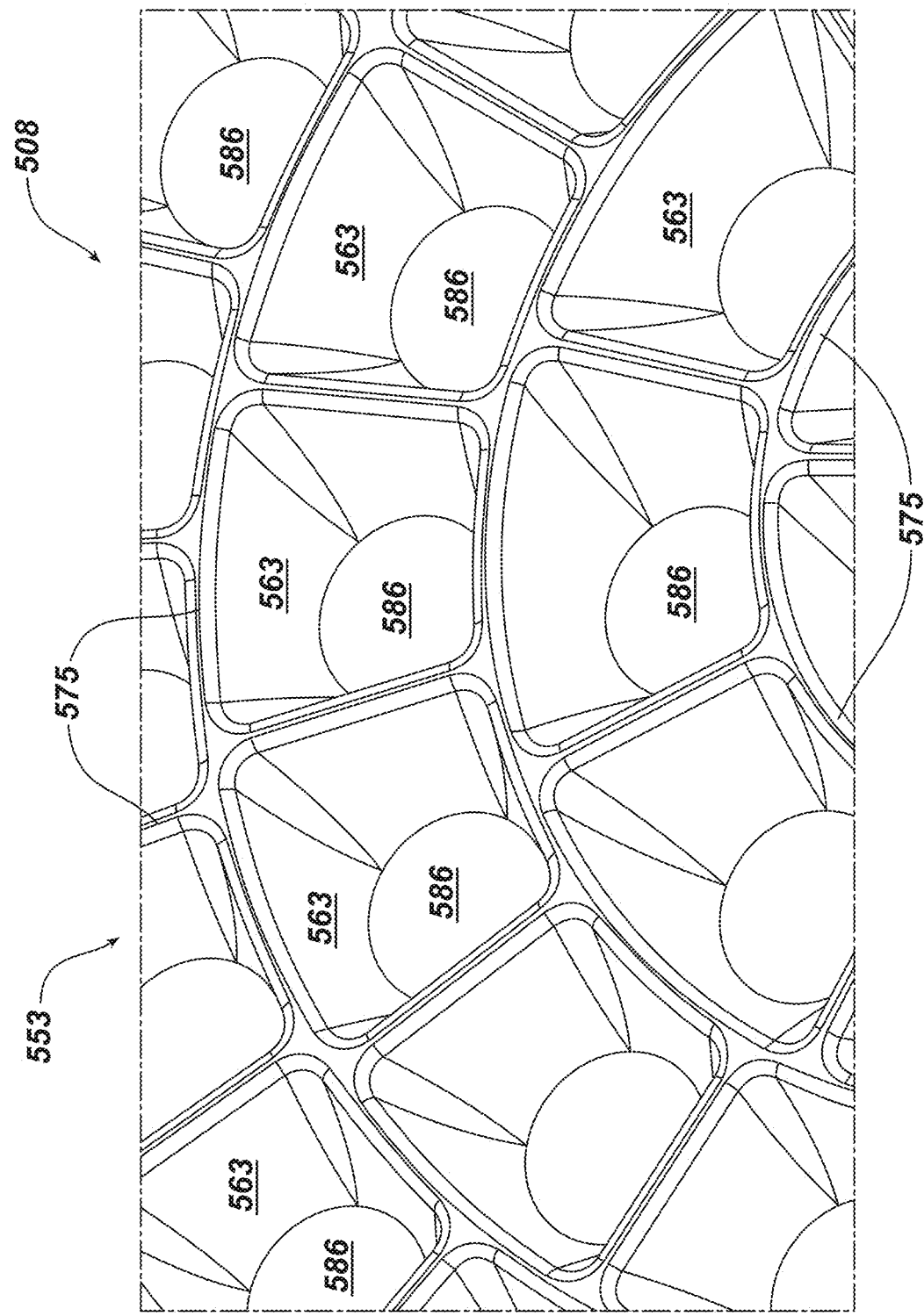
FIG. 35 is a perspective view of a section of the proximal side of the die body shown in FIGS. 34A-34F with contoured entrance zones that surround polymer melt flow holes, in accordance with one embodiment of the present patent application.

Referring to FIGS. 34E-34F and 35, in one embodiment, the inlet opening 508 of the die body 502 preferably includes the wetted area 553 that contains the contoured entrance zones 563 that desirably surround and are in communication with the proximal ends of each of the respective flow channels 586. In one embodiment, each contoured entrance zone 563 preferably includes contoured surfaces that extend distally from a common plane 552 that extends across the width of the inlet opening 508. The contoured entrance zones preferably extend distally to the proximal end of each flow channel 586 associated therewith. In one embodiment, each contoured entrance zone 563 preferably has substantially no planar or flat surfaces normal to the central axes $A_6$ of the respective flow channels 586 associated therewith.

In one embodiment, the contoured entrance zone 563 surrounding the proximal end of each flow channel 586 directly borders the contoured entrance zone 563 surrounding the proximal end of each adjacent flow channel 586 so that there are substantially no planar surfaces normal to the direction of the central axes $A_6$ of the respective flow channels 586 that remain between adjacent channels at the common plane 552 of the inlet opening 508 of the die body 502. The contoured surfaces of the contoured entrance zones 563 may include sloping surfaces, and curved surfaces including concave curved surfaces and convexly curved surfaces.

In one embodiment, the inlet opening 508 of the die body 502 preferably includes ridges 575 that preferably surround the contoured entrance zones 563. The ridges 575 may have convexly curved surfaces that are substantially devoid of any flat or planar surfaces that are normal to the direction of the central axes $A_6$ of the respective flow channels 586. In one embodiment, the ridges 575 lie in the common plane 552 (FIG. 34E) that extends across the width of the inlet opening 508 of the die body 502. In one embodiment, the ridges 575 preferably contact and support a distal face of the filtering element 585 (FIG. 33A) to minimize the risk of deformation of the filtering element when the filtering element is exposed to high pressure during an extrusion process.

In one embodiment, the contoured entrance zones 563 have substantially no planar or flat surfaces normal to the direction of the central axes $A_6$ of the respective flow channels 586, thereby eliminating and/or minimizing the presence of dead areas within the wetted area 553 of the inlet opening 508 of the die body 502.

Figure 36A:
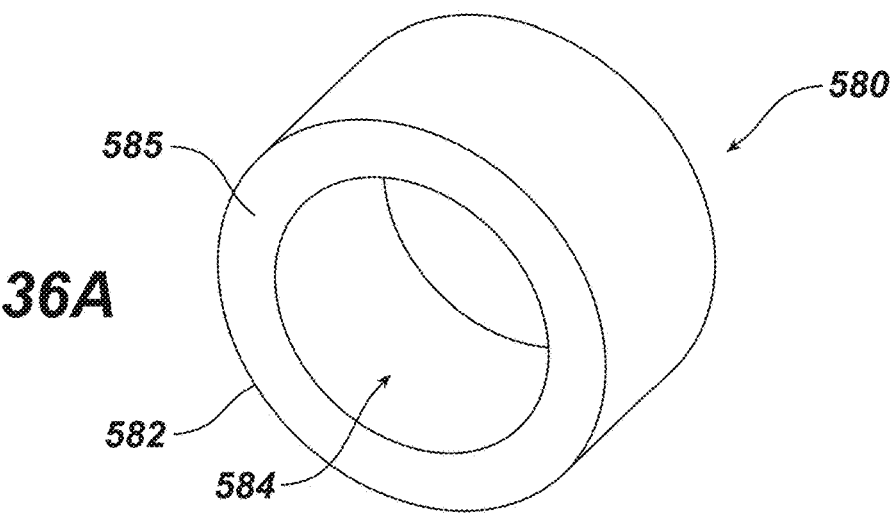
FIG. 36A is a perspective view of the tubular adapter shown in FIG. 33A.
Figure 36B:
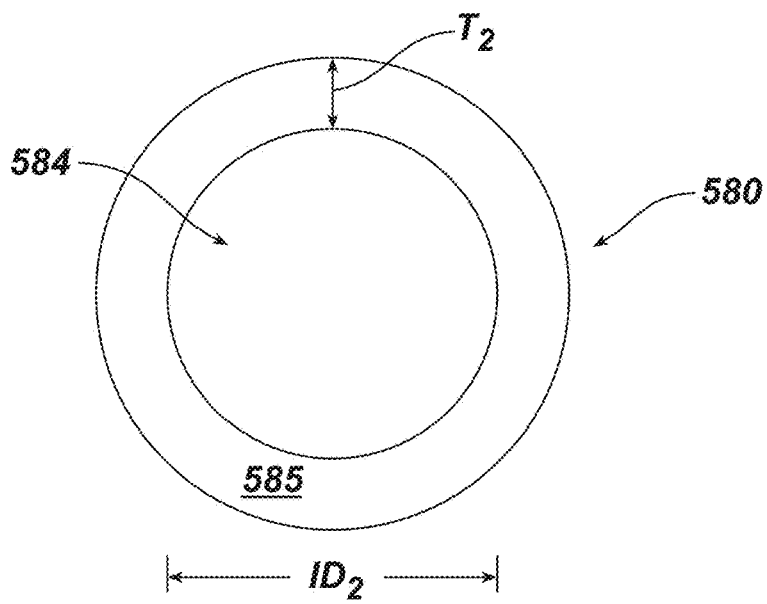
FIG. 36B is a proximal end view of the tubular adapter shown in FIG. 36A.
Figure 36C:
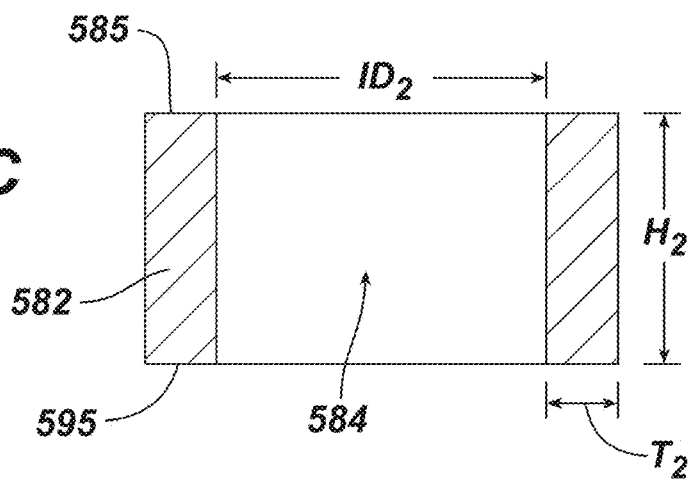
FIG. 36C is a cross-sectional view of the tubular adapter shown in FIGS. 36A and 36B.

Referring to FIGS. 36A-36C, in one embodiment, the polymer extrusion die assembly 600 (FIG. 33A) may include the tubular adapter 580, which is adapted to be disposed between a pump block (not shown) and the proximal end 512 of the die body 502 (FIG. 33A), whereupon a polymer melt may be forced into the inlet opening at the proximal end of the tubular adapter 580.

In one embodiment, the tubular adapter 580 preferably includes a tubular wall 582 that surrounds a hollow space 584. In one embodiment, polymer mixing and/or filtering elements, such as stainless steel balls, sintered and/or wire mesh screens, may be held within the hollow space 584 to homogenize the polymer melt and/or to filter impurities from the polymer stream. In one embodiment, the tubular wall 582 preferably has a proximal surface 585 and distal surface 595, which may serve as sealing faces when the tubular adapter 580 is installed in a polymer passage line.

In one embodiment, the tubular wall 582 of the tubular adapter 580 may have an outer diameter $OD_x$ of about 2-5 cm that is equal to the inner diameter of the annular groove 520 that surrounds the inlet opening 508 of the die body 502 (FIG. 33A). The tubular wall 582 may have a wall thickness $T_2$ of about 2-8 mm, a height $H_2$ of about 1-4 cm, and an inner diameter $ID_2$ that matches the outer diameter of the inlet opening 508 of the die body 502.

Figure 37A:
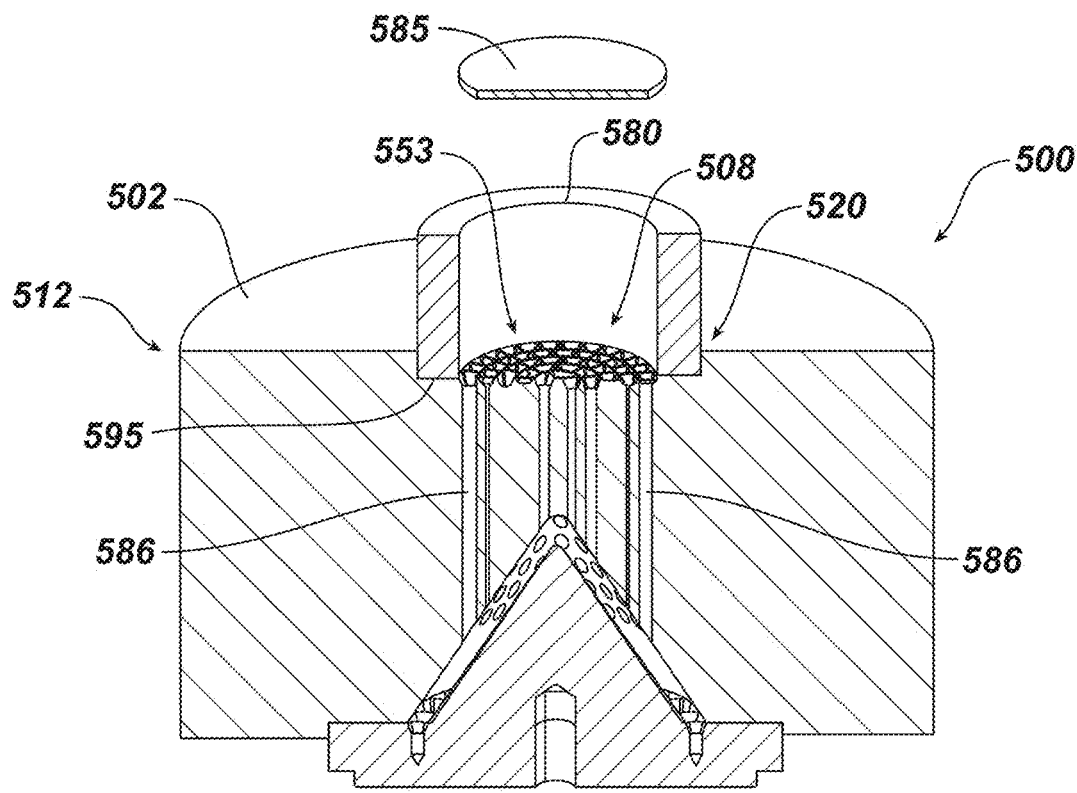
FIG. 37A is a cross-sectional view of a polymer extrusion die assembly including a tubular adapter, a die body, a spinneret, and a filtering screen adapted to be inserted into a cylindrical hollow space of the tubular adapter for covering polymer melt flow holes at a proximal end of the die body, in accordance with one embodiment of the present patent application.
Figure 37B:
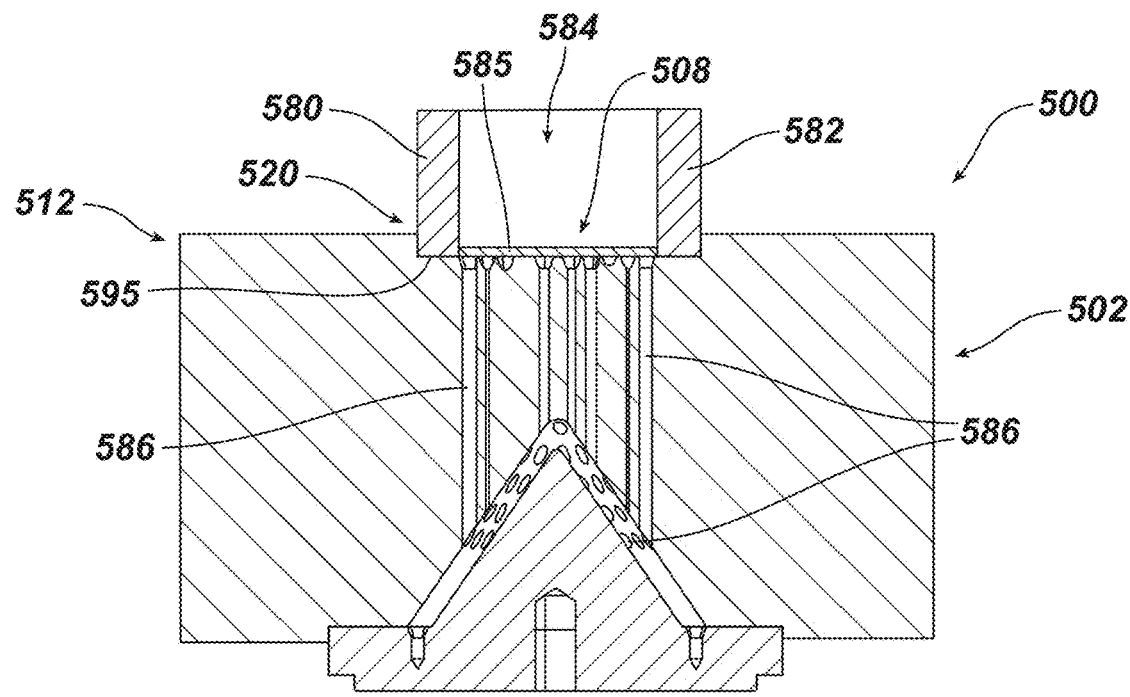
FIG. 37B is a cross-sectional view of the polymer extrusion die assembly of FIG. 37A with the filtering screen inserted into the cylindrical hollow space of the tubular adapter for covering the polymer melt flow holes at the proximal end of the die body.

Referring to FIGS. 37A and 37B, in one embodiment, the tubular adapter 580 is preferably assembled with the inlet opening 508 of the die body 502. The die body includes the annular groove 520 (FIG. 33A) that surrounds the inlet opening 508, which is adapted to seat the distal sealing surface 595 at the distal end of the cylindrical wall 582 of the tubular adapter 580. FIGS. 37A and 37B show the tubular adapter 580 after it has been seated in the annular groove 520 of the die body 502. The hollow space 584 of the tubular adapter 580 is preferably aligned with the inlet opening 508 of the die body 502.

In one embodiment, with the tubular adapter 580 assembled with the inlet opening 508 at the proximal end 512 of the die body 502 of the polymer extrusion die assembly 500, the filtering element 585, such as a filtering screen, may be inserted into the cylindrical hollow space 584 that is surrounded by the cylindrical wall 582 of the tubular adapter 580. In one embodiment, the filtering element 585 preferably has an outer diameter that substantially matches the inner diameter of the cylindrical wall 582 so that the filtering element 585 completely covers the wetted area 553 of the inlet opening 508, as well as the contoured inlet zones 563 (FIG. 35) and the flow channels 586 of the die body 502.

In one embodiment, the tubular adapter 580 may be attached or fabricated as an integral part of die body 502. One or more filtering elements 585 may be inserted inside the tubular adapter 580, which may be supported directly by the ridges 575 (FIG. 35) lying in the common plane 552 (FIG. 34E). Additional mixing elements such as stainless-steel balls may also be placed inside the tubular adapter 580. In one embodiment, the proximal and distal surface 585, 595 of the tubular wall 582 of the tubular adapter 580 may serve as sealing faces when the tubular adapter is installed in a polymer passage line.

Figure 38:
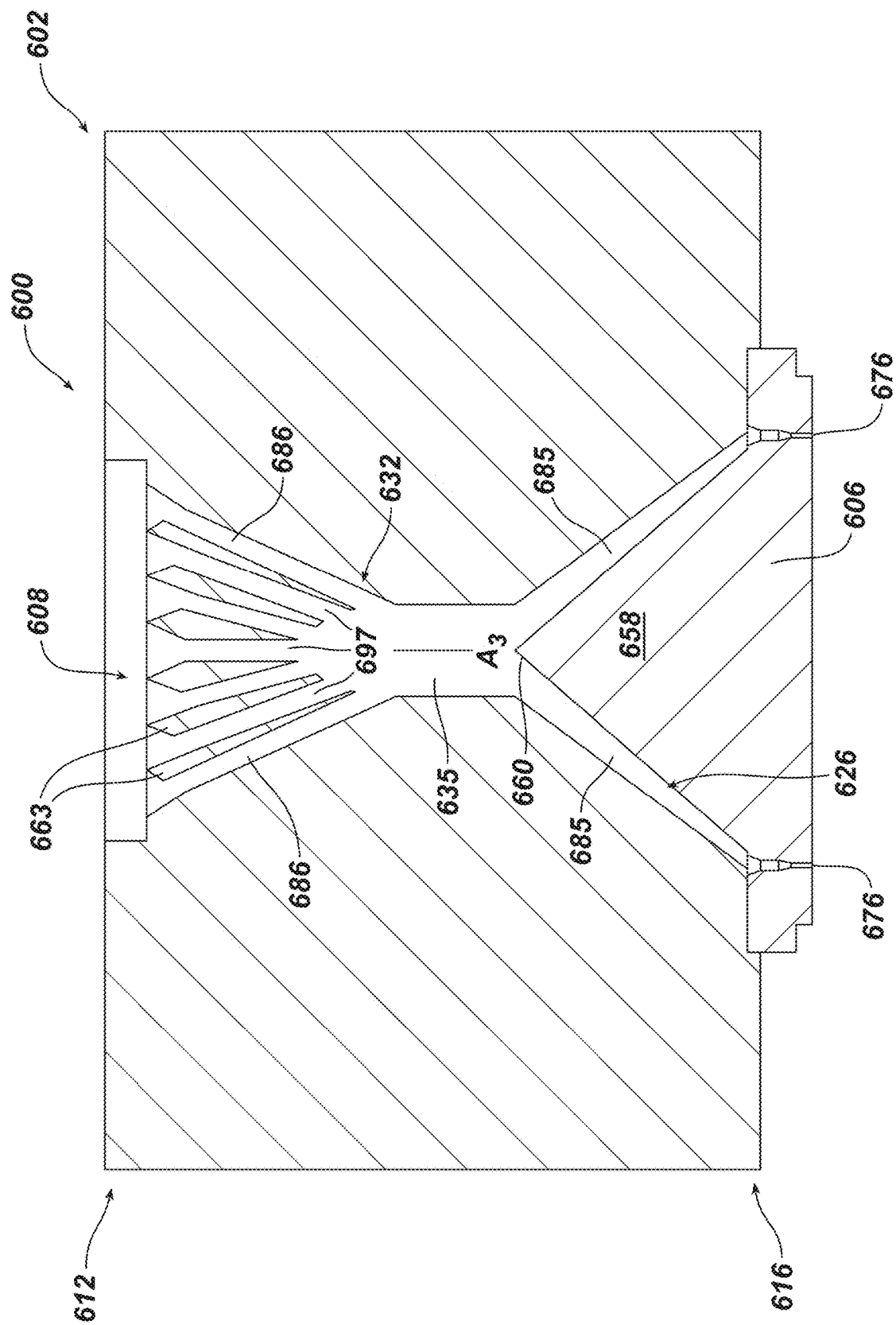
FIG. 38 is a cross-sectional view of a polymer extrusion die assembly including a die body and a spinneret, in accordance with one embodiment of the present patent application.

Referring to FIG. 38, in one embodiment, a polymer extrusion die assembly 600 preferably includes a die body 602 having has an inlet opening 608 at a proximal end 612 of the die body and a cone opening 626 located at a distal end 616 of the die body. The die body 602 preferably includes flow channels 686 that extend between contoured entrance zones 663 and a restricted flow area 635. In one embodiment, at least some of the flow channels 686 may be tilted toward a center axis $A_3$ of the die body 602. The tilting angle of the flow channels 686 may be varied in the range of about 15-50 degrees with respect to the central axis $A_3$ of the die body so that distal ends 697 of the respective flow channels 686 are positioned in a converging area 632 that is proximal to a restricted flow region 635.

In one embodiment, the polymer melt streams forced into the inlet opening 608 flow over the contoured entrance zones 663, through the flow channels 686, exit from the distal ends 697 of the respective flow channels 686, and then merge and self-mix in the converging area 632 of the die body 602. The converged polymer melt stream then preferably passes through the restricted flow region 635, which is located above the apex 660 of the cone 658 of the spinneret die 606. The converged and self-mixed polymer melt stream is preferably split into a thin layer and pushed into flow passage 685 while exchanging heat with the die body 602 before reaching the capillary holes 676 of the spinneret 606.

Figure 39A:
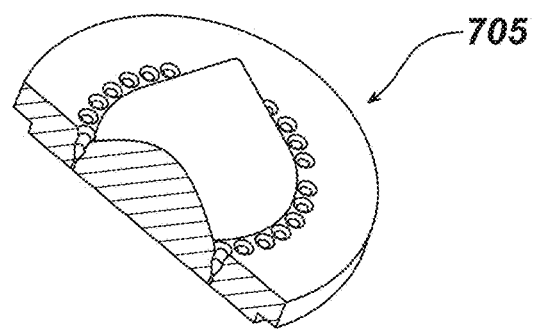
FIG. 39A is a cutaway view of a spinneret blank that is machined to make a spinneret, in accordance with one embodiment of the present patent application.
Figure 39B:
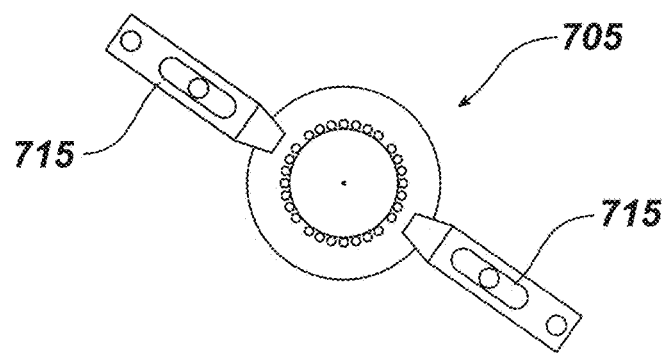
FIG. 39B shows a method of machining the spinneret blank of FIG. 39A to make a spinneret, in accordance with one embodiment of the present patent application.
Figure 39C:
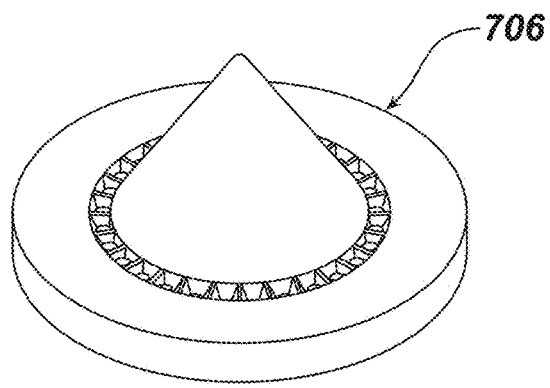
FIG. 39C is a perspective view of a spinneret that has been machined, in accordance with one embodiment of the present patent application.

Referring to FIG. 39A, in one embodiment, a method of fabricating a spinneret preferably includes using a vertical mill 3 axis CNC machine with a spinneret blank 705. Referring to FIG. 39B, in one embodiment, the spinneret blank 705 is setup on a fixture within a multi-axis CNC machine 715 with the CNC machine being programmed with G-Code. The spinneret blank 705 is desirably pre-machined to the desired shape with holes and bores finished. In one embodiment, a three dimensional (3D) part model, on Mastercam X/2019/2020 CAD software, is oriented on the XY plane with the cone shape facing vertically along a Z axis. The top of the cone preferably defines the XYZ zero location. Tool path instructions are sent to the CNC machine 715 with a roughing program using appropriately sized carbide 4 flute ball nose endmills. The tool path instructions preferably include shallow Z axis depths of cut (0.0040) moving in a clockwise direction around the XYZ axis being careful not to allow the tool to plunge in the Z axis more than set by the program. A finishing program may then be initiated to make finishing cuts to finish 3D contours to the final finished dimensions as defined within the Mastercam CAD software in order to remove any secondary material left along the edge surfaces of the contours from the rough tool path. The result is a finished spinneret 706, as shown in FIG. 39C.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention. For example, the systems, assemblies, devices and methods disclosed herein may be used for both polymer melt and polymer solution spinning.

What is claimed is:

1. A spinneret for extruding fibers, comprising:
   a plate having a proximal surface and a distal surface;
   a plurality of holes formed in the plate that extend between the proximal surface and the distal surface of the plate, wherein each of the holes has a proximal end and a distal end with a central axis extending therebetween, the distal end of each of the holes being configured to dispense filaments therefrom; and
   a plurality of contoured entrance zones formed in the proximal surface of the plate, wherein each of the contoured entrance zones is associated only with a corresponding one of the holes,
   wherein each one of the contoured entrance zones surrounds the corresponding one of the holes and tapers distally from the proximal surface of the plate to the proximal end of the corresponding one of the holes associated therewith, and wherein each of the contoured entrance zones has substantially no planar or flat surfaces normal to the central axis of the corresponding one of the holes associated therewith,
   wherein each of the contoured entrance zones includes contoured surfaces that extend from the proximal surface of the plate to the proximal end of the corresponding one of the holes associated therewith, and
   wherein a remaining non-wetted portion of the proximal surface of the plate surrounding the wetted area defines a sealed area, the sealed area having an area greater than an area of the wetted area.

2. The spinneret of claim 1, wherein the contoured surfaces include sloped surfaces, curved surfaces, concave curved surfaces, and convexly curved surfaces.

3. The spinneret of claim 1, wherein the plate has an outer diameter of about 25-150 mm.

4. The spinneret of claim 1, wherein the plurality of holes include 4-80 holes.

5. The spinneret of claim 1, wherein the holes are positioned within one or more concentric rings.

6. The spinneret of claim 5, wherein the one or more concentric rings have outer diameters of about 20-90 mm.

7. The spinneret of claim 1, wherein a distance between adjacent ones of the holes is about 3-17 mm.

8. The spinneret of claim 1, further comprising a centrally located conical projection that extends above the proximal surface of the plate.

9. The spinneret of claim 8, wherein the conical projection has a base with an outer diameter of at least 10 mm, and wherein the conical projection has a height of about 10-40 mm.

10. The spinneret of claim 9, wherein the plurality of holes are located adjacent the base of the conical projection.

11. The spinneret of claim 10, wherein the holes are arrayed in an annular configuration around the base of the conical projection.

12. The spinneret of claim 1, further comprising one or more rings formed in the proximal surface of the plate, wherein the contoured entrance zones and the holes are located within the one or more rings.

13. The spinneret of claim 12, wherein each of the one or more rings comprises:
   an inner ring;
   an outer ring surrounding the inner ring; and
   a plurality of capillary holes formed in the distal surface of the plate, wherein each of the capillary holes extends from the distal surface of the plate to the distal end of a corresponding one of the plurality of holes.

14. The spinneret of claim 13, wherein the inner ring and the outer ring are concentric.

15. The spinneret of claim 14, wherein the inner ring and the outer ring and the contoured entrance zones are contoured so that there are no surfaces that are parallel with the proximal surface of the plate within the inner and outer rings.

16. The spinneret of claim 1, wherein each of the contoured entrance zones includes a border separating the contoured entrance zone from an adjacent one of the contoured entrance zones, the border having substantially no planar or flat surfaces normal to the central axis of the holes.

17. The spinneret of claim 14, wherein the inner ring and the outer ring include a border therebetween, the border having substantially no planar or flat surfaces normal to the central axis of the holes.

\* \* \* \* \*